(12) United States Patent
Newman et al.

(10) Patent No.: US 12,241,094 B2
(45) Date of Patent: Mar. 4, 2025

(54) PHENAZINE DEGRADING AGENTS AND RELATED COMPOSITIONS, METHODS AND SYSTEMS FOR INTERFERING WITH VIABILITY OF BACTERIA

(71) Applicant: CALIFORNIA INSTITUTE OF TECHNOLOGY, Pasadena, CA (US)

(72) Inventors: Dianne K. Newman, Pasadena, CA (US); Kyle C. Costa, Altadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 597 days.

(21) Appl. No.: 17/027,587

(22) Filed: Sep. 21, 2020

(65) Prior Publication Data

US 2021/0032603 A1    Feb. 4, 2021

Related U.S. Application Data

(62) Division of application No. 15/466,839, filed on Mar. 22, 2017, now Pat. No. 10,913,936.

(60) Provisional application No. 62/430,769, filed on Dec. 6, 2016, provisional application No. 62/311,819, filed on Mar. 22, 2016.

(51) Int. Cl.
| C12N 9/02 | (2006.01) |
| A61K 38/44 | (2006.01) |
| A61K 45/06 | (2006.01) |
| C12N 9/06 | (2006.01) |
| C12Q 1/26 | (2006.01) |

(52) U.S. Cl.
CPC ............ *C12N 9/0032* (2013.01); *A61K 38/44* (2013.01); *A61K 45/06* (2013.01); *C12Q 1/26* (2013.01); *C12Y 105/03* (2013.01); *G01N 2500/04* (2013.01); *G01N 2500/10* (2013.01)

(58) Field of Classification Search
CPC .................................................... C12N 9/0004
See application file for complete search history.

(56) References Cited

U.S. PATENT DOCUMENTS

| 6,004,438 | A | 12/1999 | Woodson |
| 9,926,562 | B2 | 3/2018 | Chatziantoniou et al. |
| 10,689,613 | B2 * | 6/2020 | Newman .................. C12N 1/20 |
| 10,689,713 | B2 | 6/2020 | Chelliserry et al. |
| 10,913,936 | B2 | 2/2021 | Newman et al. |
| 11,827,944 | B2 | 11/2023 | Ismagilov et al. |

(Continued)

FOREIGN PATENT DOCUMENTS

| CN | 115297895 A | 11/2022 |
| KR | 20140140597 A | 12/2014 |

(Continued)

OTHER PUBLICATIONS

Studer. Residue mutations and their impact on protein structure and function: detecting beneficial and pathogenic changes. Biochem. J. (2013) 449, 581-594.*

(Continued)

*Primary Examiner* — Yong D Pak
(74) *Attorney, Agent, or Firm* — Steinfl + Bruno LLP

(57) ABSTRACT

Provided herein are phenazine degrading agents, methods and systems for interfering with viability of bacteria and related antimicrobial and compositions.

16 Claims, 36 Drawing Sheets

Specification includes a Sequence Listing.

(56) References Cited

U.S. PATENT DOCUMENTS

| | | | |
|---|---|---|---|
| 2013/0022578 A1* | 1/2013 | Newman | C12N 1/36 544/182 |
| 2013/0095184 A1 | 4/2013 | Lyczak et al. | |
| 2015/0073491 A1 | 3/2015 | Ehrensberger et al. | |
| 2017/0275597 A1 | 9/2017 | Newman et al. | |
| 2019/0142864 A1 | 5/2019 | Newman et al. | |
| 2020/0362299 A1 | 11/2020 | Newman et al. | |
| 2021/0322462 A1 | 10/2021 | Newman et al. | |
| 2022/0175892 A1 | 6/2022 | Newman et al. | |

FOREIGN PATENT DOCUMENTS

| | | |
|---|---|---|
| WO | 93/21511 A1 | 10/1993 |
| WO | 2019/097241 A1 | 5/2019 |
| WO | 2022/099024 A1 | 5/2022 |

OTHER PUBLICATIONS

Costa. Enzymatic Degradation of Phenazines Can Generate Energy and Protect Sensitive Organisms from Toxicity. MBio. vol. 6, Issue 6, Nov./Dec. 2015.*

A0A0N9Y7W5_MYCFO. UniProtKB/TrEMBL Database. Jan. 20, 2016.*

Advisory Action for U.S. Appl. No. 15/394,138, filed Dec. 29, 2016, on behalf of California Institute of Technology. Mail Date: Sep. 22, 2022. 8 Pages.

Aisen P., Leibman A. 1968; "The stability constant of the Fe3+ conalbumin complexes". Biochemical and Biophysical Research Communications, vol. 30, No. 4:407-413.

Alekshun, M.N. "New advances in antibiotic development and discovery." *Expert Opinion on Investigational Drugs* 14(2). 2005. pp. 117-134. 18 Pages.

Angehrn, Peter, et al. "New antibacterial agents derived from the DNA gyrase inhibitor cyclothialidine." Journal of medicinal chemistry, vol. 47, No. 6 (2004): 1487-1513.

Chin-A-Woeng, T.F.C. et al., "Introduction of the phzH gene of Pseudomonas chlororaphis PCL1391 extends the range of biocontrol ability of phenazine-1-carboxylic acid-producing *Pseudomonas* spp. Strains", (2001) Mol. Plant-Microbe Interact., vol. 14, No. 8, pp. 1006-1015.

Danzer, K., "Selectivity and specificity in analytical chemistry. General considerations and attempt of a definition and quantification," *Fresenius J Anal Chem 369*, pp. 397-402. Mar. 2001. Website: doi.org/10.1007/s002160000684.

Google Scholar Search for "Treatment with Fluoroshikimate Antibiotics + Phenazine Inhibitor Treats Bacterial Infection," 2 Pages. Updated search on Sep. 16, 2022.

He, Ze, and Michael D. Toney. "Direct detection and kinetic analysis of covalent intermediate formation in the 4-amino-4-deoxychorismate synthase catalyzed reaction." Biochemistry 45.15 (2006): 5019-5028.

Hedstrom, L., "Enzyme Specificity and Selectivity," in eLS, (Ed.). Feb. 15, 2010. 8 pages. Website: doi.org/10.1002/9780470015902. a0000716.pub2.

Heeb, S., et al. "Regulatory Roles of the GacS/GacA two-component system in plant-associated and other Gram-negative bacteria", MPMI vol. 14, No. 12, 2001, pp. 1351-1363, submitted Jul. 18, 2001 (13 pages).

Levin, Anna S., et al. "Intravenous colistin as therapy for nosocomial infections caused by multidrug-resistant Pseudomonas aeruginosa and Acinetobacter baumannii." Clinical Infectious Diseases 28.5 (1999): 1008-1011.

Mavrodi, D.V. et al., "A Seven-Gene Locus for Synthesis of Phenazine-1-Carboxylic Acid by Psuedomonas fluorescens 2-79", (May 1998), J. Bacteriol., vol. 180, No. 9, pp. 2541-2548.

Maynard, Adam et al. "Antibiotic Korormicin A Kills Bacteria by Producing Reactive Oxygen Species" Journal of Bacteriology, vol. 201, Issue 11, e00718-18, Jun. 2019. pp. 1-11.

McDonald, M. et al. "Phenazine Biosynthesis in Pseudomonas fluorescens: Branchpoint from the Primary Shikimate Biosynthetic Pathway and Role of Phenazine-1,6-dicarboxylic Acid", J. Am. Chem. Soc., 2001, 123, 38, pp. 9459-9460.

Merriam-Webster entry for "pathway," as available Apr. 25, 2009, retrieved Oct. 16, 2022 from the WayBackMachine.com (1 page).

Non-Final Office Action for U.S. Appl. No. 16/885,131, filed May 27, 2020 on behalf of California Institute of Technology Mail Date: Sep. 2, 2022 18 pages.

Non-Final Office Action issued by the USPTO for U.S. Appl. No. 15/394,138, mailing date Nov. 10, 2022, 15 pages.

Notice of Allowance for U.S. Appl. No. 16/885,131, filed May 27, 2020 on behalf of California Institute of Technology. Mail Date: Mar. 27, 2023. 20 pages.

Ohara, Hiroshi, and Toyozo Terasima. "Lethal effect of mitomycin-C on cultured mammalian cells." GANN Japanese Journal of Cancer Research 63.3 (Jun. 1972): 317-327.

Pierson III, L.S. et al., "Molecular analysis of genes encoding phenazine biosynthesis in the biological control bacterium Pseudomonas aureofaciens 30-84", (Dec. 1995) FEMS Microbiol. Lett., vol. 134, Issue 2-3, pp. 299-307.

Printout from Merriam-Webster for the entry "selecting" as of Apr. 22, 2009. 1 page.

Printout from Merriam-Webster for the entry "selectivity" as of Apr. 22, 2009. 1 page.

Printout from Merriam-Webster for the entry "specificity" as of Apr. 22, 2009. 1 page.

Printout of Merriam Webster's definition of "disrupt" 2005 (1 pg). Downloaded through the Wayback Machine.

Reimmann, C. et al., "The global activator GacA of Pseudomonas aeruginosa PAO positively controls the production of the autoinducer N-butryryl-homoserine lactone and the formation of the virulence factors pyocyanin, cyanide, and lipase", Molecular Microbiology (1997), 24(2), 309-319.

Restriction Requirement for U.S. Appl. No. 17/520,345, filed Nov. 5, 2021 on behalf of California Institute of Technology, et al. Mailed on Feb. 6, 2023. 25 pages.

Restriction Requirement issued by the USPTO for U.S. Appl. No. 17/027,587, mailing date Jan. 12, 2023, 9 pages.

System—Definition by Merriam-Webster, Dated: Dec. 6, 2010. 2 pages.

Vandrisse C. M. et al., "Leveraging the soil-clinic axis for the development of novel microbial therapeutics", Poster. The Weizmann-Caltech Symposium on the Carbon Cycle. Rehovot, Israel, Feb. 2020.

Vessman, J., et al., "Selectivity in analytical chemistry (IUPAC Recommendations 2001)," *Pure and Applied Chemistry*, vol. 73, No. 8, 2001, pp. 1381-1386. 6 Pages. https://doi.org/10.1351/pac200173081381.

Wang, Dongping, et al., "Roles of the Gac-Rsm pathway in the regulation of phenazine biosynthesis in Pseudomonas chlororaphis 30-84", MicrobiologyOpen 2013, 2(3): 505-524.

Wikipedia entry for "Proteobacteria," as published Oct. 25, 2007, retrieved Dec. 31, 2020 from the WayBack Machine, online: //web.archive.org (3 pages).

Wikipedia entry for "Protozoa," as published Nov. 29, 2007, retrieved Dec. 31, 2020 from the WayBackMachine.com (2 pages).

Yaeger, R.G. Excerpts of Medical Microbiology, "Chapter 77 Protozoa: Structure, Classification, Growth, and Development," published 1996 (7 pages).

Bellin, D.L., et al., "Electrochemical camera chip for simultaneous imaging of multiple metabolites in biofilms." *Nature communications*, 2016. 7(1): p. 1-10.

Blommel, P.G., et al., "Enhanced bacterial protein expression during auto-induction obtained by alteration of lac repressor dosage and medium composition." *Biotechnology progress*, 2007. 23(3): p. 585-598.

Cheluvappa, R., "Standardized chemical synthesis of Pseudomonas aeruginosa pyocyanin." *MethodsX*, 2014. 1: p. 67-73.

Cornforth, D.M., et al., "Quantitative framework for model evaluation in microbiology research using Pseudomonas aeruginosa and cystic fibrosis infection as a test case." *MBio*, 2020. 11(1): p. e03042-19.

(56) References Cited

OTHER PUBLICATIONS

Final Office Action for U.S. Appl. No. 15/394,138, filed Dec. 29, 2016, on behalf of California Institute of Technology. Mail Date: Mar. 24, 2022. 10 Pages.
Galloway, N.R., et al., "Rapid cloning for protein crystallography using type IIS restriction enzymes." *Crystal growth & design*, 2013. 13(7): p. 2833-2839.
International Search Report and Written Opinion for International PCT Application No. PCT/US2021/058275 filed on Nov. 5, 2021, on behalf of California Institute of Technology. Mail Date: Mar. 3, 2022. 13 Pages.
Jo, J., et al., "Interdependency of respiratory metabolism and phenazine-associated physiology in Pseudomonas aeruginosa PA14." *Journal of bacteriology*, 2020. 202(4): p. e00700-19.
Khersonsky, O., et al., "Automated design of efficient and functionally diverse enzyme repertoires." *Molecular cell*, 2018. 72(1): p. 178-186. e5.
Kragh et al. "Role of Multicellular Aggregates in Biofilm Formation" *mBio, American Society for Microbiology*. 2016. vol. 7, No. 3. pp 1-11. 11 pages.
Martell, et al., "Critical stability constants", vol. 6: Second Supplement. 1989: Springer. 643 pages.
Meirelles, L.A. and D.K. Newman, "Both toxic and beneficial effects of pyocyanin contribute to the lifecycle of Pseudomonas aeruginosa." *Molecular microbiology*, 2018. 110(6): p. 995-1010.
Meirelles, L.A., et al., "Bacterial defenses against a natural antibiotic promote collateral resilience to clinical antibiotics." *PLoS biology*, 2021. 19(3): p. e3001093.
Meylan, S., et al., "Carbon sources tune antibiotic susceptibility in Pseudomonas aeruginosa via tricarboxylic acid cycle control." *Cell chemical biology*, 2017. 24(2): p. 195-206.
Miroux, B. et al., "Over-production of proteins in *Escherichia coli*: mutant hosts that allow synthesis of some membrane proteins and globular proteins at high levels." *Journal of molecular biology*, 1996. 260(3): p. 289-298.
Netzer, R., et al., "Ultrahigh specificity in a network of computationally designed protein interaction pairs." *Nature communications*, 2018. 9(1): p. 1-13.
Non-Final Office Action for U.S. Appl. No. 15/394,138, filed Dec. 29, 2016, on behalf of California Institute of Technology. Mail Date: Sep. 16, 2021. 11 Pages.
O'Toole, G.A., "Microtiter dish biofilm formation assay." *Journal of visualized experiments: JoVE*, 2011(47).
Ruddy, J., et al., "Sputum tobramycin concentrations in cystic fibrosis patients with repeated administration of inhaled tobramycin." *Journal of aerosol medicine and pulmonary drug delivery*, 2013. 26(2): p. 69-75.
Saunders, S.H., et al., "Extracellular DNA promotes efficient extracellular electron transfer by pyocyanin in Pseudomonas aeruginosa biofilms." *Cell*, 2020. 182(4): p. 919-932. e19.
Schiessl, K.T., et al., "Phenazine production promotes antibiotic tolerance and metabolic heterogeneity in Pseudomonas aeruginosa biofilms." *Nature communications*, 2019. 10(1): p. 1-10.
Sezonov, G., D. Joseleau-Petit, and R. d'Ari, "*Escherichia coli* physiology in Luria-Bertani broth." *Journal of bacteriology*, 2007. 189(23): p. 8746-8749.
Spero, M.A. and D.K. Newman, "Chlorate specifically targets oxidant-starved, antibiotictolerant populations of Pseudomonas aeruginosa biofilms." *MBio*, 2018. 9(5): p. e01400-18.
Stewart, P.S., "Diffusion in biofilms." *Journal of bacteriology*, 2003. 185(5): p. 1485-1491.
Tang, X.X., et al., "Acidic pH increases airway surface liquid viscosity in cystic fibrosis." *The Journal of clinical investigation*, 2016. 126(3): p. 879-891.
Thomsen M.C.F. et al., "Seq2Logo: a method for construction and visualization of amino acid binding motifs and sequence profiles including sequence weighting, pseudo counts and two-sided representation of amino acid enrichment and depletion" *Nucleic acids research*, 2012. 40(W1): p. W281-W287.
Vandrisse, C. et al., "New high-cloning-efficiency vectors for complementation studies and recombinant protein overproduction in *Escherichia coli* and *Salmonella enterica.*" *Plasmid*, 2016. 86: p. 1-6.
Vandrisse C. M. et al., "Computationally designed pyocyanin demethylase acts synergistically with tobramycin to kill recalcitrant Pseudomonas aeruginosa biofilms" *PNAS*, vol. 118 No. 12, Oct. 2020, pp. 1-10.
Walters III, M.C., et al., "Contributions of antibiotic penetration, oxygen limitation, and low metabolic activity to tolerance of Pseudomonas aeruginosa biofilms to ciprofloxacin and tobramycin." *Antimicrobial agents and chemotherapy*, 2003. 47(1): p. 317-323.
Warszawski, S., et al., "Optimizing antibody affinity and stability by the automated design of the variable light-heavy chain interfaces." *PLoS computational biology*, 2019. 15(8): p. e1007207.
Zhu, K., et al., "Universal antibiotic tolerance arising from antibiotic-triggered accumulation of pyocyanin in Pseudomonas aeruginosa." *PLoS biology*, 2019. 17(12): p. e3000573.
International Preliminary Report on Patentability for International PCT Application No. PCT/US2021/058275 filed on Nov. 5, 2021, on behalf of California Institute of Technology. Mail Date: May 19, 2023. 7 Pages.
Merriam-Webster, "demethylate", (Year: 2023). Website: www.merriam-webster.com/dictionary/demethylate, 2023.
Non-Final Office Action for U.S. Appl. No. 15/394,138, filed Dec. 29, 2016 on behalf of California Institute of Technology et al. Mailing date Jun. 16, 2023. 41 pages.
Non-Final Office Action for U.S. Appl. No. 17/520,345, filed Nov. 5, 2021 on behalf of California Institute of Technology, et al. Mailed on Jun. 1, 2023. 51 pages.
Notice of Allowance for U.S. Appl. No. 15/394,138, filed Dec. 29, 2016 on behalf of California Institute of Technology et al. Mailing date Apr. 4, 2023. 9 pages.
Notice of Allowance for U.S. Appl. No. 16/885,131, filed May 27, 2020 on behalf of California Institute of Technology. Mail Date: Jul. 25, 2023. 8 pages.
Notification of Reopening of Prosecution Due to Consideration of an Information Disclosure Statement Filed After Mailing of a Notice of Allowance for U.S. Appl. No. 15/394,138, filed Dec. 29, 2016 on behalf of California Institute of Technology et al. Mailing date May 16, 2023. 4 pages.
Response to Rule 312 Communication for U.S. Appl. No. 16/885,131, filed May 27, 2020 on behalf of California Institute of Technology. Mail Date: Jun. 13, 2023. 2 pages.
Response to Rule 312 Communication for U.S. Appl. No. 16/885,131, filed May 27, 2020 on behalf of California Institute of Technology Mail Date: May 5, 2023. 3 pages.
Armstrong, S. and C. Ruckley, Use of a fibrous dressing in exuding leg ulcers. Journal of Wound Care, Jul. 1997. 6(7): p. 322-324.
Bockris, J.M. and L. Oldfield, The oxidation-reduction reactions of hydrogen peroxide at inert metal electrodes and mercury cathodes. Transactions of the faraday society, 1955. 51: p. 249-259.
Doucet, Nicolas. Thesis for University of Montreal, Mutagenese semi-aleatoire et analyse dynamique de Beta-lactamase TEM-1 de *Escherichia coli*. Dec. 2006. 315 pages.
Fisher, R.A., B. Gollan, and S. Helaine, Persistent bacterial infections and persister cells. Nature Reviews Microbiology, May 2017. 15(8): p. 453-464.
Gaur, Priyanka, et al. Interpretation of Antimicrobial Susceptibility Testing Using European Committe on Antimicrobial Susceptibility Testing (EUCAST) and Clinical and Laboratory Standards Institute (CLSI) Breakpoints: Analysis of Agreement. Cureus, Mar. 31, 2023, 15 (3): e36977. 8 pages.
Hareendran, A., et al., Measuring the impact of venous leg ulcers on quality of life. Journal of Wound Care, Feb. 2005. 14(2): p. 53-57.
International Search Report and Written Opinion for International Application No. PCT/US2024/026318 filed on Apr. 25, 2024 on behalf of California Institute of Technology. Mailed on Aug. 16, 2024. 13 pages.
Krasner, D., et al., The ABCs of wound care dressings. wound management, 1993. 66: pp. 66, 68-69, 72, 74-76, 78-86. 16 pages.

(56) References Cited

OTHER PUBLICATIONS

Niepa, T.H., J.L. Gilbert, and D. Ren, Controlling Pseudomonas aeruginosa persister cells by weak electrochemical currents and synergistic effects with tobramycin. Biomaterials, Oct. 2012. 33(30): p. 7356-7365.

Okshevsky, M. and R.L. Meyer, Evaluation of fluorescent stains for visualizing extracellular DNA in biofilms. Journal of Microbiological Methods, Oct. 2014. 105: p. 102-104.

Reetz, M.T. et al., Iterative saturation mutagenesis (ISM) for rapid directed evolution of functional enzymes. Nature Protocols, (Published online Apr. 12, 2007), vol. 2, No. 4, pp. 891-903.

Siloto, Rodrigo M.P. et al., Site saturation mutagenesis: Methods and Applications in protein engineering. Biocatalysis and Agricultural Biotechnology. (Online Apr. 5, 2012). 1, pp. 181-189.

Urban, MV et al. (Jun. 2019) "Hydrogen peroxide (H2O2): a review of its use in surgery." Wien Med Wochenschr 169: 222-225. DOI: 10.1007/s10354-017-0610-2.

Armstrong, S. and C. Ruckley, Use of a fibrous dressing in exuding leg ulcers. Journal of Wound Care, Jul. 1997. 6(7): p. 322-324. Abstract Only.

Boateng, J.S., et al., Wound healing dressings and drug delivery systems: a review. Journal of pharmaceutical sciences, Aug. 2008. 97(8): p. 2892-2923.

Bolton, L. and L. Van Rijswijk, Wound dressings: meeting clinical and biological needs. Dermatology nursing, Jul. 1991. 3(3): p. 146-161. 16 pages.

Bosire, E.M. and M.A. Rosenbaum, Electrochemical potential influences phenazine production, electron transfer and consequently electric current generation by Pseudomonas aeruginosa. Frontiers in Microbiology, May 2017. vol. 8, Article 892: p. 260405. 11 pages.

Certification Statement and list—37 CFR 1.98(d)(1) filed in U.S. Appl. No. 17/027,587, filed Sep. 21, 2020 on behalf of California Institute of Technology. 1 page.

Chica, R.A. et al. "Semi-rational approaches to engineering enzyme activity: Combining the benefits of directed evolution and rational design" Curr. Opin. Biotechnol., 2005, 16 (4), 378-384. An Excerpt. 23 pages.

Choi, Yongwook et al., "PROVEAN web server: a tool to predict the fuctional effect of amino acid substitutions and indels", Bioinformatics, vol. 31, Issue 16, Aug. 2015, pp. 2745-2747.

Ciemniecki, J.A. and D.K. Newman, NADH dehydrogenases are the predominant phenazine reductases in the electron transport chain of Pseudomonas aeruginosa. Molecular Microbiology, May 2023. 119(5): p. 560-573. 25 pages.

Cornell, WC et al. (Dec. 2020) Phenazine oxidation by a distal electrode modulates biofilm morphogenesis. Biofilm, 2: 100025. 6 pages.

Csernatony, Z., et al., Metal implants and MRI: A mythbuster study. Glob. Imaging Insights, May 7, 2021. 6: p. 1-4.

Dahlem Junior, M.A., et al., Quinones as an efficient molecular scaffold in the antibacterial/antifungal or antitumoral arsenal. International Journal of Molecular Sciences, Nov. 2022. 23(22): p. 14108. 16 pages. DOI: 10.3390/ijms232214108.

Dar, D., et al., Global landscape of phenazine biosynthesis and biodegradation reveals species-specific colonization patterns in agricultural soils and crop microbiomes. eLife, Sep. 15, 2020. 9: p. e59726. 23 pages.

Final Office Action for U.S. Appl. No. 17/520,345, filed Nov. 5, 2021 on behalf of California Institute of Technology, et al. Mailed on Mar. 1, 2024. 26 pages.

Fisher, R.A., B. Gollan, and S. Helaine, Persistent bacterial infections and persister cells. Nature Reviews Microbiology, May 2017. 15(8): p. 453-464. Abstract Only.

Franza, T. and P. Gaudu, Quinones: more than electron shuttles. Research in Microbiology, 2022. 173(6-7): p. 103953. 10 pages.

Gilliland, E.L., et al., Bacterial colonisation of leg ulcers and its effect on the success rate of skin grafting. Annals of the Royal College of Surgeons of England, 1988. 70(2): p. 105-108.

Gimeno, M., et al., A controlled antibiotic release system to prevent orthopedic-implant associated infections: An in vitro study. European Journal of Pharmaceutics and Biopharmaceutics, 2015. 96: p. 264-271.

Glasser, N.R., S.H. Saunders, and D.K. Newman, The colorful world of extracellular electron shuttles. Annual review of microbiology, Jul. 21, 2017. 71: p. 731-751. 28 pages.

Hareendran, A., et al., Measuring the impact of venous leg ulcers on quality of life. Journal of Wound Care, Feb. 2005. 14(2): p. 53-57. Abstract Only.

Kang, J., Y.-H. Cho, and Y. Lee, Pyocyanin and 1-Hydroxyphenazine promote anaerobic killing of Pseudomonas aeruginosa via single-electron transfer with ferrous iron. Microbiology Spectrum, Nov. 2, 2022. 10(6): p. e02312-22. 14 pages.

Keogh, D., et al., Extracellular electron transfer powers Enterococcus faecalis biofilm metabolism. MBio, March/Apr. 2018. 9(2): p. 10.1128/mbio. 00626-17. 16 pages.

Laskowski, R.A. et al. "PROCHECK: a program to check the stereochemical quality of protein structures", J Appl Cryst. 1993; 26:283-291.

Lazarus, G.S., et al., Reprint of: Definitions and guidelines for assessment of wounds and evaluation of healing. Arch Dermatol, 1994. 130(4): p. 489-493.

Light, S.H., et al., A flavin-based extracellular electron transfer mechanism in diverse Gram-positive bacteria. Nature, Oct. 2018. 562(7725): p. 140-144. 27 pages.

Mathura, V. et al. "APDbase: Amino acid Physico-chemical properties Database", Bioinformation, 1, 1, Mar. 12, 2005, pp. 2-4. Biomedical Informatics Publishing Group.

Mevers, E. et al. "An elusive electron shuttle from a facultative anaerobe" eLife, (Jun. 24, 2019), 8:e48054.15 pages DOI: elifesciences.org/articles/4805.

Mohamed, A. et al. "Hydrogen peroxide-producing electrochemical bandage controlled by a wearable potentiostat for treatment of wound infections", Biotechnol Bioeng, (Jul. 2021), 118 (7), 2815-2821. 11 pages. Website: www.ncbi.nlm.nih.gov/pmc/articles/PMC8653773/.

Niepa, T.H., J.L. Gilbert, and D. Ren, Controlling Pseudomonas aeruginosa persister cells by weak electrochemical currents and synergistic effects with tobramycin. Biomaterials, Oct. 2012. 33(30): p. 7356-7365. Abstract Only.

Okshevsky, M. and R.L. Meyer, Evaluation of fluorescent stains for visualizing extracellular DNA in biofilms. Journal of Microbiological Methods, Oct. 2014. 105: p. 102-104. Abstract Only.

Otero, Fernand Jimenez et al. "Pyocyanin-dependent electrochemical inhibition of Pseudomonas aeruginosa biofilms is synergistic with antibiotic treatment", American Society for Microbiology, mBio, (Jun. 14, 2023), vol. 14, Issue 4. 7 pages. 10-1128/mbio. 00702-23.

Park, H.Y., et al., Comparison of two fluorescent probes in preclinical non-invasive imaging and image-guided debridement surgery of *Staphylococcal* biofilm implant infections. Scientific reports, Jan. 15, 2021. 11(1): p. 1622. 13 pages.

PROCHECK and PROCHECK-NMR. Available on Feb. 26, 2016 through the Way Back Machine. 2 pages. Website: www.ebi.ac.uk/thornton-srv/software/PROCHECK/.

PROVEAN on J. Craig Venter Institute website, Available on Feb. 23, 2016 through the Way Back Machine. 1 pages. Website: provean.jcvi.org/index.php.

Raval, Y.S., et al., Hydrogen peroxide-generating electrochemical scaffold activity against trispecies biofilms. Antimicrobial agents and chemotherapy, Mar. 24, 2020. 64(4): p. 10.1128/aac. 02332-19. 6 pages.

Rosenbaum, F.P. and V. Müller, Energy conservation under extreme energy limitation: the role of cytochromes and quinones in acetogenic bacteria. Extremophiles, Nov. 2021. 25(5): p. 413-424. Doi: 10.1007/s00792-021-01241-0.

Schroth, M.N., et al., Epidemiology of Pseudomonas aeruginosa in agricultural areas. Journal of Medical Microbiology, Aug. 2018. 67(8): p. 1191-1201.

Skerman, V., V. McGowan, and P. Sneath, Approved lists of bacterial names (amended). Washington (DC), ASM Press 1989. Excerpt only. 2 pages.

(56) References Cited

OTHER PUBLICATIONS

Smith, D.J. et al., "Effect of intravenous or oral sodium chlorate administration on the fecal shedding of *Escherichia coli* in sheep". Journal Animal Science, 2013, 91: 5962-5969. Dod:10.2527/jas2013-6796.

Sultana, S.T., et al., Electrochemical scaffold generates localized, low concentration of hydrogen peroxide that inhibits bacterial pathogens and biofilms. Scientific reports, Oct. 14, 2015. 5(1): p. 1-10.

Uniprot Entry No. A0A1G9T5F4_ALLAB, published Jan. 18, 2017. 2 pages.

Urban, MV et al. (Jun. 2019) "Hydrogen peroxide (H2O2): a review of its use in surgery." Wien Med Wochenschr 169: 222-225. DOI: 10.1007/s10354-017-0610-2. Abstract Only.

Van Beilen, J.W. and K.J. Hellingwerf, All three endogenous quinone species of *Escherichia coli* are involved in controlling the activity of the aerobic/anaerobic response regulator ArcA. Frontiers in microbiology, Sep. 2016. 7: p. 208925. 11 pages. DOI: 10.3389/fmicb.2016.01339.

Wikipedia—Standard Electrode Potential (data page). Last updated Apr. 15, 2024. 16 pages. Website: en.wikipedia.org/wiki/Standard_electrode_potential_(data_page).

Wikipedia: Nerst Equation. Last updated: Dec. 27, 2023. Downloaded through the Wayback Machine on for Feb. 27, 2024. 16 page. en.wikipedia.org/wiki/Nernst_equation.

Wikipedia, "Pourbaix Diagram". Downloaded Jun. 4, 2024. Last edited Mar. 21, 2024. 11 pages. Website: en.wikipedia.org/wiki/Pourbaix_diagram.

Xi, W., et al., Point-of-care antimicrobial coating protects orthopaedic implants from bacterial challenge. Nature communications, Sep. 16, 2021. 12(1): p. 5473. 15 pages.

Zoller, S.D., et al., Evading the host response: *Staphylococcus* "hiding" in cortical bone canalicular system causes increased bacterial burden. Bone Research, Dec. 19, 2020. 8(1): p. 43. 11 pages.

Non-Final Office Action for U.S. Appl. No. 17/520,345, filed Nov. 5, 2021 on behalf of California Institute of Technology, et al. Mailed on Oct. 24, 2024. 20 pages.

\* cited by examiner

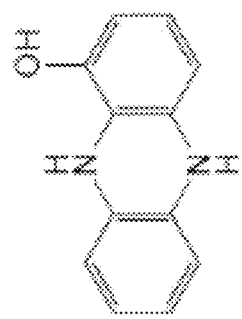
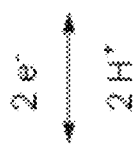
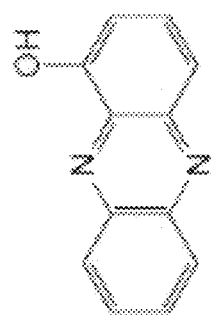
FIG. 2B
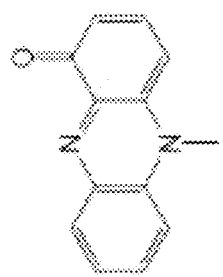
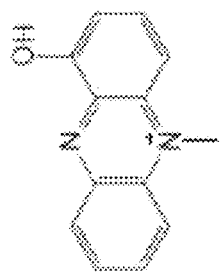
FIG. 2A

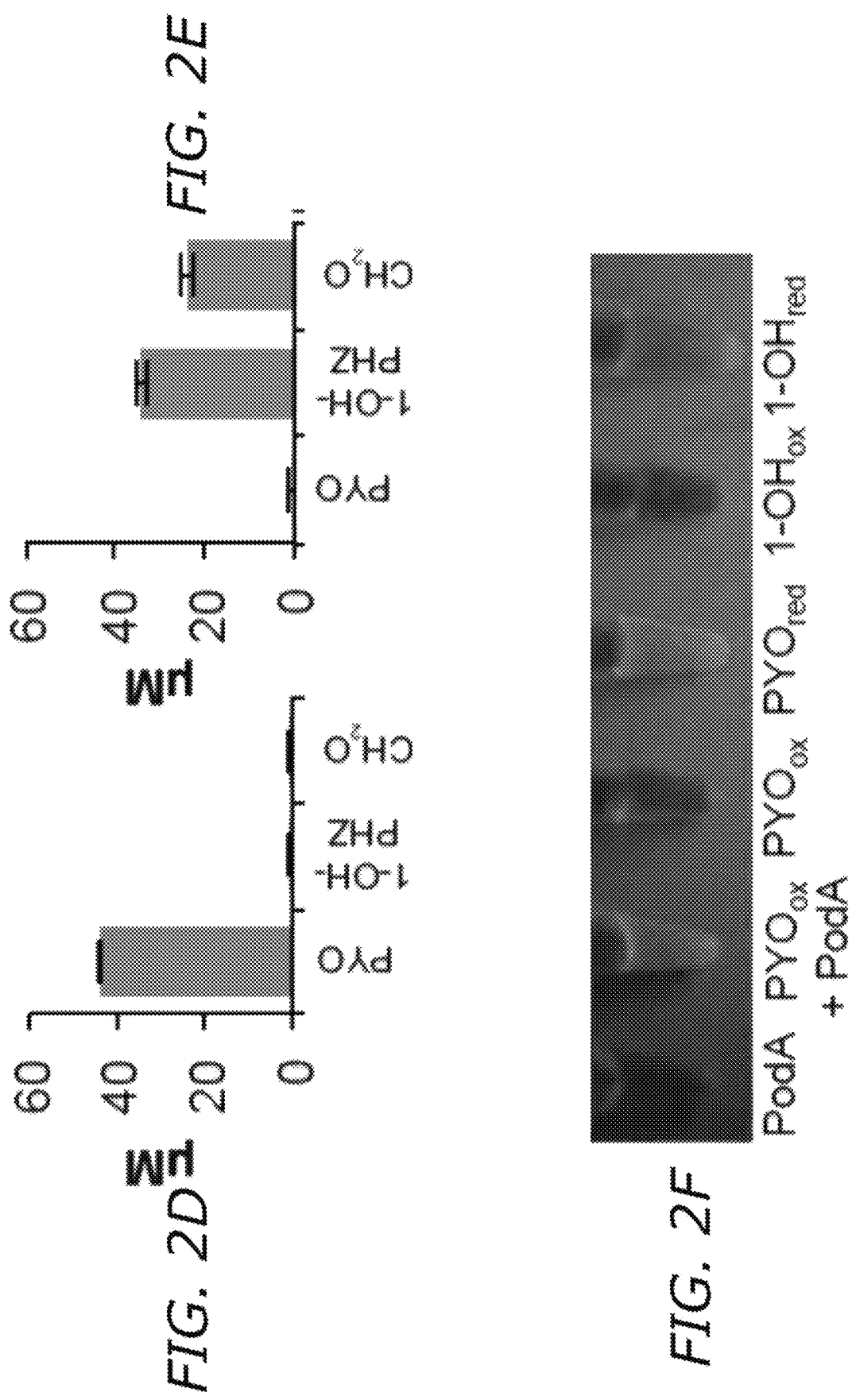

FIG. 7A
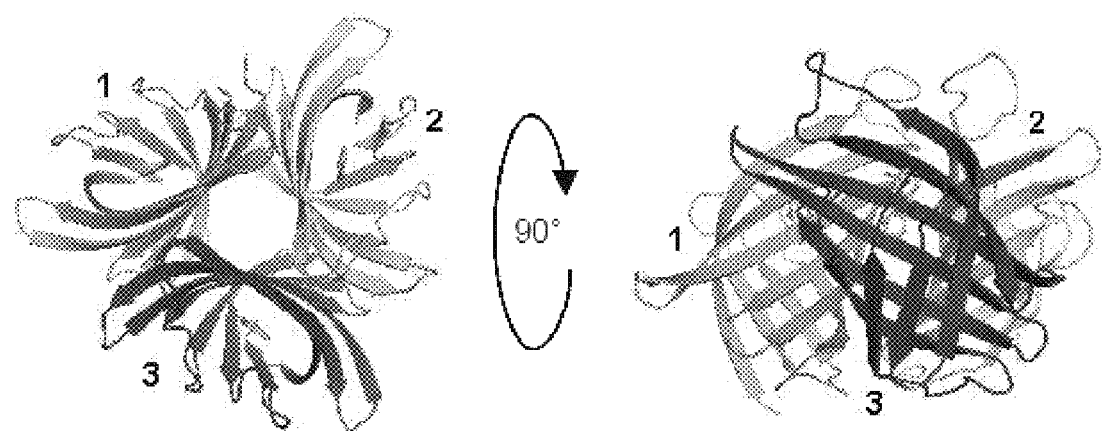
FIG. 7B
FIG. 7C
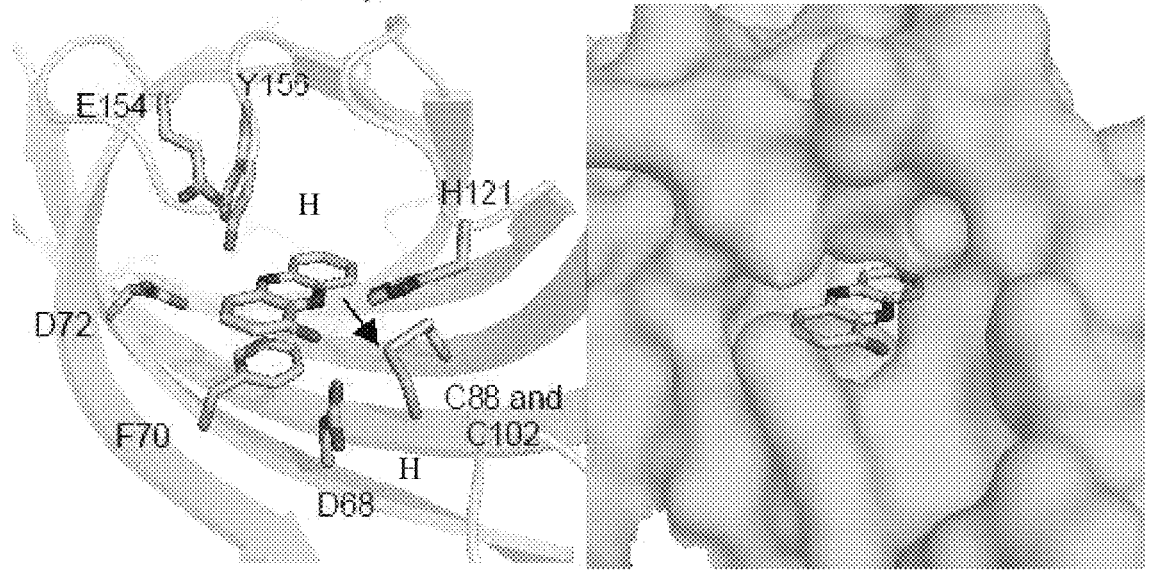

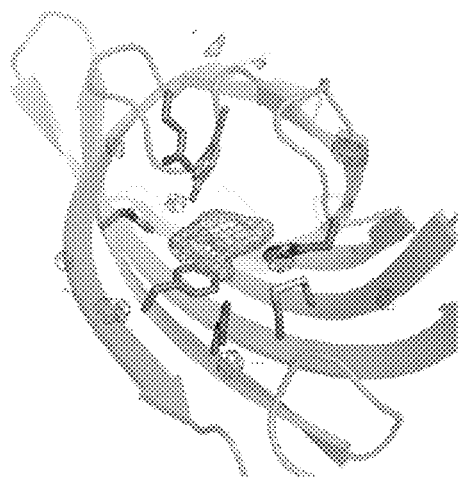
FIG. 8A
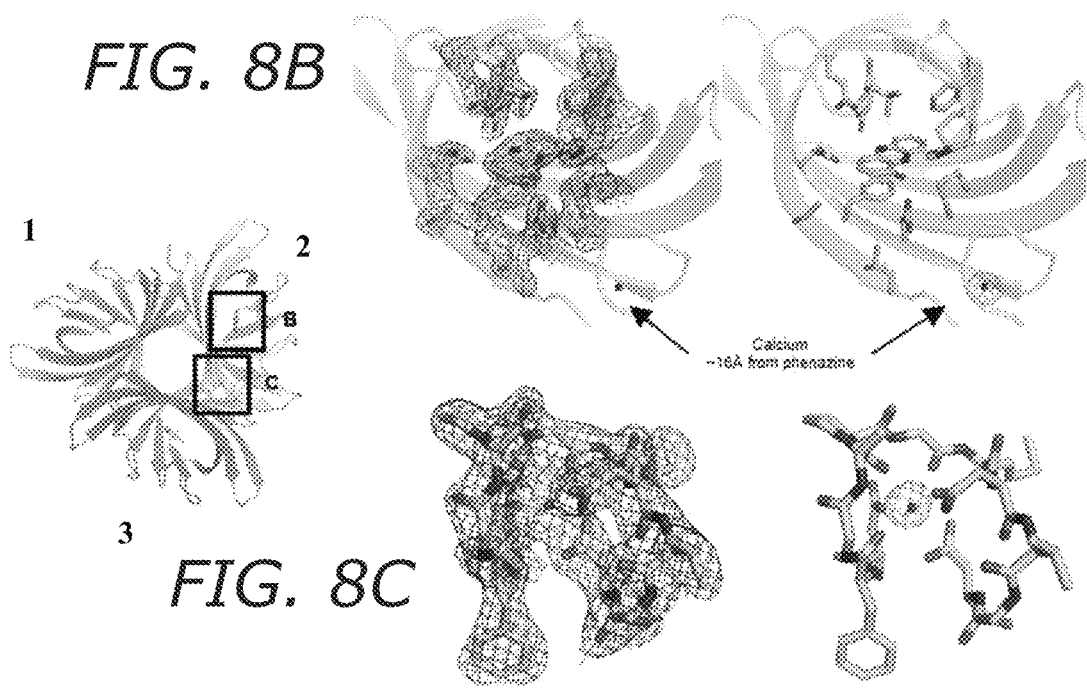
FIG. 8B
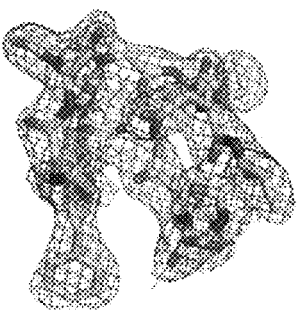
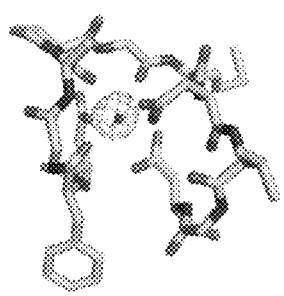
FIG. 8C

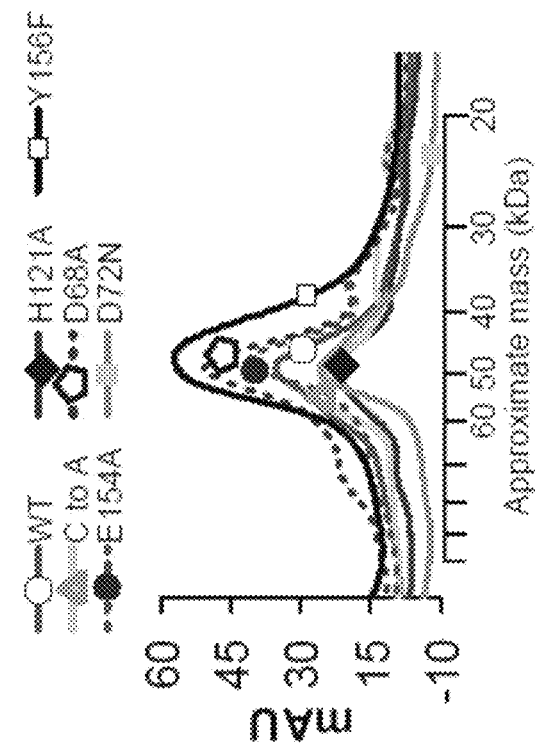
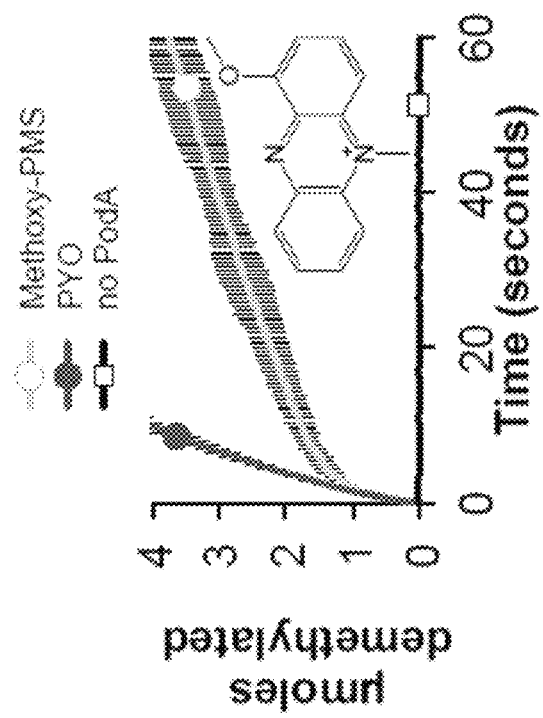
FIG. 9B
FIG. 9A

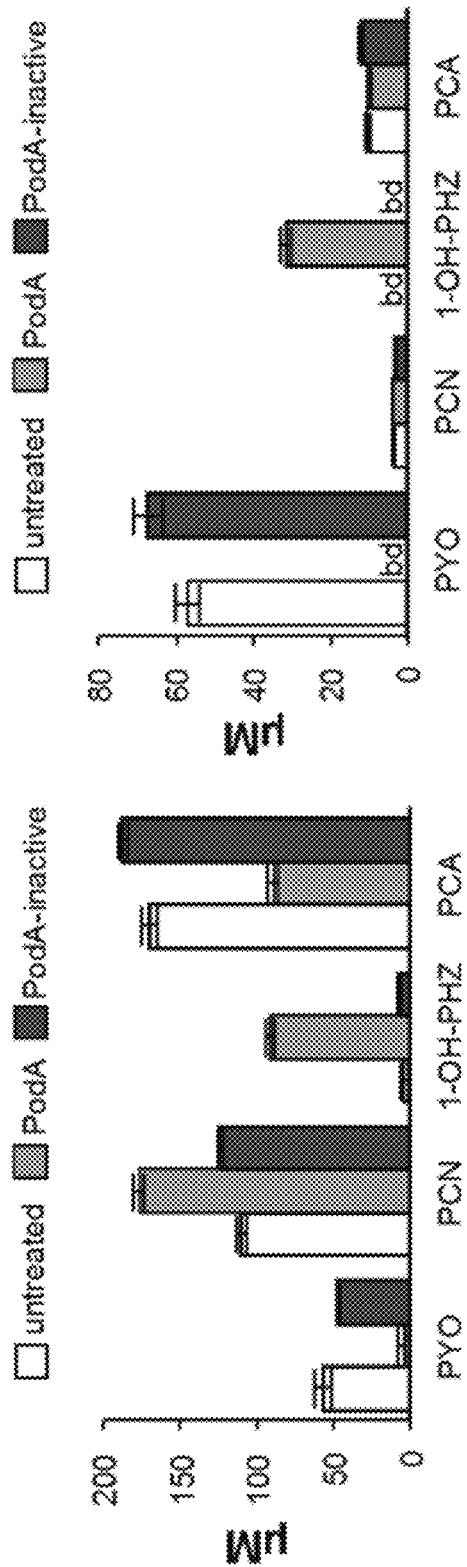

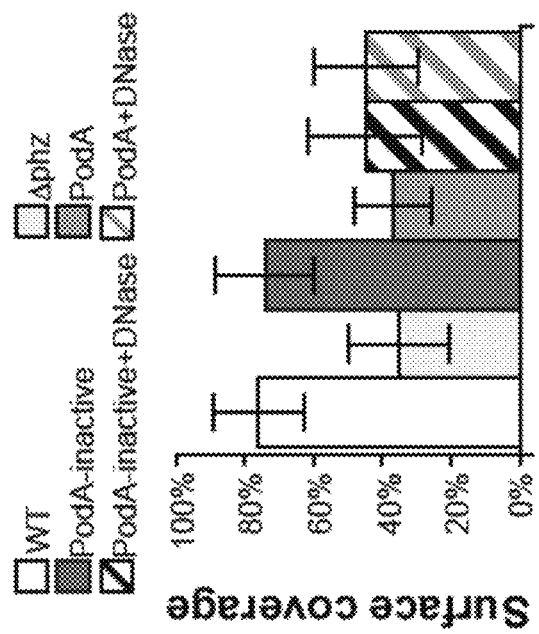
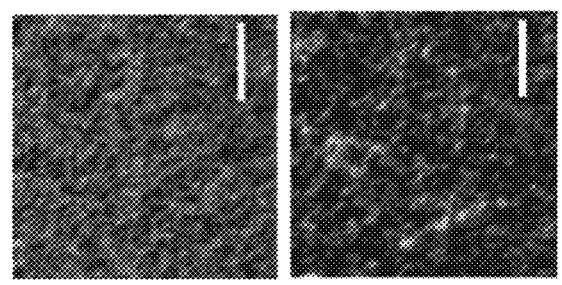
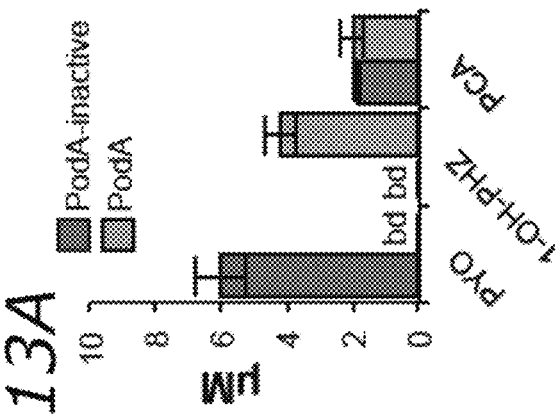
FIG. 13A FIG. 13B FIG. 13C FIG. 13D

*FIG. 20A*
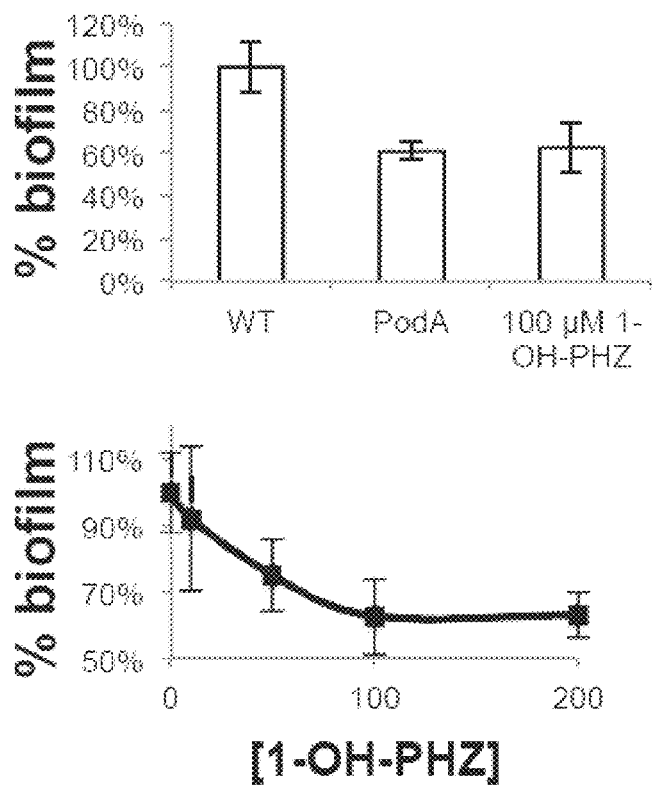
*FIG. 20B*
*FIG. 20C*
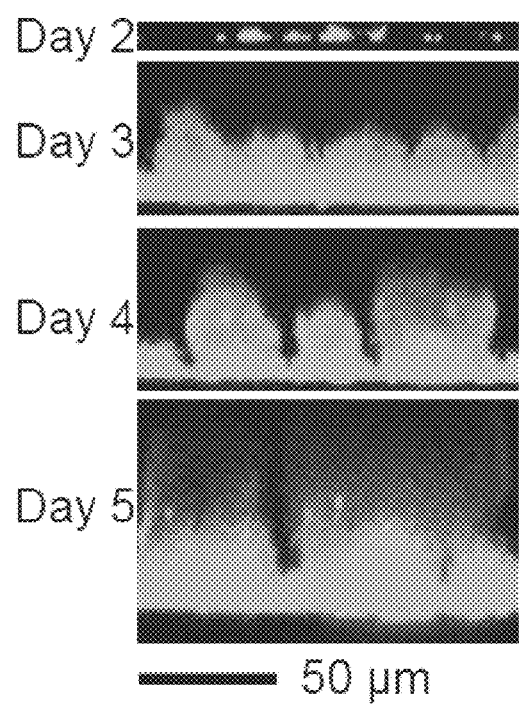

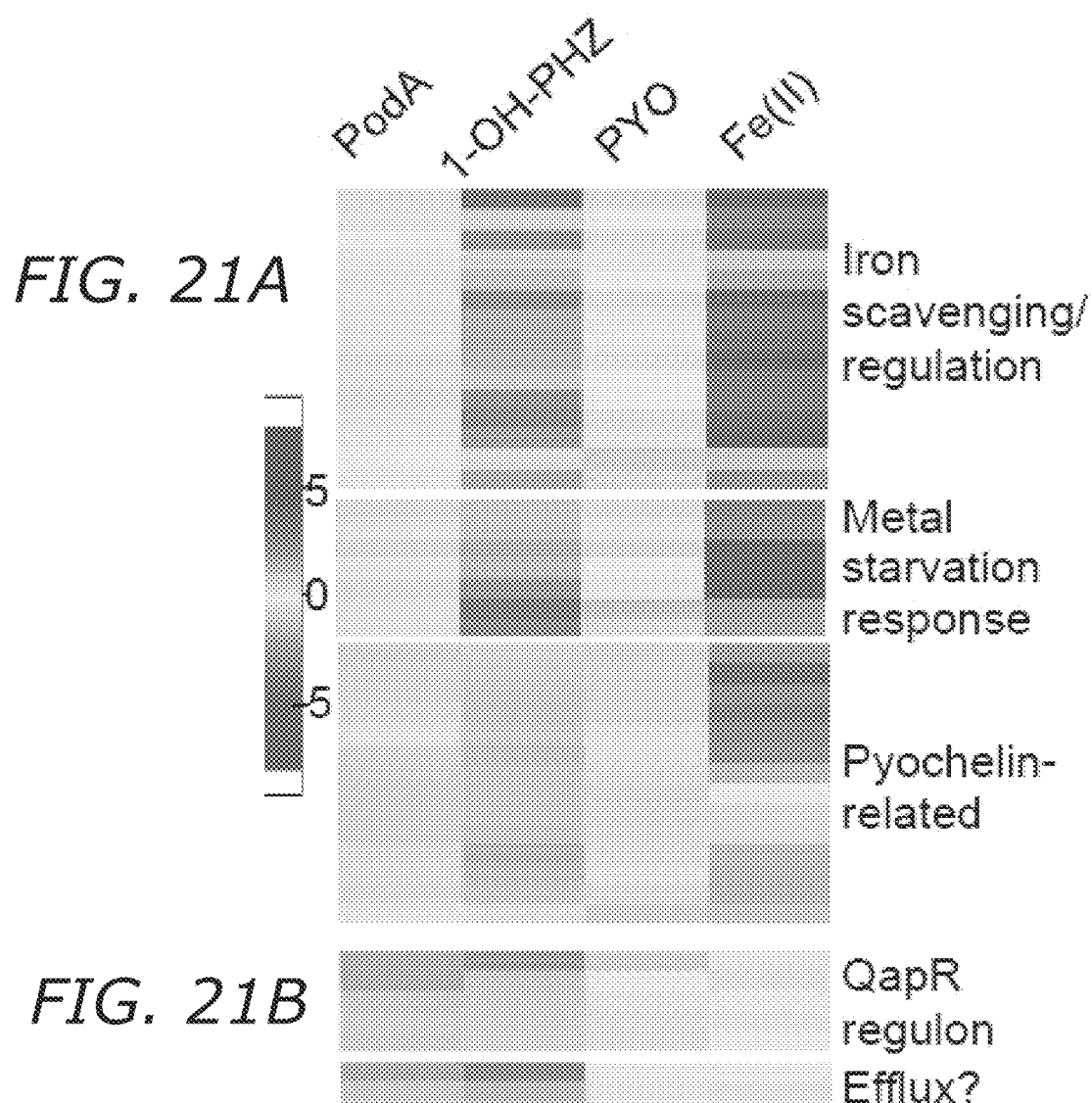

PYO removal from supernatant

Growth on PCA as C source

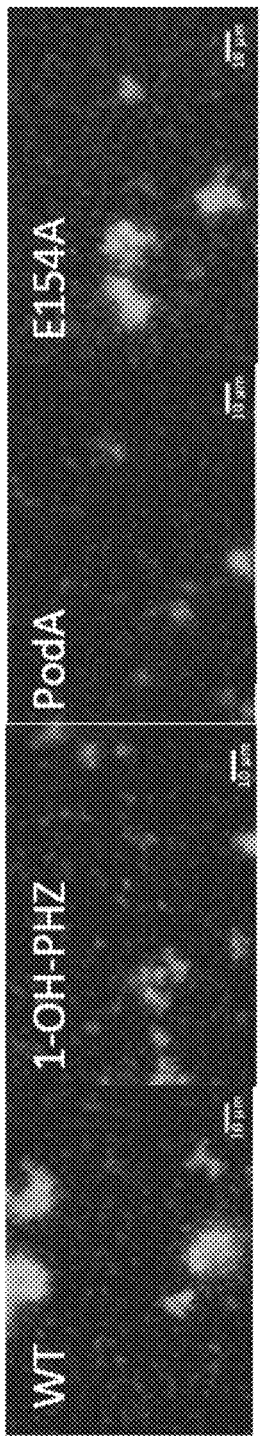
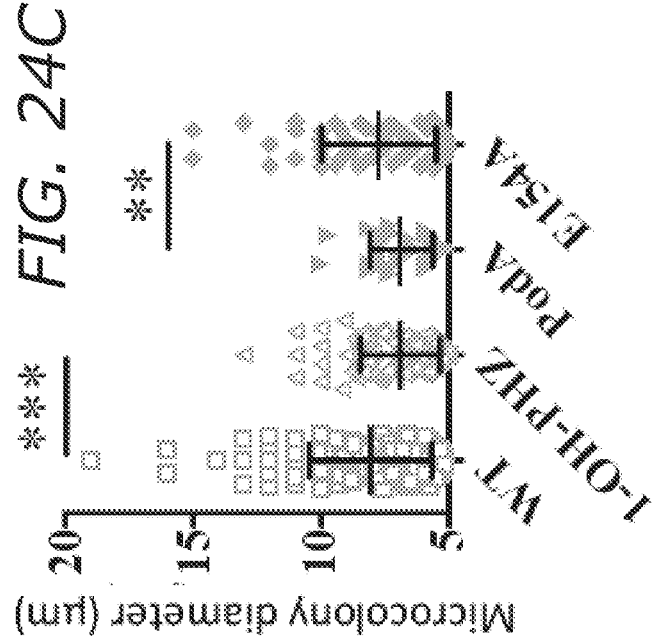
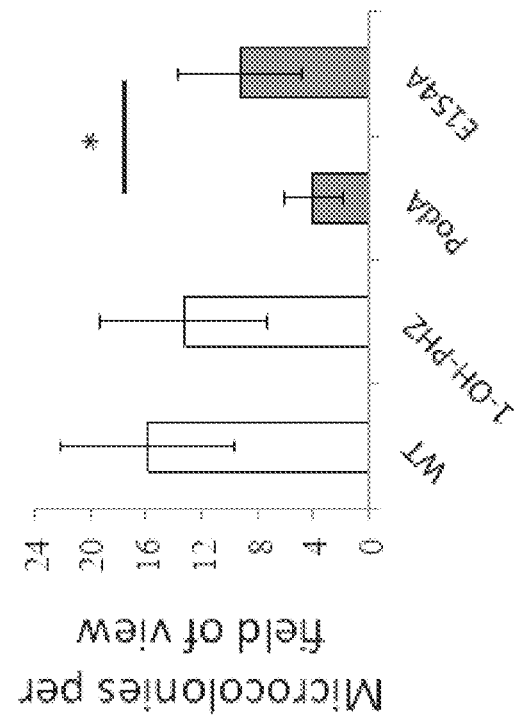

*FIG. 28A*
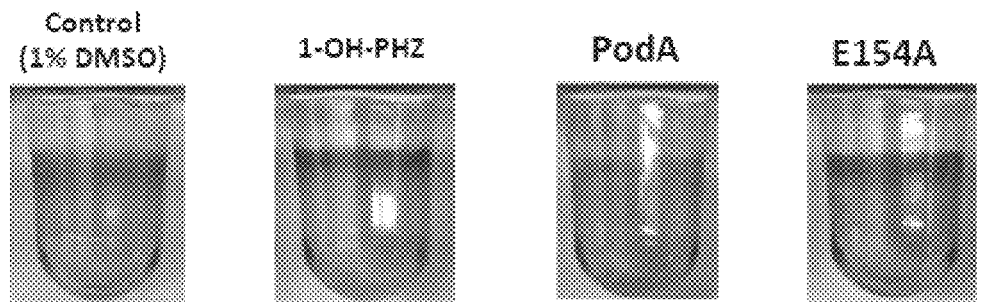
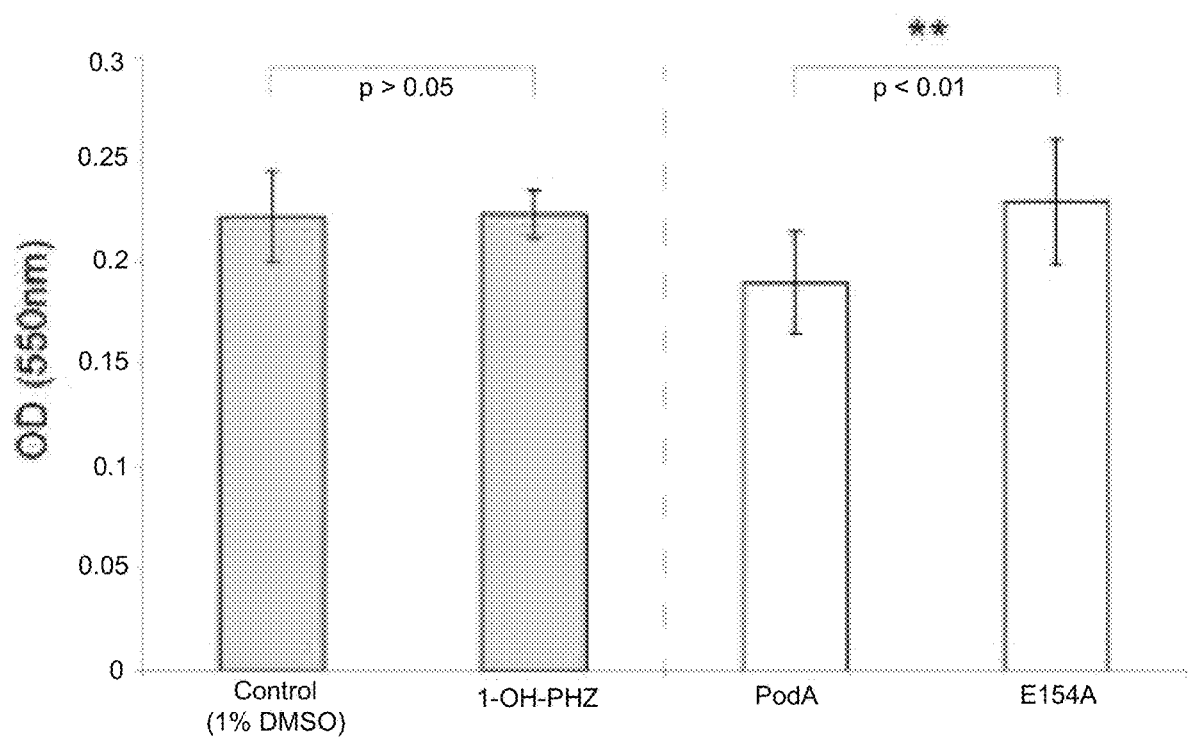
*FIG. 28B*

PHENAZINE DEGRADING AGENTS AND RELATED COMPOSITIONS, METHODS AND SYSTEMS FOR INTERFERING WITH VIABILITY OF BACTERIA

The present application is a divisional of U.S. Non-Provisional application Ser. No. 15/466,839 entitled "Phenazine Degrading Agents And Related Compositions, Methods And Systems For Interfering With Viability Of Bacteria" filed on Mar. 22, 2017, which in turn claims priority to U.S. Provisional Application No. 62/311,819 entitled "Enzymatic Disruption of Biofilms" filed on Mar. 22, 2016, and to U.S. Provisional Application No. 62/430,769, entitled "Phenazine Degrading Agents and Related Compositions, Methods and Systems for Interfering with Bacterial Viability" filed on Dec. 6, 2016, the contents of each of which are incorporated herein by reference in their entirety.

STATEMENT OF GOVERNMENT GRANT

This invention was made with government support under Grant No. AI112248 and by Grant No. HL117328 awarded by the National Institutes of Health. The government has certain rights in the invention.

FIELD

The present disclosure relates to methods and systems for interfering with the viability of bacteria and related compounds and compositions. In particular, the present disclosure relates to a phenazine degrader and related compositions, methods and systems for interfering with the viability of bacteria.

BACKGROUND

Bacterial viability has been the focus of research in the field of biological analysis, in particular when aimed at medical applications such as therapeutic or diagnostic applications.

Whether for pathological examination or for fundamental biology studies, several methods are commonly used for the detection of and interference with the viability of bacteria.

Although various methods, systems and compositions have been developed to interfere with, and in particular, to reduce bacterial viability to the extent of killing the bacteria, however antibiotic resistance and additional defense mechanisms of the microorganism have made the development of methods, systems and compositions that are able to interfere with and in particular to inhibit bacterial viability particularly challenging.

SUMMARY

Provided herein, are phenazine degrading agents and related methods, systems and compositions that in several embodiments are suitable for reducing antibiotic resistance and/or the survivability of bacteria. In several embodiments, the phenazine degrading agents and related compositions, methods and systems herein described are expected to be suitable to treat and/or prevent bacterial infection in vitro or in vivo.

According to a first aspect, a phenazine degrading agent is described that comprises a pyocyanin demethylase and/or a derivative thereof.

According to a second aspect, a method and a system to interfere with viability of phenazine producing bacteria are described. The method comprises contacting the phenazine producing bacteria with one or more phenazine degrading agents, herein described, alone or in combination with an antibiotic and/or other antimicrobial for a time and under conditions to reduce survivability and/or antibiotic resistance of the bacteria. The system comprises one or more phenazine degrading agents, one or more antibiotics and/or one or more other antimicrobials. In some embodiments of the methods and systems, the bacteria comprise persister cells.

According to a third aspect, a method and a system are described for treating and/or preventing a bacterial infection by a phenazine producing bacteria in an individual. The method comprises administering to the individual an effective amount of one or more phenazine degrading agents, herein described, alone or in combination with an antibiotic and/or other antimicrobial. In particular, in some embodiments, administering of one or more phenazine degrading agents can be performed in combination with one or more antibiotics and/or other antimicrobials. The system comprises one or more phenazine degrading agents, one or more antibiotics and/or one or more other antimicrobials. In some embodiments of methods and systems, the bacteria comprise persister cells.

According to a fourth aspect, a method and a system for identifying an antimicrobial are described. The method comprises contacting a candidate demethylase protein with a pyocyanin-like phenazine and detecting the ability of the candidate agent to inactivate said pyacianin-like phenazine and/or a phenazine related pathway in the bacteria. The system comprises one or more phenazine producing bacteria able to producing pyocyanin-like phenazine, and one or more agents capable of detecting phenazine and/or phenazine related pathways. In some embodiments of the methods and systems, the bacteria comprise persister cells.

According to a fifth aspect, an antimicrobial is described. The antimicrobial comprises one or more phenazine degrading agents herein described. In particular, the one or more phenazine degrading agents are comprised in the antimicrobial in an amount suitable to reduce antibiotic resistance and/or survivability of phenazine producing bacteria. In some embodiments, the antimicrobial comprises a compatible vehicle, which can be a vehicle for effective administrating and/or delivering of the one or more agents to an individual. In some embodiments of the methods and systems, the bacteria comprise persister cells.

According to a sixth aspect, a composition is described. The composition comprises one or more phenazine degrading agents together with a compatible vehicle. In some embodiments, the composition can comprise one or more phenazine degrading agents and one or more medium components as will be understood by a skilled person.

According to a seven aspect, a method and system for inhibiting bacteria biofilm formation and/or disrupting mature biofilm in a medium is described. The method comprises administering an effective amount of 1-OH-PHZ as metal-chelating agent to the medium comprising the biofilm, alone or in combination with a phenazine degrading agents herein described, an antibiotic and/or other an antimicrobial for a time and under conditions to reduce survivability and/or antibiotic resistance of the bacteria. The system comprises 1-OH-PHZ, one or more phenazine degrading agents herein described, one or more antibiotics and/or one or more other antimicrobials.

The phenazine degrading agents and related antimicrobial compositions, methods and systems herein described, in several embodiments allow reducing antibiotic resistance and/or bacterial survivability according to distinct mechanism and pathways wherein phenazine functions.

The phenazine degrading agents and related antimicrobial compositions, methods and systems herein described can be used in connection with applications wherein reduction of viability of bacteria and/or reduction of antibiotic resistance is desired, which include but are not limited to medical application, drug research, biological analysis and diagnostics including but not limited to clinical applications.

BRIEF DESCRIPTION OF THE DRAWINGS

FIG. 1A shows exemplary photographs of tubes containing PYO before and after the redox reaction indicated (arrows), showing a redox-based change in the shade of grey in the photograph of the reaction mixture of PYO. FIG. 1B shows exemplary chemical structures of exemplary oxidized phenazines discussed herein.

FIGS. 2A-G show chemical structures, charts and pictures illustrating exemplary structures and biochemical analysis of the PodA reaction. PodA catalyzes the demethylation of PYO (FIG. 2A) to reduced 1-OH-PHZ (FIG. 2B). FIG. 2C shows a graph illustrating the results gel filtration chromatography and showing that $PodA_{30-162}$ purifies as a trimer by (45.6 kDa). The inset shows an image of a denaturing gel demonstrating the size of monomeric $PodA_{30-162}$, showing protein bands of PodA trimer sub-units of 10 kDa, 15 kDa and 20 kDa, with PodA trimer band of 45 kDa. Graphs in FIGS. 2D-E show the results of incubations of $PodA_{30-162}$ with PYO and the related conversion of the starting material (FIG. 2D) to 1-OH-PHZ and formaldehyde (FIG. 2E). In the illustrations of FIGS. 2E and 2F, the reported data are average measurements from six reactions and error bars represent one standard deviation around the mean. Formaldehyde is derivatized to facilitate detection; the derivatization competes with other compounds in the mixture so stoichiometric production was not observed. FIG. 2F shows an exemplary photograph of the indicated reaction mixtures, under UV illumination, showing that $PodA_{30-162}$ is active under anoxic conditions, and the PYO containing reaction mixture fluoresces under UV illumination. This fluorescent product has an emission spectrum (250 nm excitation) consistent with a reduced phenazine as shown in the graph in FIG. 2G. While both reduced PYO and 1-OH-PHZ have similar emission maxima (50 µM phenazine), the magnitude of the peak is consistent with the generation of reduced 1-OH-PHZ by $PodA_{30-162}$.

FIGS. 4A-4C shows results supporting the conclusion that $PodA_{30-162}$ activity is minimally inhibited by the presence of glycerol (FIG. 4A) or KCl or NaCl salts (FIGS. 4B-C). FIG. 4D shows exemplary results of PYO demethylation showing that PodA is active over a wide pH range, but loses activity at pH above ~9. Data are from duplicate measurements and data was collected for 5 minutes in a reaction mixture containing 20 µM PYO and 15 nM $PodA_{30-162}$. FIG. 4E shows exemplary results of analysis of $PodA_{30-162}$ reaction rate, V, across a range of PYO concentrations in a reaction containing 15 nM $PodA_{30-162}$. Reaction rates are from data collected during the first 10 seconds after enzyme addition. The detection limit of PYO was 0.5 µM; therefore, PYO concentrations below the $K_m$ of the enzyme were not tested. However, based on the shape of the curve of a best fit to an ideal Michaelis-Menton plot, the apparent $K_m$ is below 1 Data are from three independent protein preparations. Black, grey and white circles represent data from different protein preparations.

FIGS. 7A-C show images of the 1.8 Å crystal structure of $PodA_{30-162}$. FIG. 7A shows an image with a view of the $PodA_{30-162}$ trimer (formed by monomers 1, 2 and 3) with 1-OH-PHZ bound. FIG. 7B shows the solvent-exposed PodA active site that contains charged and polar residues (shown in darker shades of gray in the image). There is a nearby disulfide bridge (see arrow) formed between C88 and C102 ~3.5 Å from 1-OH-PHZ. FIG. 7C shows the solvent accessible surface representation of the bound 1-OH-PHZ in the PodA active site. In the illustration of FIG. 7C the charged and polar residues are shown with darker shades of gray.

FIG. 7E shows a proposed reaction mechanism wherein hydrolysis of the product is spontaneous and occurs after release from the active site.

FIGS. 8A-C shows images of the 1.8 Å crystal structure of $PodA_{30-162}$ illustrated in FIG. 6, also showing electron density maps of the PodA active site and coordinated calcium ion. FIG. 8A shows an image of a Fo-Fc map of the missing density for 1-OH-PHZ before ligand modeling and refinement (contoured at 3.0 sigma). Only the density within 5 Å of the active site residues is shown to highlight the missing ligand density. FIG. 8B shows an image of a zoomed in view of the density around select residues in the active site (2Fo-Fc map, contoured at 1.0 sigma, left panel of FIG. 8B). The anomalous difference map for the entire monomer is shown (contoured at 5.0 sigma), but density is only apparent around a calcium ion located ~16 Å from the bound phenazine (right panel of FIG. 8B). Density for the bound 1-OH-PHZ molecules was apparent in each of the three subunits. Only the active site of the A chain monomer is shown here. There is no apparent density to support the presence of additional cofactors or metal atoms. FIG. 8C shows an image of a zoomed in view of the loop containing the coordinated calcium ion.

FIGS. 9A-D shows charts and picture illustrating results of a molecular analysis of the PodA reaction mechanism. FIG. 9A shows a graph showing results of an exemplary demethylation of PYO and an alternative substrate—methoxy-PMS, inset—over the time interval shown. The graph shows that methoxy-PMS is demethylated by PodA$_{30-162}$, but the reaction rate slows significantly after an initial burst, highlighting the importance of the hydroxyl group of PYO for catalysis and/or driving product release after deprotonation. Data are averages from triplicate measurements and error bars represent one standard deviation from the mean. FIG. 9B shows graphed results of protein mass (kDa) of the indicated PodA mutants analyzed by gel filtration chromatography. Residues in the PodA active site (FIG. 7B) were mutated and the resulting proteins purified; H121A, D68A, E154A, D72N, Y156F and the C88A, C102A (C to A) double mutant all purify as a trimer by gel filtration chromatography. FIG. 9C shows an exemplary SDS-PAGE gel of the gel filtration chromatography-purified PodA mutants indicated, showing that the mutant proteins were pure as assayed by reducing SDS-PAGE. FIG. 9D shows exemplary graphed results of PYO demethylation activity of the indicated mutant PodA proteins over the indicated time interval, which shows that the disulfide bond is not essential for activity. Y156F has ~25% wild type activity, and all other residues appear essential for catalysis.

FIGS. 12A-F show charts and photographs illustrating results of experiments showing that PodA$_{30-162}$ alters phenazines in *P. aeruginosa* culture. PodA$_{30-162}$ alters phenazine concentrations in both TSB medium (as shown in the exemplary graphed results in FIG. 12A) and succinate minimal medium (SMM; as shown in the exemplary graphed results in FIG. 12B). Data are averages from quadruplicate measurements and error bars represent one standard deviation around the mean. bd, below detection (<0.5 µM). FIG. 12C shows exemplary graphed results of total phenazine concentrations in TSB and SSM as summed from panels A and B. While the distribution of phenazines is altered by PodA$_{30-162}$ in TSB, total concentrations remain constant. FIG. 12D shows exemplary photographs of microcentrifuge tubes before (left panel) and after (right panel) incubation of PYO with PodA$_{30-162}$, in presence of precipitated DNA (arrow). The change in appearance of the reaction mixture in the right panel shows that PYO associated with precipitated DNA is not protected from PodA$_{30-162}$. FIG. 12E shows exemplary photographs of microcentrifuge tubes before (left panel) and after (right panel) incubation of PYO with inactivated PodA$_{30-162}$ (arrow), where the absence of change in appearance of the reaction mixture in the right panel shows that inactivated PodA$_{30-162}$ does not demethylate PYO. FIG. 12F shows exemplary graphed results of molarity of PYO under the indicated incubation conditions over the indicated time period, showing that solubilized DNA does not block PodA$_{30-162}$ activity. 200 µM PYO was incubated in the presence or absence of 400 µg mL$^{-1}$ DNA (a stoichiometric excess). While these data do not preclude the possibility that PYO is loosely associated with DNA and may freely dissociate, and PodA may act on this solubilized PYO, they do confirm that DNA does not protect PYO from PodA$_{30-162}$ activity.

FIGS. 13A-H show charts and images showing that that PodA$_{30-162}$ inhibits biofilm formation and anoxic fitness of *P. aeruginosa*. FIG. 13A shows exemplary graphed results of molarity of the phenazines indicated in presence of PodA or PodA-inactive. Phenazines were measured by HPLC in biofilm supernatants after 5 hours of growth. PCA, phenazine-1-carboxylic acid. FIG. 13B shows an exemplary image showing that *P. aeruginosa* forms a robust biofilm in the presence of inactivated PodA$_{30-162}$ after 5 hours. FIG. 13C shows an image illustrating that in the presence of PodA$_{30-162}$, biofilm surface coverage was decreased. Surface coverage was 43.5 percent compared with 82.7 percent in the absence of PodA$_{30-162}$ in the representative images shown. Scale Bars=20 FIG. 13D shows exemplary graphed results of biofilm surface coverage under the indicated conditions, showing that surface coverage was lower in the presence of PodA$_{30-162}$ ($p<10^{-6}$ vs. PodA-inactive, two-tailed Student's t-test). DNase addition decreased surface coverage ($p<10^{-3}$ vs. PodA-inactive), but DNase and PodA$_{30-162}$ combined did not have an additive effect (p>0.05), consistent with an interaction between PYO and eDNA in supporting biofilms (22). Data are averages of 12 replicates taken from independent cultures. Error bars represent one standard deviation around the mean. Δphz, PA14 mutant incapable of making phenazines. FIG. 13E shows an exemplary top down view and FIG. 13F shows an exemplary side view of *P. aeruginosa* grown embedded in 0.5% agar blocks for 27 hours. Scale bars=200 Oxygen depletion occurs at lower depths as a result of biological consumption outpacing diffusion from the surface, resulting in decreased biomass. FIG. 13G shows exemplary graphed results of an oxygen diffusion model predicting the shape of the oxycline in agar blocks. Cell densities were estimated at $10^{8.7}$ cells mL$^{-1}$ based on aggregate number and volume. Modeling this concentration and 2-fold higher and lower densities suggests that oxygen depletion occurs ~300 μm±100 μm below the agar surface. Dashed red line indicates the approximate oxic-anoxic interface. FIG. 13H shows exemplary graphed results of biofilm aggregates detected at 10 μm increments below the agar surface, under the conditions indicated. At depths near the oxic/anoxic interface (dashed red line), total biomass begins to decline. In assays treated for the last 5 hours with PodA$_{30-162}$, there is an apparent biomass defect specifically at anoxic depths compared to untreated and inactive PodA treated controls, consistent with the importance of PYO for anoxic survival in *P. aeruginosa*. Data are averages of six independent experiments and error bars represent one standard deviation around the mean. Open symbols, p<0.01, two-tailed Student's t-test.

FIG. 14A shows exemplary graphed results of a gel filtration plot of purified PodA; an approximate mass ladder is included and suggests PodA is a trimer (~15.2 kDa per subunit). FIG. 14B shows exemplary graphed results of HPLC analysis of PodA reaction substrates (indicated as "starting conditions", upper panel) and products (indicated as "reaction end", lower panel). Formaldehyde (CH$_2$O) was derivatized to 3,5-diacetyl-1,4-dihydrolutidine (DDL) to allow for detection. FIG. 14C shows an exemplary photograph of the indicated reaction mixtures, under UV illumination, showing a visual representation of the PodA reaction under anaerobic conditions. In the reaction tube containing PYO+PodA, UV fluorescence shows the buildup of reduced phenazine in the absence of O$_2$. The excitation-emission spectrum of this product is that of a reduced phenazine.

FIG. 15A shows a phylogenetic tree of PodA-homologous sequences found by BLAST. All sequences were annotated as hypothetical proteins, so organism names are listed. PodA from *M. fortuitum* is indicated with an arrow. Bootstrap values for select branches are shown. FIG. 15B shows structures of the proposed active sites of LSD1 (amine oxidase-like domain, AOL) and PhzM proteins. Structures were rendered using PyMOL software.

FIG. 16A shows a crystal structure of PodA as a trimer (formed by monomers 1, 2 and 3), consistent with biochemical data. FIG. 16B shows the structure of the putative active site of PodA coordinating 1-OH-PHZ The arrowpoints to a disulfide bond formed between C88 and C102. Figures were generated using PyMOL software. Polar and charged residues are shown with darker shades of gray.

FIG. 18A shows 1-hydroxy-Nmethyl acridine. FIG. 18B shows trifluoro pyocyanin. FIG. 18C shows one possible transition state mimic. FIG. 18D shows 4-keto-Nethylphenazine.

FIGS. 20A-C shows charts and images showing that as a result of exemplary experiments, PodA and 1-OH-PHZ inhibit *P. aeruginosa* biofilms. FIG. 20A shows exemplary graphed results showing that PodA (1 μM) and 1-OH-PHZ (100 μM) inhibit biofilm formation compared to an untreated control (Winn et al. (2011) Acta Crystallographica Section D Biological Crystallography 67:235-42). Biofilms were quantified by total DAPI staining and the WT control was set to 100%. FIG. 20B shows exemplary graphed results showing that 1-OH-PHZ elicits a dose dependent response in its ability to inhibit biofilm formation. FIG. 20C shows exemplary images of biofilm formation of WT *P. aeruginosa* in flow cell biofilms. Cells are expressing YFP and form mature biofilms within 5 days.

FIGS. 21A-B show heatmap diagrams of exemplary results of RNASeq analysis of *P. aeruginosa* biofilms exposed to PodA, 1-OH-PHZox, PYO or Fe(II). Data are presented as heatmaps where values represent log(2) changes relative to an untreated control. The heatmaps are converted to grayscale and the relative values are shown in different shades of gray. FIG. 21A shows that 1-OH-PHZox upregulated genes involved in metal scavenging and the starvation response. In particular, the *P. aeruginosa* biofilms exposed to 1-OH-PHZ shows values in a range between 0 and 5; the *P. aeruginosa* biofilms exposed to Fe(II) shows majority of the values in a range between 0 and −5. While the *P. aeruginosa* biofilms exposed to PodA and PYO show positive and negative values close to 0. FIG. 21B shows that both 1-OH-PHZox and PodA upregulate genes including the QapR regulon, that may decrease levels of *Pseudomonas* quinolone signal (PQS), and genes predicted to be involved in drug efflux. In particular, the *P. aeruginosa* biofilms exposed to 1-OH-PHZ and PodA show values in a range between 0 and 5.

FIGS. 23A-B are from reference (9).

FIGS. 24A-C show charts and images illustrating results of exemplary experiments showing that PodA and 1-OH-PHZ inhibit the early stages of P. aeruginosa biofilm formation on succinate minimal medium. FIG. 24A shows images of exemplary 5 hour biofilms treated with 100 μM 1-OHPHZ or 0.5 μg mL-1 of PodA protein. FIG. 24B shows exemplary graphed results of the number of microcolonies (>5 μm across) in each P. aeruginosa biofilm sample grown in presence of PodA, E154A, or 1-OH-PHZ, or in absence of these treatments ('WT'). Numbers are averages and SD from 8 biological replicates. FIG. 24C shows exemplary graphed results showing size distribution of microcolonies from panel B. *=p<0.05, =p<0.01, *=p<0.001 (2-tailed Student's t-test).

FIGS. 28A-B show in some embodiments the optical density of P. aeruginosa biofilm in the presence of 1-OH-PHZ and active PodA compared to inactive E154A mutant PodA.

DETAILED DESCRIPTION

Figure 1A:
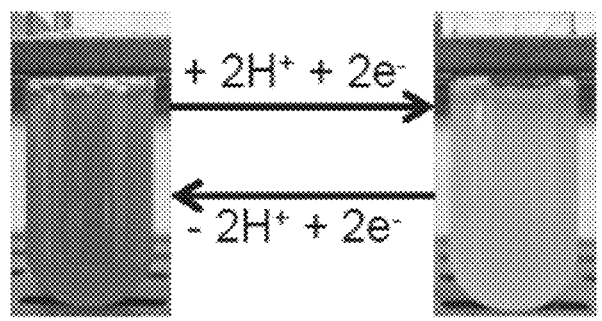
FIGS. 1A-B show redox features and structures of phenazines.
Figure 1B:
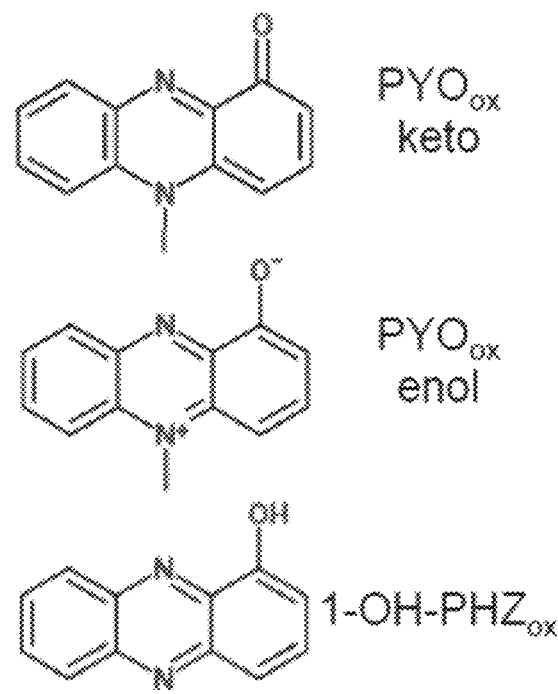

Provided herein are phenazine degrading agents and related compositions, antimicrobials, methods, and systems that can be used to reduce viability of bacteria alone or in combination with one or more antibiotics.

The term "phenazine" as used herein indicates small, colorful, redox-active compounds formed by bacteria to perform diverse physiological functions. In particular, "phenazines" in the sense of the disclosure comprise several phenazines of bacterial origin produced by bacteria such as Pseudomonas spp., Streptomyces spp., Burkholderia spp., and Pantoea agglomerans. The absorption spectra of phenazines are characteristic, with an intense peak in the range 250-290 nm and a weaker peak at 350-400 nm. At least one main band occurs in the visible region (400-600 nm) to which the phenazines owe their colors. Phenazines in the sense of the disclosure comprise compounds of Formula (I):

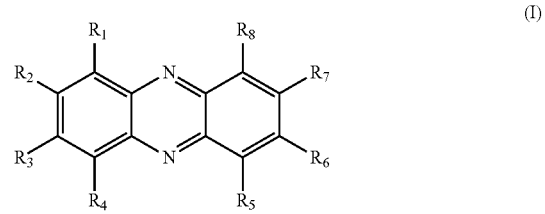

(I)

where $R_1$-$R_8$ are independently selected from hydrogen, hydroxy, alkoxy, alkyl, alkenyl, alkynyl, aryl, heteroaryl, acyl, and other groups identifiable to the skilled person.

Additionally, phenazines can include, but are not limited to, molecules according to the structures and formulas below:

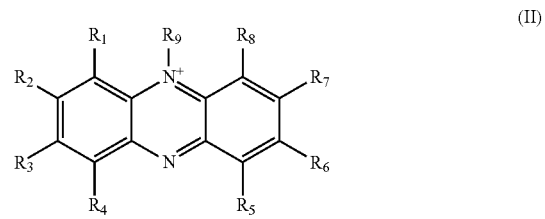

(II)

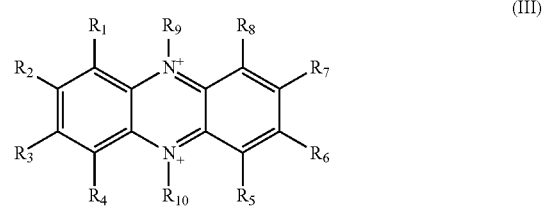

(III)

where $R_1$-$R_{10}$ are independently selected from hydrogen, hydroxy, alkoxy, alkyl, alkenyl, alkynyl, aryl, heteroaryl, acyl, and other groups identifiable to the skilled person, and one of $R_1$-$R_{10}$ is a negatively charged substituent (formal charge of −1) such as

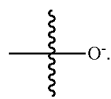

In particular, exemplary phenazine structures comprise:

(1)
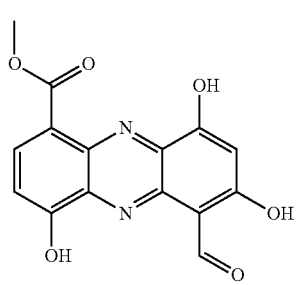

(2)
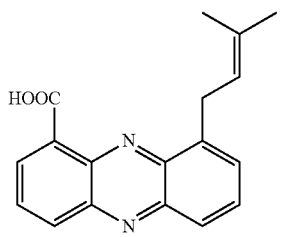

(3)
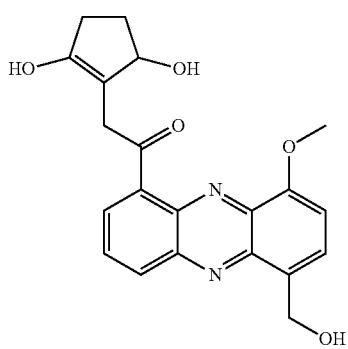

(4)
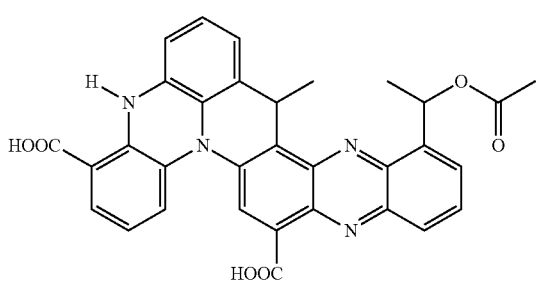

(5)
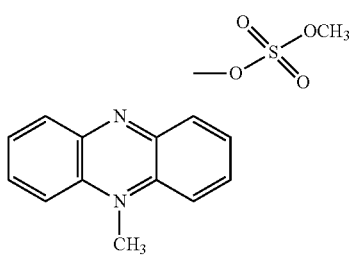

(6)
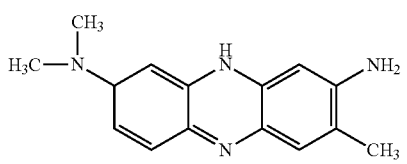

(7)
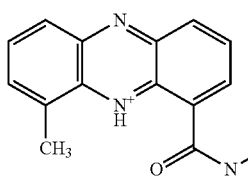

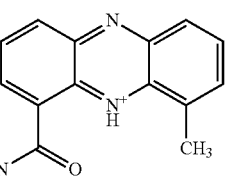

(8)
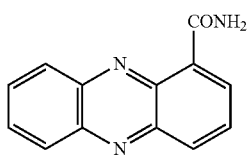

(9)
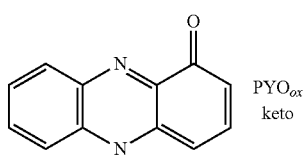

(10)
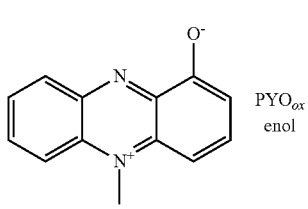

(11)
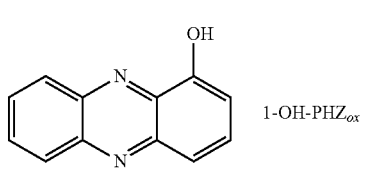

as well as additional phenazines that can be identified by a skilled person such as the exemplary phenazines described in Mentel et al. (ChemBioChem 2009, 10, 2295-2304) and Pierson et al. (Appl Microbiol. Biotechnol. 2010, 86, 1659-1670) and in other references cited in the instant disclosure which are incorporated herein by reference in their entirety Phenazine pigments are mostly water soluble and are excreted into the medium. For example, pyocyanin produced by *Pseudomonas aeruginosa*, diffuses readily into agar-solidified media which become stained blue. Some phenazines are only sparingly water soluble and precipitate. For examples, chlororaphine, a mixture of phenazine-1-carboxamide (oxychlororaphine) and its dihydro derivative, produced by *Pseudomonas chlororaphis*, accumulate as isolated emerald-green crystals at the base of agar slants. Iodinin crystallizes on the surfaces of old colonies of *Brevibacterium iodinum*, giving them a dark-purple appearance, and phenazine-1-carboxylic acid (PCA) is deposited as golden yellow crystals in colonies of *Pseudomonas aureofaciens* and in the surrounding medium. It should be noted, however, that the same pigment can be produced by unrelated bacteria and "achromogenic" strains of many phenazine-producers are common. A number of strains of bacteria produce more than one phenazine. It seems likely that all bacterial phenazines are derived from a common precursor.

Representative phenazines comprise pyocyanin (PYO) and Phenazine-1-carboxylic acid (PCA). Pyocyanin (PYO) is the phenazine characteristically produced by chromogenic strains of the pseudomonad, which is found as the blue pigment occasionally seen on infected wound dressings. More attention has been paid to pyocyanin than to any other phenazine. Pyocyanin is an organic base, blue in alkaline aqueous solutions but red when acidified. The differential solubility of these forms in chloroform and water was exploited for this pigment. Pyocyanin was found to be chemically reduced to a colorless form and spontaneously reoxidized in air, which has led to the discovery, the indicator and redox properties of the compound. Additionally, pyocyanin slowly decomposed to a yellow substance, no longer basic in nature, now known to be 1-hydroxyphenazine.

PCA is a yellow crystalline compound naturally produced by *P. aureofaciens*. The phenazine produced was readily extracted from acidified cultures with chloroform. Dilute alkali changed the color of the phenazine to orange-red and rendered it insoluble in chloroform. PCA isolated from cultures, in amounts of up to 1 g of pigment litre$^{-1}$, was shown to have antibacterial activity towards a number of plant pathogens.

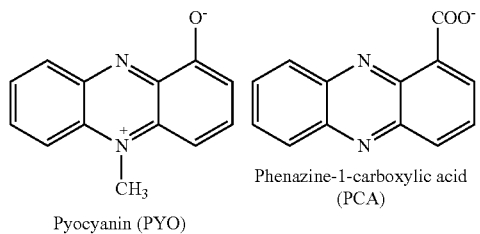

Pyocyanin (PYO)   Phenazine-1-carboxylic acid (PCA)

Biosynthesis as well as properties of individual phenazines are identifiable by a skilled person. In particular, phenazine natural products have been implicated in the virulence and competitive fitness of producing organisms. For example, the phenazine pyocyanin produced by *Pseudomonas aeruginosa* contributes to its ability to colonise the lungs of cystic fibrosis (CF) patients. Production of pyocyanin by *P. aeruginosa* is responsible for the bluish tint of sputum and pus associated with *P. aeruginosa* infections in humans. Clear correlation has been demonstrated between phenazine concentration in sputum and lung function decline. Further, phenazines are found to affect bacterial community development for *P. aeruginosa*.

Similarly, phenazine-1-carboxylic acid, produced by a number of *Pseudomonas* spp., increases survival in soil environments and has been shown to be essential for the biological control activity of certain strains. Examples are provided below for two types of phenazines known as pyocyanin and phenazine-1-carboxylic acid, respectively. For more examples of the occurrence, biochemistry and physiology of phenazine production, see Turner et al., 1986, Advances in Microbial Physiology, vol. 27, page 211-275.

Phenazines targeted by phenazines degrading agents, herein described, comprise in particular pyocyanin-like phenazines which are formed by phenazines of formula (III)

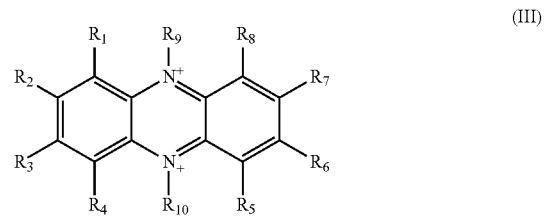

(III)

wherein $R_1$-$R_8$ are independently selected from hydrogen, hydroxy, C1-C4 alkoxy, C1-C4 alkyl, C2-C4 alkenyl, C2-C4 alkynyl, and other groups identifiable to the skilled person, N+—R10 is H and R9 is CH3.

In some embodiments, pyocyanin-like phenazines comprise phenazines of formula III wherein at least one of $R_1$-$R_8$ is hydroxy group. In some embodiments, pyocyanin-like phenazines comprise phenazines of formula (III) wherein at least one of $R_1$-$R_8$ is methoxy group.

In some embodiments, phenazine degrading agents can be naturally produced by a bacterium capable of producing phenazines. In some embodiments, phenazine degrading agents herein described are synthetic phenazine degrading agents including at least one residue or chemical moiety that differs from naturally produced phenazine degrading agents.

In some embodiments, phenazine degrading agents herein described can be produced following modifications of a naturally occurring or other synthetic pyocyanin degrading agent by biochemical approach, a genetic approach and other approaches identifiable by a skilled person. In particular, a biochemical approach to provide a phenazine degrading agents herein described can comprise performing an activity assay following chemical modification of the pyocyanin demethylase, for example based on absorption or fluorescence a phenazine over time and a subsequent purifying of cell fractions to promote a disappearance of phenazine. A genetic approach to provide a phenazine degrading agents herein described can comprise employing transposition mutagenesis of the pyocyanin demethylase to make a collection of random mutants and screening them for an inability to grow on a minimal medium plus the phenazine, as described, for example, in Gallagher et al. (J. Bacteriol. 2002, 184, 6472-6480). Functionality of a modified pyocyanin demethylase can be tested by a biochemical assay where the enzyme is mixed with the substrate pyocyanin. The loss of blue coloration indicates an active pyocyanin demethylase.

In embodiments herein described, the phenazine degrading agents comprises a pyocyanin demethylase or a derivative thereof. The term "pyocyanin demethylase" herein described refers to a type of enzymes having the ability to oxidize a methyl group of pyocyanin-like phenazines of formula (III) to formaldehyde and reduce the pyrazine ring of pyocyanin-like phenazines of formula (III) via an tautomerizing demethylation reaction. The pyocyanin demethylase uses an oxidized phenazine substrate as an electron acceptor with a methyl group to produce a reduced phenazine and formaldehyde. In general, the catalytic site of the pyocyanin demethylase contains several charged and polar residues and a nearby disulfide, also referred to as demethylating residues such as histidine, aspartate, glutamate or tyrosine, as these residues contribute to the demethylase capability of the enzyme. A derivative of a pyocyanin demethylase indicates an enzyme having a) at least 30% identity with the pyocyanin demethylase, and b) at least one demethylating residue in the catalytic site of the derivative pyocyanin demethylase, which is i) the same demethylating residue of the catalytic site of the pyocyanin demethylase or a functional equivalent thereof, and is ii) in a position equivalent to the position of the same demethylating residue of the catalytic site of the pyocyanin demethylase. The derivative of the pyocyanin demethylase to maintain a same, reduced or increased an ability to demethylate pyocyanin as will be understood by a skilled person.

An exemplary demethylation by a pyocinine demethylase is the demethylation of PYO to 1-OH-PHZ$_{re}$ performed by a pyocyanin demethylase herein described. The chemical reaction is shown as follow:

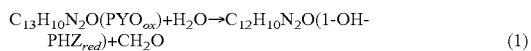

$$C_{13}H_{10}N_2O(PYO_{ox})+H_2O \rightarrow C_{12}H_{10}N_2O(1\text{-}OH\text{-}PHZ_{red})+CH_2O \quad (1)$$

in which oxidized PYO (PYO$_{ox}$) and water are converted to reduced 1-OH-PHZ and formaldehyde. The reduced 1-OH-PHZ can in turn react with Fe(III) generating Fe(II) and oxidized 1-OH-PHZ (1-OH-PHZ$_{ox}$). The oxidized 1-OH-PHZ is also an iron chelator and can chelate Fe(III), Fe(II) as well as other metals. The generation of 1-OH-PHZ will limit the Fe concentration in pathogens such as *P. aeruginosa*, thus interfering with biofilm formation and/or maintenance.

In some embodiments, a pyocyanin demethylase in the sense of the disclosure indicates a protein from *Mycobacterium fortuitum* encoded by MFORT_14352 (NCBI Accession number: EJZ13467) that catalyzes pyocyanin (PYO) degradation (K. C. Costa, M. Bergkessel, S. Saunders, J. Korlach, D. K. Newman, Enzymatic degradation of phenazines can generate energy and protect sensitive organisms from toxicity. *M Bio* 6, e01520-01515 (2015) herein also referred to as PodA (pyocyanin:phenazine oxidoreductase demethylating). In particular, a pyocyanin demethylase in the sense of the disclosure can have sequence

```
                                            (SEQ ID NO: 1)
MTGKTKPAIIGGVAITALAAAGLGVWLFTDGRGGRSTTEPVTMTLDVKN

DQVAKHDFGKPGMDVGDMDIFSDILSVDGKQVGYDGGACFFTNVTPDNP

MTYCELTIHLDAGEIFARSLTPHTLAPFTMAITGGTGEYANSKGELTVS

GVATPDEKYELKLTK
```

A derivative of a pyocyanin demethylase in the sense of the disclosure indicates a variant of a protein that has at least 30% identity with PodA while retaining the ability to demethylate pyocyanin.

The term "percent identity" refers to a quantitative measurement of the similarity between sequences of a polypeptide or a polynucleotide and, in particular, indicates the amount of characters that match between two different sequences. Commonly used similarity searching programs, like BLAST, PSI-BLAST (Altschul S F, M. T., Schäffer AA, Zhang J, Zhang Z, Miller W, Lipman D J., *Gapped BLAST and PSI-BLAST: a new generation of protein database search programs*. Nucleic Acids Res., 1997. 25(17): p. 14), SSEARCH (Smith T F, W. M., *Identification of common molecular subsequences*. J Mol Biol, 1981. 147(1): p. 3, W R, P., Searching protein sequence libraries: comparison of the sensitivity and selectivity of the Smith-Waterman and FASTA algorithms. Genomics, 1991. 11(3): p. 16) FASTA (Pearson W R, L. D., *Improved tools for biological sequence comparison*. Proc Natl Acad Sci USA, 1988. 85(8): p. 5) and the HMMER3 9 (Johnson L S, E. S., Portugaly E, *Hidden Markov model speed heuristic and iterative HMM search procedure*. BMC Bioinformatics, 2010. 11(431): p. 8.) can produce accurate statistical estimates, ensuring that protein sequences that share significant similarity also have similar structures.

The similarity between sequences is typically measured by a process that comprises the steps of aligning the two polypeptide or polynucleotide sequences to form aligned sequences, then detecting the number of matched characters, i.e. characters similar or identical between the two aligned sequences, and calculating the total number of matched characters divided by the total number of aligned characters in each polypeptide or polynucleotide sequence, including gaps. The similarity result is expressed as a percentage of identity.

In some embodiments, PodA derivatives in the sense of the disclosure encompass homologous proteins of PodA with at least 30% identity with PodA of SEQ ID NO:1 and that possesses the demethylating residues at positions equivalent to D72, E154, and Y156 in PodA. In some of those embodiments, a PodA derivative can have a 40% identity, a 50% identity or a 60% identity with PodA of SEQ ID NO:1. In some embodiments, a PodA derivative can have 70% or higher identity with PodA of SEQ ID NO:1. Positions equivalent to the demethylating residues can be identified by first aligning a PodA derivative to SEQ ID NO:1 and then identifying the residues in the PodA derivate that correspond to the demethylating residues of SEQ ID NO:1 in the aligned columns as would be understood to a person skilled in the art.

In some embodiments, a derivative of a pyocyanin demethylase comprise a truncated version the protein encoded by MFORT_14352 (lacking a predicted N-terminal, membrane-spanning helix), hereafter referred to as PodA$_{30\text{-}162}$. The gene expressing PodA$_{30\text{-}162}$ derived from *Mycobacterium* was heterologously expressed in *E. coli*. from *Escherichia coli*. In particular, PodA$_{30\text{-}162}$ in the sense of the disclosure can have sequence

```
                                            (SEQ ID NO: 2)
MDGRGGRSTTEPVTMTLDVKNDQVAKHDFGKPGMDVGDMDIFSDILSVD

GKQVGYDGGACFFTNVTPDNPMTYCELTIHLDAGEIFARSLTPHTLAPF

TMAITGGTGEYANSKGELTVSGVATPDEKYELKLTKAENLYFQ.
```

The PodA derivatives in some embodiments encompass homologous proteins of PodA with at least 30% identity, 40% identity, 50% identity or >70% identity with PodA of SEQ ID NO: 2 while retaining the ability to demethylate pyocyanin.

In some embodiments, derivatives of pyocyanin demethylase comprise homologous proteins of PodA having SEQ ID NO: 1 or SEQ ID NO:2 with at least 30% identity, in which one or more demethylating residues within the enzyme's catalytic site, such as H121, F70, D68, D72, E154 and Y156, are replaced with a functionally equivalent residue.

A functionally equivalent residue of an amino acid used herein typically refers to other amino acid residues having physiochemical and stereochemical characteristics substantially similar to the original amino acid. The physiochemical characteristics include water solubility (hydrophobicity or hydrophilicity), dielectric and electrochemical properties, physiological pH, partial charge of side chains (positive, negative or neutral) and other properties identifiable to a person skilled in the art. The stereochemical characteristics include spatial and conformational arrangement of the amino acids and their chirality. For example, glutamic acid is considered to be a functionally equivalent residue to aspartic acid in the sense of the current disclosure. Tyrosine and tryptophan are considered as functionally equivalent residues to phenylalanine. Arginine and lysine are considered as functionally equivalent residues to histidine.

In particular, the demethylating residue H121 of PodA can be replaced by a protonating residue such as arginine or lysine; D68, D72, E154 or Y156 can be replaced with a negatively charged residue such as aspartate, glutamate or tyrosine; F70 can be replaced by an aromatic residue such as tyrosine or tryptophan.

In some embodiments, a derivative pyocyanin demethylase herein described can be provided using directed evolution from a pyocyanin demethylase or a derivative thereof herein described.

In some embodiments, a pyocyanin demethylase derivative can be provided by protein engineering methods identifiable by those skilled in the art, such as methods based on rational design of modified pyocyanin demethylase derivatives and/or directed evolution techniques. The term "rational design" indicates a process wherein detailed knowledge of the structure and function of a protein is used to make desired changes, employing site-directed mutagenesis and other methods known to those skilled in the art.

In one exemplary embodiment, a derivative pyocyanin demethylase can be designed and generated using computational strategies by introducing mutations to PodA having SEQ ID: NO 1 or SEQ ID: NO 2. The designed pyocyanin demethylase derivatives can potentially possess enhanced stability, higher yield, and comparable or even enhanced catalytic efficiency compared to that of PodA having SEQ ID: NO 1 or SEQ ID: NO 2. Many computational rational design tools can be used for performing such task. For example, automated algorithm based on atomistic Rosetta modeling and phylogenetic sequence information as described in Goldenzweig et. al, Molecular Cell 63, 337-346, 2016 can be used to computationally scan various pyocyanin demethylase variants.

In another exemplary embodiment, the genetic sequence corresponding to the pyocyanin demethylase can be mutated using error-prone PCR or another technique identifiable to the skilled person to produce a library of mutated genetic sequences. The proteins expressed by the mutant sequences can be screened for phenazine degrading activity against specific or broad ranges of phenazines, for example, by the spectrophotometric measurement of phenazine levels over time. The proteins thus identified to be able to degrade a specific phenazine or broad range of phenazines can be synthesized, for example, in a bacterium using recombinant DNA techniques known to the skilled person. The term "directed evolution" indicates a process wherein random mutagenesis is applied to a protein, and a selection regime is used to pick out variants that have one or more desired properties, such as selecting variants with pyocyanin demethylase activity. Directed evolution requires no prior structural knowledge of a protein, nor is it necessary to be able to predict what effect a given mutation will have. Accordingly, the sequence and structure of known pyocyanin demethylases can be modified using protein engineering techniques to provide new pyocyanin demethylase variants.

In some embodiments, a pyocyanin demethylase or a derivative thereof or other phenazine degrading agents herein described, can be obtained from gene expression of an encoding polynucleotide. Polynucleotides encoding pyocyanin demethylase derivatives can be cloned using commercially available reagents from vendors such as Qiagen, Invitrogen, Applied Biosystems, Promega, and others, following standard molecular biology methods known in the art, such as those described in Sambrook and Russell (2001) Molecular Cloning, A Laboratory Manual. Synthetic DNA. Genomic DNA or cDNA encoding pyocyanin demethylase derivatives can be cloned into an expression vector. Expression vectors can comprise plasmid DNA, viral vectors, or non-viral vectors, among others known to those skilled in the art, comprising appropriate regulatory elements such as promoters, enhancers, and post-transcriptional and post-translational regulatory sequences, as would be understood by a skilled person. Promoters can be constitutively active or inducible. RNA can be isolated from a cell, such as *Mycobacterium fortuitum* and cDNA produced by reverse transcription using standard techniques and commercial kits. Alternatively, genomic DNA can be purified from the cell, and cDNA or genomic DNA encoding one or more pyocyanin demethylases isolated, following methods known to those in the art. PCR-based amplification of the gene of interest can be performed using appropriately designed primer pairs (e.g. using PrimerDesign or other programs known to those skilled in the art). An encoded tag can be incorporated into the primer design (e.g. encoding a His-tag designed to be fused to the N- or C-terminus of the recombinant enzyme) to facilitate protein purification (e.g. using commercially-available His-tagged protein purification columns/kits), as described below. PCR-based amplification can be followed by ligation (e.g. using T4 DNA ligase) of the amplicon into an appropriate expression cassette in a plasmid suitable for propagation in bacteria or other cells, such as transformation-competent *E. coli*, followed by growth of transformed cell cultures, purification of the plasmid for confirmation of the cloned pyocyanin demethylase by DNA sequence analysis, among other methods known to those skilled in the art.

Cloned recombinant pyocyanin demethylases can be expressed using cell-based methods, or cell-free methods, following standard techniques and using commercially available kits. Cell-based methods for expression of recombinant enzymes can include expression in prokaryotic or eukaryotic cell cultures, such as *E. coli* or other bacterial cells, yeast strains, insect cells, or mammalian cells, among others known to those skilled in the art.

In some embodiments, the pyocyanin demethylase derivatives in the sense of the disclosure encompass a PodA having a SEQ ID NO: 1 or SEQ ID NO:2 or a derivative thereof, further linked to one or more other proteins, polypeptides, or domains to form a recombinant fusion protein.

Recombinant fusion proteins can be created artificially using recombinant DNA technology identifiable by a person skilled in the art of molecular biology. In general, the methods for producing recombinant fusion proteins comprise removing the stop codon from a cDNA or genomic sequence coding for the PodA protein having a SEQ ID NO: 1 or SEQ ID NO:2 or a derivative thereof, then appending the cDNA or genomic sequence of the second protein in frame through ligation or overlap extension PCR. Optionally, PCR primers can further encode a linker of one or more amino acids residues and/or a PCR primer-encoded protease cleavage site placed between two proteins, polypeptides, or domains or parts thereof. The resulting DNA sequence will then be expressed by a cell or other protein expression system as a single protein. A fusion protein can also comprise a linker of one or more amino acids residues, which can enable the proteins to fold independently and retain functions of the original separate proteins or polypeptides or domains or parts thereof. Linkers in protein or peptide fusions can be engineered with protease cleavage sites that can enable the separation of one or more proteins, polypeptides, domains or parts thereof from the rest of the fusion protein.

In other embodiments, a pyocyanin demethylase fusion protein can be generated using directed evolution approaches such as DNA shuffling and others known to those skilled in the art.

In some embodiments, a pyocyanin demethylase or a derivative thereof can further comprise at least one tag having the ability to tag the pyocyanin demethylase, without affecting the enzyme's ability to degrade phenazine. The tag allows the pyocyanin demethylase to bind to tag-specific antibodies, or other molecules, depending on the tag selection.

The term "tag" as used herein indicates peptide sequences genetically grafted onto a recombinant protein. Tags can be removed by chemical agents or by enzymatic means, such as proteolysis or splicing, as known to a skilled person in the art. Tags can be attached to proteins for various purposes. For example, affinity tags can be appended to proteins so that the tagged protein can be purified from a crude biological source using an affinity technique. Exemplary affinity tags include poly-Histidine (His tag), chitin binding protein (CBP), maltose binding protein (MBP), and glutathione-S-transferase (GST), among others known to those skilled in the art. The poly(His) tag is a commonly used protein tag which binds to metal matrices. Solubilization tags can be used to assist in the proper folding in proteins and keep them from precipitating. Exemplary solubilization tags include thioredoxin (TRX) and poly(NANP). Some affinity tags have a dual role as a solubilization agent, such as MBP, and GST. Chromatography tags can be used to alter chromatographic properties of the protein to afford different resolution across a particular separation technique. Other tags applicable to the current disclosure would be identifiable to a person of ordinary skill in the art.

In some embodiments, a pyocyanin demethylase or a derivative thereof can comprise a His-tag or other tags herein described attached using standard molecular biology techniques known to those skilled in the art. For example, a tag can be added by inserting the polynucleotide encoding a protein of interest in a vector that has the tag configured to fuse at the N-terminus or C-terminus. The tag can also be added using primers encoding the tag then fused to the N-terminus or C-terminus of the gene by PCR. Alternatively or in addition, methods such as overlap extension PCR and infusion HD cloning can be used to insert the tag at a site between the N-terminus and C-terminus of the protein-coding polynucleotide. Optionally, PCR primers can further encode a linker of one or more amino acids residues placed between the protein of interest and the tag to prevent the tag from affecting the activity of the protein being tagged and/or a PCR primer-encoded protease cleavage site. The choice of the location where a tag is inserted to a protein sequence depends mainly on the structural and functional features of the protein and the intended downstream methods employing the use of the tag, as would be understood to a person skilled in the art.

In some embodiments, a tagged pyocyanin demethylase or derivative thereof is PodA of SEQ ID NO: 1 or PodA$_{30-162}$ of SEQ ID NO: 2 further comprising a tag such as a His tag. For example, PodA$_{30-162}$ comprising a C-terminal His tag and a TEV protease cleavage site can facilitate nickel affinity purification of PodA$_{30-162}$. Affinity-purified PodA$_{30-162}$ can be generated by expression in an expression system such as $E.$ $coli$ under control of an expression vector, followed by nickel affinity purification followed by cleavage of the 6×-His tag by TEV protease (see Examples section).

Additional phenazine degrading agents can be identified with methods herein described. The method comprises contacting a candidate demethylase protein with a pyocyanin-like phenazine and detecting the ability of the candidate agent to inactivate said pyacianin-like phenazine and/or a phenazine related pathway in the bacteria. The system comprises one or more phenazine producing bacteria able to produce pyocyanin-like phenazine, and one or more agents capable of detecting phenazine and/or phenazine related pathways. In some embodiments of the methods and systems, the bacteria comprise persister cells.

The terms "detect" or "detection" as used herein indicates the determination of the existence, presence, or fact of a target in a limited portion of space, including but not limited to a sample, a reaction mixture, a molecular complex and a substrate. The "detect" or "detection" as used herein can comprise determination of chemical and/or biological properties of the target, including but not limited to ability to interact, and in particular bind, other compounds, ability to activate another compound and additional properties identifiable by a skilled person upon reading of the present disclosure. The detection can be quantitative or qualitative. A detection is "quantitative" when it refers, relates to, or involves the measurement of quantity or amount of the target or signal (also referred to as quantitation), which includes but is not limited to any analysis designed to determine the amounts or proportions of the target or signal. A detection is "qualitative" when it refers, relates to, or involves identification of a quality or kind of the target or signal in terms of relative abundance to another target or signal, which is not quantified.

In some embodiments, activity of phenazine degrading agents herein described can be detected by detecting difference in the amount of phenazine in bacteria before and after administration of the phenazine degrading agents herein described. The amount of phenazine in the bacteria before and after reduction of the quantity of phenazine according to the methods described herein can be measured by methods identifiable to a skilled person upon reading of the present disclosure. For example, the quantity of phenazine in bacterial culture before and after reduction of the quantity of phenazine can be measured by directly loading the filtrate of the culture onto a HPLC column and analyzing the filtrate as done by Dietrich et al. (Molecular Microbiology 2006, 61, 1308-1321). Additional quantification techniques can be identified by a skilled person and can include, for example, using time-lapsed spectral multiphoton fluorescence microscopy of Sullivan et al., (ACS Chemical Biology 2011, 6, 893-899,) to monitor phenazine concentrations within bacterial cells in vivo both before and after reduction of the phenazine levels.

In some embodiments, one or more phenazine degrading agents herein described can be used in methods and systems to interfere with viability of bacteria.

The term "bacterium" or "bacteria" as used herein refers to a prokaryotic microbial species of Gram-negative or Gram positive bacteria. The wording "Gram-negative bacteria" refers to bacteria that do not retain crystal violet dye in the Gram staining protocol. In contrast, the wording "Gram-positive bacteria" refers to those that are stained dark blue or violet by Gram staining. Exemplary bacteria in the sense of the disclosure comprise Pseudomonas, Brevibacterium, Coryneform Bacteria, Nocardia Brevibacterium linens, Brevibacterium, Burkholderia cenocepecia, Methanosarcina mazei, Mycobacterium abscessus, Pantoea agglomerans, Pectobacterium atrosepticum, Pelagio variabilis, Pseudomonas fluorescens, Streptomyces anulatus, Streptomyces cinnamonensis, and related species that produce phenazines to facilitate various physiological functions identifiable to a skilled person upon reading of the present disclosure.

In particular, in several embodiments, herein described, bacteria in the sense of the disclosure comprise phenazine producing bacteria, which comprise Pseudomonas aeruginosa and additional bacteria known or identifiable by a skilled person, and phenazine degrading bacteria which comprise Sphingomonas sp. DP58 (see Yang et al. Current Microbiology 2007, 55, 284-287 and Chen et al. Biodegradation 2008, 19, 659-667) and additional bacteria known or identifiable by a skilled person.

Identification of a phenazine degrading bacterium can be performed by various techniques. For example, identification of a phenazine producing bacterium can be performed by constructing a bacterial "enrichment culture" by defining a minimal growth medium where a phenazine (PCA, PYO, and additional phenazines identifiable by a skilled person) is provided as either (or both) the sole source of carbon or nitrogen. If growth is observed after many rounds of serial dilutions, phenazine-degraders can be isolated by plating the enrichment culture on an agar plate with the same medium composition or by dilution to extinction in liquid medium. Single colonies are picked, and streaked to fresh plates, and visually checked for purity. Once pure, the 16S rDNA is sequenced and the organism can be phenotypically characterized. Other methods for identifying a bacterium capable of phenazine degradation would be identifiable to a skilled person upon reading of the present disclosure.

In some embodiments, bacteria comprise persister cells which typically constitute a small portion of a culture which is tolerant to killing by lethal doses of bactericidal antibiotics. Persister bacterial cells can be identified, for example, by exposure of logarithmic or stationary cultures of the bacteria to antibiotics using concentrations exceeding five times the minimum inhibitory concentration for each antibiotic. Persister numbers can be determined by plating the antibiotic-treated cultures on LB agar plates and subsequent counting of colony forming units representing the cell numbers which survived antibiotic exposure. Other methods for identification of persister cells will be known by a skilled person, and can be found, for example, in Möker et al. ("*Pseudomonas aeruginosa* increases formation of multidrug-tolerant persister cells in response to quorum-sensing signaling molecules." In J Bacteriol. 2010 April; 192(7): 1946-55. Epub 2010 Jan. 22).

In some embodiments, one or more phenazine degrading agents herein described can be used in methods and systems for the inactivation of phenazines and/or a phenazine related pathway.

The term "inactivation" as used herein with reference to a pathway refers to a complete or partial inhibition of one or more of the reactions or steps in the pathway.

The terms "inhibit" and "inhibition" as used herein refers to a decrease relative to a baseline level. Accordingly, inhibition of a reaction indicates a decrease in the relative output compared to an output selected as a baseline level. Inhibition of a reaction can be detected by detecting any products or other indicator and/or parameter associated with completion of the reaction and identifiable by a skilled person. Accordingly, an inactivated pathway in the sense of the present disclosure indicates a pathway in which any enzyme controlling a reaction in the pathway is biologically inactive or in which at least one of the reactions or steps of the pathway is otherwise inhibited, e.g. by degrading one or more enzymes of the pathway and/or by subtracting the relevant substrate and/or intermediate through phenazine degradation.

The term "pathway" as used herein refers to a biological process comprising one or more chemical or biological reactions or steps in which at least one substance is transformed, produced, and/or acquired by a bacterium. The one or more reactions or steps comprised in the pathway can involve molecules such as, for example, proteins, enzymes, cofactors, oxidizing/reducing agents, signaling molecules, metal ions, and others identifiable to a skilled person upon reading of the present disclosure that participate in the transformation, production and/or acquisition of the substance by a bacterium. In embodiments wherein pathway involves a bacterial cell signaling molecule, the pathway indicates signal transduction through cascade reactions of a series of signaling molecules as part of a complex system of communication that governs basic cellular activities and coordinates cell actions. Exemplary pathways of the disclosure comprise Fe(III) reduction to Fe(II) comprising the steps of reduction of Fe(III) to Fe(II) through the use of a reducing agent (such as, for example, pyocyanin, and/or other reducing agents), bacterial acquisition of Fe(II) comprising the steps of reduction of Fe(III) to Fe(II) by a reducing agent (such as, for example, pyocyanin, and/or other reducing agents) and importation of Fe(II) into the bacteria by a transporter protein (such as, for example, FeoB), and other pathways identifiable to a skilled person upon reading of the present disclosure.

The term "phenazine-related pathway" as used herein refers to either a pathway in which a phenazine is a starting material, intermediate, or product, or alternatively, any pathway in which at least one of the one or more of the steps comprised in the pathway are mediated by a phenazine. Exemplary pathways in which a phenazine is a starting material, intermediate, or product include, but are not limited to, phenazine biosynthesis, phenazine cycling, quorum sensing, and other pathways identifiable to a skilled person upon reading of the present disclosure. Exemplary pathways in which one or more of the steps of the pathway are promoted or mediated by a phenazine include, but are not limited to, reduction of Fe(III) to Fe(II) by phenazine, bacterial Fe(II) acquisition in which the Fe(II) is obtained, and other processes identifiable to a skilled person upon reading of the present disclosure.

In some embodiments, phenazine related pathways comprise phenazine-mediated bacterial biofilm formation, phenazine-mediated iron acquisition and phenazine mediated intracellular redox balancing of bacteria In some embodiments, a phenazine related pathway comprises a phenazine-mediated signaling pathway of the bacteria. Specifically, in some embodiments, the bacteria have a motile and a sessile state and the signaling pathway triggers a transition from the motile to the sessile state.

In some embodiments, one or more phenazine related pathways comprise central metabolic pathways of the bacteria.

In some embodiments, the one or more phenazine related pathways comprise transportation of phenazines in and/or out of the bacterial cell. In other embodiments, phenazine related pathways comprise intracellular phenazine mediated redox hemostasis of the bacteria.

In some embodiments, a method and system to interfere with viability of bacteria is described, the method comprising contacting bacteria with one or more phenazine degrading agents herein described to reduce survivability and/or antibiotic resistance of the bacteria.

The term "viability" as used here in refers to whether or not a bacterial cell is able to maintain itself or recover its potentiality. Viable cells in the sense of the present disclosure are cells able to, or capable of recover the ability to form colonies and biofilms on or in a solid or liquid medium. In some embodiments, the term "medium" as used herein indicates an environment that is suitable to support growth of microorganisms or cells. In particular, suitable medium comprise growth medium or culture medium in a liquid or gel designed to support the bacteria in vitro, as well as tissues and other suitable environments within a host (including a human host) in vivo. Accordingly, various mediums are formed by or comprise medium components that are chemical compounds and molecules that are used in life-supporting functions and processes of bacteria, which allow bacterial cells to grow and reproduce.

Exemplary medium components comprise at least one redox-active compound in a solvent. In some embodiments, the solvent can comprise water in at least 10% by volume, preferably at least 50% by volume, and most preferably at least 95% by volume.

In some embodiments, the medium solvent can further comprise at least one organic solvent. Exemplary organic solvent includes ethanol, methanol, tetrahydrofuran, dimethylformamide (DMF), dimethyl sulfoxide (DMSO), acetic acid, formic acid, glycerol, glycol, isopropanol and 1-butanol.

In some embodiments, the redox-active compound has at least one oxidation absorption maximum in the wavelength of 400 nm to 700 nm in the oxidized state with a corresponding oxidation extinction coefficient. In some embodiments, the redox-active compound has at least one reduction absorption maximum in the wavelength of 400 nm to 700 nm in the reduced state with a corresponding reduction extinction coefficient.

In some embodiments, the at least one oxidation absorption maximum and the at least one reduction absorption maximum have an absorption shift or difference of at least 5 nm, preferably 50 nm and most preferably 150 nm.

In some embodiments, the ratio of oxidation extinction coefficient to the reduction extinction coefficient is at least 2 to 1, preferably at least 20:1 and most preferably 100:1.

In some embodiments, the ratio of reduction extinction coefficient to the oxidation extinction coefficient is at least 2 to 1, preferably at least 20:1 and most preferably 100:1.

In some embodiments, the at least one redox-active compound has a standard electrode potential E° vs. NHE of −500 mV to 500 mV. As used herein, the term redox-active compound refers to a chemical compound that is able to undergo reversible electrochemical conversion between an oxidation state and reduction state. A redox-active compound includes naturally occurring redox-active molecules, organic, inorganic or metal ion complexes. Redox-active natural products include, but are not limited to those produced by the genera *Streptomyces* and *Pseudomonas*, including those redox-active natural products produced by *P. aeruginosa*, *P. oryzihabitans*, and *P. luteola*.

Exemplary redox-active compounds listed in Table 1.

TABLE 1

Exemplary redox-active compounds

| Chemical name (Abbreviation) | Structure (The oxidized form) | E°, (vs. NHE) (mV) | # of Redox cycles over 7 days | Support survival? | Reduction by PA14? |
|---|---|---|---|---|---|
| Pyocyanin (PYO) | 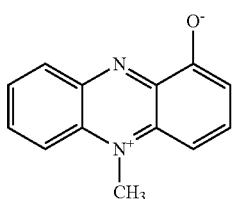 | −40[a] | 31 | Yes | Yes |
| Phenazine-1-carboxylate (PCA) | 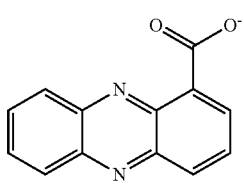 [SMILES: O=C([O-])c1cccc2nc3ccccc3nc12] | −114[a] | 22 | Yes | Yes |

TABLE 1-continued

Exemplary redox-active compounds

| Chemical name (Abbreviation) | Structure (The oxidized form) | $E^{0,}$ (vs. NHE) (mV) | # of Redox cycles over 7 days | Support survival? | Reduction by PA14? |
|---|---|---|---|---|---|
| 1-Hydroxyphenazine (1-OHPHZ) | | $-174^a$ | 14 | Yes | Yes |
| Methylene blue (MB) | | $0^b$ ($+11^c$) | 3 | No | Yes |
| 2,6-AQDS | | $-184^d$ | No cycle | No | Yes (very slowly) |
| Paraquat | | $-446^e$ | No cycle | No | No |
| Homogentisic acid (HMA) | | $+306^b$ | No cycle | No | — |

[a] Reference (Wang, Y., and D. K. Newman. 2008. Redox reactions of phenazine antibiotics with ferric (hydr)oxides and molecular oxygen. Environmental Science & Technology 42: 2380-2386)
[b] $E^{0,}$ values were measured in aqueous solution at pH 7 in this study
[c] Reference (Fultz, M. L., and R. A. Durst. 1982. Mediator Compounds for the Electrochemical Study of Biological Redox Systems-a Compilation. Analytica Chimica Acta 140: 1-18)
[d] Reference (Hernandez, M. E., and D. K. Newman. 2001. Extracellular electron transfer. Cellular and Molecular Life Sciences 58: 1562-1571)
[e] References (Michaelis, L., and E. S. Hill. 1933. Potentiometric Studies On Semiquinones. Journal of the American Chemical Society 55: 1481-1494, Michaelis, L., and E. S. Hill. 1933. The Viologen Indicators. The Journal Of General Physiology 16: 859-873)

Additional medium components that can be found in a medium comprise amino acids. salts, polyacrylic acids, polyols, polyglycols, such as Polyethelene Glycols (e.g. PEG 1000, PEG 3000), polysaccharides, polypeptides, polynucleotides as well as other organic polymers with molecular weight between 10,000 to 1,000,000 Da and additional components identifiable by a skilled person. For example medium components can comprise sodium thioglycolate ($HS-CH_2CO_2Na$), sodium dithionite, Organic; simple sugars e.g. glucose, acetate or pyruvate; extracts such as peptone, tryptone, yeast extract etc., hydrogen carbonate salts ($HCO_3^-$), amino acids, $NH_4Cl$, $(NH_4)_2SO_4$, $KNO_3$, $KCl$, $K_2HPO_4$, $MgCl_2$, $MgSO_4$, $CaCl_2$, $Ca(HCO_3)_2$, $FeCl_3$, $Fe(NH_4)(SO_4)_2$, Fe-chelates, $CoCl_2$, $ZnCl_2$, $Na_2MoO_4$, $CuCl_2$, $MnSO_4$, $NiCl_2$, $Na_2SeO_4$, $Na_2WO_4$, $Na_2VO_4$, Vitamins, amino acids, purines, pyrimidines Methods for evaluating the viability of bacteria after the use of the methods and systems for interference with viability of bacteria described herein include, but are not limited to, measurement of colony forming units, cell counts such as that described by Wang et al. (J. Bacteriol. 2010, 192, 365-369), and other methods identifiable to a skilled person upon the reading of the present disclosure.

In some embodiments, phenazine degrading agents, herein described, can be administered to enhance phenazine degradation endogenously and/or exogenously.

In particular, in some embodiments, enhancing phenazine degradation can be performed by expressing and/or delivering to the bacteria one or more phenazine degrading agents herein described. In an exemplary embodiment, a DNA sequence of a phenazine-degrading agent can be delivered by introduction of the DNA sequence into a bacterium via a vector (e.g. viral or plasmid vector), or other techniques identifiable by a skilled person upon reading of the present disclosure, and the DNA sequence expressed in the bacteria to produce the phenazine-degrading protein. In another embodiment, phenazine-degrading proteins can be expressed in other bacteria and then isolated and purified to afford phenazine-degrading proteins suitable for extracellular degradation of phenazine.

In some embodiments, inactivating a phenazine or phenazine-related pathway comprises contacting the bacteria with one or more phenazine degrading agents to impair phenazine-mediated bacterial biofilm development in the bacteria.

As used herein the term "biofilm" indicates an aggregate of microorganisms in which cells adhere to each other on a surface. These adherent cells are frequently embedded within a self-produced matrix of extracellular polymeric substance (EPS). Biofilms can form on living or non-living surfaces and can be prevalent in natural, industrial and hospital settings. The microbial cells growing in a biofilm are physiologically distinct from planktonic cells of the same organism, which, by contrast, are single-cells that can float or swim in a liquid medium. Formation of a biofilm begins with the attachment of free-floating microorganisms to a surface. These first colonists adhere to the surface initially through weak, reversible adhesion via van der Waals forces. If the colonists are not immediately separated from the surface, they can anchor themselves more permanently using cell adhesion structures such as pili. When the biofilm growth is balanced with that of biofilm dispersion, the biofilm is considered "mature." Methods to quantify and measure biofilms will be known to a skilled person and can include, for example, the COMSTAT method of Heydorn et al. (Microbiology 2000, 146, 2395-2407).

In some embodiments, the phenazine-mediated bacterial biofilm development comprises phenazine-mediated iron acquisition of bacteria. Iron has been shown to be involved as a signal in bacterial biofilm formation (see, for example, Banin et al. PNAS, 2005, 102, 11076-11081). Phenazines have been shown to mediate iron acquisition in bacterial biofilm development, for example, by reduction of insoluble Fe(III) to more soluble Fe(II) (See, for example, Wang et al. J. Bacteriol. 2011, 193, 3606-3617).

In some embodiments, one or more phenazine degrading agents herein described can be used to inhibit pathogenic microbial biofilm formation as well as to disrupt mature biofilm in vitro and in vivo (see Examples 5 and 7).

In particular, in some embodiments, herein described phenazine degrading agents herein described can impact early stages in biofilm formation and development by decreasing the biofilm surface coverage. In one exemplary embodiment, the biofilm surface coverage was 43.5 percent in the presence of $PodA_{30-162}$ compared with 82.7 percent in the absence of $PodA_{30-162}$ (FIGS. 13C-D).

Figure 13E:
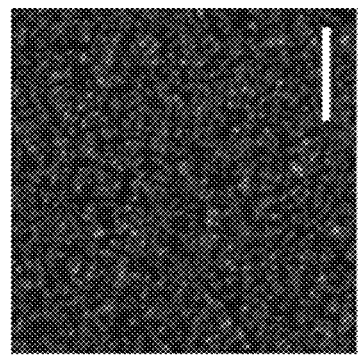

In some embodiments, phenazine degrading agents herein described can disrupt the mature biofilm by interfering with anoxic growth of pathogens in deeper layers of the biofilm. In one exemplary embodiment, biofilms cultures treated with $PodA_{30-162}$ shows a sharper decline in detectable aggregates ~0.300 um and deeper below the agar surface (FIGS. 13G-H).

A person skilled in the art would understand that as biofilm matures, cells in deeper layers of the biofilm begin to experience oxygen limitation and redox stress, rendering the cells to be slow growing and highly resistant to antibiotics.

Thus, in some embodiments, a method for inhibiting bacteria biofilm formation and/or disrupting mature biofilm in a medium is described, the method comprising administering one or more phenazine degrading agents to the medium comprising the biofilm. The suitable medium comprises growth medium or culture medium in a liquid or gel designed to support the bacteria in vitro, as well as tissues and other suitable environments within a host (including a human host) in vivo.

The phenazine degrading agents such as PodA and a derivative thereof can degrade pyocyanin-like phenazines into 1-Hydroxyphenazine (1-OH-PHZ) which can limit the Fe concentration in pathogens such as *P. aeruginosa* by acting as an iron chelator, thus interfering with biofilm formation and/or maintenance (see Example 7).

Thus, in some embodiments, another method for inhibiting bacteria biofilm formation and/or disrupting mature biofilm in a medium is described. The method comprises administering 1-hydroxyphenazine (1-OH-PHZ) as metal-chelating agent to the medium comprising the biofilm, alone or in combination with an antibiotic and/or other antimicrobial for a time and under conditions to reduce survivability and/or antibiotic resistance of the bacteria.

The term "chelator" or "chelating agent" as used herein refers to a molecule or ligand capable of binding a metal ion (e.g. iron) by forming multiple bonds to the metal. In particular, chelation involves the formation or presence of two or more separate coordinate bonds between a polydentate (multiple bonded) ligand and a single central metal. These ligands can be organic compounds, and are called chelants, chelators, chelating agents, or sequestering agents. Chelators can be molecules made by the host (such as, hemoglobin, transferrin, lactoferrin, conalbumin and ferritin); or molecules made by other microorganisms (such as siderophores including Enterobactin, Yersiniabactin, Pyoverdine, Pyochelin, and others identifiable to a skilled person.); or synthetic molecules (e.g. deferoxamine, deferiprone, deferasirox, 2,2 dipyridyl, 1,10 phenanthroline, FerroZine, EDTA, diethylenetriamine, ethylene diamine, N,N', N''-tris(2-pyridylmethyl)-1,3,5-cis,cis-triaminocyclohexane (tachpyr), and others identifiable to a skilled person).

In general, a metal chelator is a molecule capable of binding a metal and forming a molecular complex according to the generic reaction:

$$mM + lL + hH^+ = M_mL_lH_h \qquad (2)$$

wherein M is the metal, L is the chelator, and H$^+$ is positive hydrogen ions with m, l and h independently equal to or higher than 1, and wherein the equilibrium constant βmlh is determined to be

$$\beta mlh(M, L) = \frac{[M_mL_lH_h]}{[M]^m[L]^l[H^+]^h} \qquad (3)$$

Some molecules are capable of binding more than one metal with different binding affinities which are reflected in different equilibrium constant βmlh. In those instances, a molecule is known to a skilled person as a chelator of a particular metal when the molecule is capable of specifically binding that metal. Specific binding of a metal by a chelator is determined by the molecule binding with a highest equilibrium constant βmlh for the metal separately calculated with respect to other metals according to equation (3).

For example, some molecules capable of binding more than one metal. To determine whether a molecule is a Cu or Zn chelator, the equilibrium constant βmlh can be calculated for the molecule with respect to Cu, with respect to Zn and with respect to other metals. The calculated βmlh values can be compared to determine whether the molecule is a Cu) or Zn chelator.

Figure 27A:
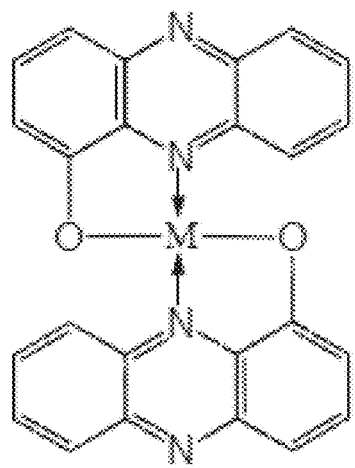
FIG. 27A shows a coordination geometry for 1-OH-PHZ metal complexation.

1-hydroxyphenazine (1-OH-PHZ) in the sense of the present disclosure is a metal chelating agent. FIG. 27A illustrates a coordination geometry for 1-OH-PHZ metal complexation. 1-OH-PHZ can act as a bivalent metal chelator by forming a stable five-membered, 2:1 chelate compound. For example, 1-OH-PHZ can form metal complexes with bivalent metals such as Cu, Ni, Co, Zn and Cd (Kidani Y. Studies on Metal Chelate Compounds of Phenazine Derivatives. VIII. Metal Complexes of 1-Hydroxyphenazine, Yakugaku Zasshi. 1973 September; 93(9):1089-93.). The dissociation constant of 1-hydroxyphenazine with metals can be calculated according to equation 3 or determined by spectrophotometry or potentiometry as will be understood by a person skilled in the art. For example, in one exemplary embodiment, 1-hydroxyphenazine (1-OH-PHZ) as a copper chelating agent has a log of the equilibrium constant βmlh of binding copper equal to 8.68. (Kidani Y., Studies on Metal Chelate Compounds of Phenazine Derivatives. I. Spectrophotometric Studies on Copper Chelate Compounds of 1-Hydroxyphenazine and its Di-N-oxide. Chemical and Pharmaceutical Bulletin, Vol. 6 (1958) No. 5, P 556-562))

In some embodiments, phenazine degrading agents can be used in methods for treating and/or preventing a bacterial infection by a phenazine producing bacteria in an individual.

The term "treatment" as used herein indicates any activity that is part of a medical care for, or deals with, a condition, medically or surgically.

The term "prevention" as used herein indicates any activity which reduces the burden of mortality or morbidity from a condition in an individual. This takes place at primary, secondary and tertiary prevention levels, wherein: a) primary prevention avoids the development of a disease; b) secondary prevention activities are aimed at early disease treatment, thereby increasing opportunities for interventions to prevent progression of the disease and emergence of symptoms; and c) tertiary prevention reduces the negative impact of an already established disease by restoring function and reducing disease-related complications.

The term "condition" as used herein indicates a physical status of the body of an individual (as a whole or as one or more of its parts), that does not conform to a standard physical status associated with a state of complete physical, mental and social well-being for the individual. Conditions herein described include but are not limited to disorders and diseases wherein the term "disorder" indicates a condition of the living individual that is associated to a functional abnormality of the body or of any of its parts, and the term "disease" indicates a condition of the living individual that impairs normal functioning of the body or of any of its parts and is typically manifested by distinguishing signs and symptoms.

The term "individual" as used herein in the context of treatment includes a single biological organism, including but not limited to, animals and in particular higher animals and in particular vertebrates such as mammals and in particular human beings.

In some embodiments, the method for treating and/or preventing a bacterial infection in an individual comprises administering to the individual an effective amount of one or more phenazine degrading agents herein described alone or in combination with an antibiotic and/or other antimicrobial. In some embodiments, administering of one or more phenazine degrading agents can be performed in combination with one or more antibiotics and/or other antimicrobials. In particular, the phenazine degrading agents, herein described, will be selected by the skilled person as not interfering in a deleterious manner with the normal biochemical pathways of the individual.

Exemplary antibiotics that can be used in combination with the one or more phenazine degrading agents herein described include Amoxicillin and clavulanic acid (Augmentin®), Methicillin, oxacillin, nafcillin, cloxacillin, dicloxacillin, carbenicillin, ticarcillin, piperacillin, mezlocillin, azlocillin, ticarcillin and clavulanic acid (Timentin®), piperacillin and tazobactam (Zosyn®), cephalexin, cefdinir, cefprozil, cefaclor, cefuroxime, sulfisoxazole, erythromycin/sulfisoxazole, tobramycin, amikacin, gentamicin, erythromycin, clarithromycin, azithromycin, tetracycline, doxycycline, minocycline, tigecycline, ciprofloxacin, levofloxacin, vancomycin, linezolid, imipenem, meripenem, and aztreonam. As a person of ordinary skill in the art would understand, the antibiotics herein listed can be selected for treating infections or reducing inflammation caused by bacteria including *Staphylococcus aureus, Pseudomonas* (*P. aeruginosa*), *Burkholderia cepacian*, some mycobacteria.

The administering to the individual the one or more phenazine degrading agents alone or in combination with an antibiotic and/or other antimicrobial can be performed through various administration routes including oral ingestion, inhalation, intranasal, topical application, intravenous or subcutaneous injections and others as will be recognized by a person skilled in the art. The one or more phenazine degrading agents alone or in combination with an antibiotic and/or other antimicrobial can be in a form of an aqueous solution, cream, solid powder, tablets, aerosols, or other forms as will be understood by a person skilled in the art.

In some embodiments, an antimicrobial is described. The antimicrobial comprises one or more phenazine degrading agents herein described. The one or more phenazine degrading agents are in particular comprised in the antimicrobial in an amount suitable to reduce antibiotic resistance and/or survivability of phenazine producing bacteria. In some embodiments, the antimicrobial comprises a compatible vehicle, which can be a vehicle for effective administrating and/or delivering of the one or more agents to an individual. In some embodiments of the methods and systems, the bacteria comprise persister cells.

An "antimicrobial" as described herein indicates a substance that kills or inhibits the growth of microorganisms such as bacteria, fungi, or protozoans. Antimicrobial either kills microbes (microbiocidal) or prevent the growth of microbes (microbiostatic).

In some embodiments, the antimicrobial comprises one or more phenazine degrading agents optionally a compatible vehicle for effective administrating and/or delivering of the one or more agents to an individual.

The term "vehicle" as used herein indicates any of various media acting usually as solvents, carriers, binders or diluents for phenazine degrading agents comprised in the composition as an active ingredient.

In some embodiments, antimicrobial is a pharmaceutical composition comprising one or more phenazine degrading agents for the treatment of cystic fibrosis and a pharmaceutically acceptable vehicle such as an excipient or diluent.

The term "excipient" as used herein indicates an inactive substance used as a carrier for the active ingredients of a medication. Suitable excipients for the pharmaceutical compositions herein disclosed include any substance that enhances the ability of the body of an individual to absorb the one or more agents. Suitable excipients also include any substance that can be used to bulk up formulations with the one or more agents to allow for convenient and accurate dosage. In addition to their use in the single-dosage quantity, excipients can be used in the manufacturing process to aid in the handling of the one or more agents. Depending on the route of administration, and form of medication, different excipients may be used. Exemplary excipients include but are not limited to anti-adherents, binders, coatings disintegrants, fillers, flavors (such as sweeteners) and colors, glidants, lubricants, preservatives, or sorbents.

The term "diluent" as used herein indicates a diluting agent which is issued to dilute or carry an active ingredient of a composition. Suitable diluents include any substance that can decrease the viscosity of a medicinal preparation.

In particular, in some embodiments, the phenazine degrading agents herein described can be included in pharmaceutical compositions which contain at least one phenazine degrading agents herein described, in combination with one or more compatible and pharmaceutically acceptable vehicles, and in particular with pharmaceutically acceptable diluents or excipients. In those pharmaceutical compositions, the phenazine degrading agents can be administered as an active ingredient for treatment or prevention of a condition in an individual.

In some embodiments, the antimicrobial or pharmaceutical composition comprising one or more phenazine degrading agents herein described further comprises antibiotic and/or an additional antimicrobial.

The term "antibiotics" as used herein refers to a type of antimicrobial used in the treatment and prevention of bacterial infection. Some antibiotics can either kill or inhibit the growth of bacteria. Others can be effective against fungi and protozoans. The term "antibiotics" can be used to refer to any substance used against microbes. Antibiotics are commonly classified based on their mechanism of action, chemical structure, or spectrum of activity. Most antibiotics target bacterial functions or growth processes. Antibiotics having bactericidal activities target the bacterial cell wall, such as penicillins and cephalosporins, or target the cell membrane, such as polymyxins, or interfere with essential bacterial enzymes, such as rifamycins, lipiarmycins, quinolones and sulfonamides. Antibiotics having bacteriostatic properties target protein synthesis, such as macrolides, lincosamides and tetracyclines. Antibiotics can be further categorized based on their target specificity. "Narrow-spectrum" antibacterial antibiotics target specific types of bacteria, such as Gram-negative or Gram-positive bacteria. "Broad-spectrum" antibiotics affect a wide range of bacteria.

In some embodiments, suitable antibiotics that can be used in the antimicrobial in combination with Fe chelators include ampicillin, kanamycin, ofloxacin, Aminoglycosides, Carbapenems, Ceftazidime, Cefepime, Ceftobiprole, Fluoroquinolones, Piperacillin, Ticarcillin, tobramycin, aztreonam, coliston, tazobactam, and others (or combinations of these antibiotics) that can be readily recognized by a person skilled in the art.

In some embodiments, suitable antibiotics comprise antibiotics effective against pathogen *Pseudomonas aeruginosa* such as Aminoglycosides, Carbapenems, Ceftazidime, Cefepime, Ceftobiprole, Fluoroquinolones, Piperacillin, Ticarcillin, tobramycin, aztreonam, coliston, and others (alone or in combination) that can be recognized by a skilled person.

Additional antibiotics suitable in particular for treatment of cystic fibrosis include Amoxicillin and clavulanic acid (Augmentin®), Methicillin, oxacillin, nafcillin, cloxacillin, dicloxacillin, carbenicillin, ticarcillin, piperacillin, mezlocillin, azlocillin, ticarcillin and clavulanic acid (Timentin®), piperacillin and tazobactam (Zosyn®), cephalexin, cefdinir, cefprozil, cefaclor, cefuroxime, sulfisoxazole, erythromycin/sulfisoxazole, tobramycin, amikacin, gentamicin, erythromycin, clarithromycin, azithromycin, tetracycline, doxycycline, minocycline, tigecycline, ciprofloxacin, levofloxacin, vancomycin, linezolid, imipenem, meripenem, and aztreonam. A person skilled in the art would be able to select appropriate antibiotics for treating cystic fibrosis caused by particular pathogen. An exemplary indication of antibiotic, is shown in Table 2 below From Orenstein, D. *Cystic Fibrosis: A Guide for Patient and Family,* 4th ed. LWW; 2011.

TABLE 2

An exemplary list of antibiotics

| Type and kinds | Bacteria Treated | How Taken |
|---|---|---|
| Penicillins | | |
| Amoxicillin and clavulanic acid (Augmentin ®) | *Staphylococcus aureus* (Staph) | |
| Methicillin, oxacillin and nafcillin | Pseudomonas (*P. aeruginosa*) | Intravenous, intramuscular |
| Cloxacillin and dicloxacillin | Staph | Oral |
| Cabenicillin, ticarcillin, piperacillin, mezlocillin and azlocillin | *P. aeruginosa* | Intravenous |
| Ticarcillin and clavulanic acid (Timentin ®) | Staph, *P. aeruginosa* | intravenous |
| Piperacillin and tazobactam (Zosyn ®) | *P. aeruginosa* | intravenous |
| Cephalosporins | | |
| Cephalexin, cefdinir, cefprozil and cefaclor | Staph, *P. aeruginosa* | oral |
| Cefuroxime | Staph | oral |
| Sulfa | | |
| Sulfisoxazole | *P. aeruginosa* | oral |
| Erythromycin/sulfisoxazole | Staph | oral |
| Aminoglycosides | | |
| Tobramycin, amikacin, gentamicin | *P. aeruginosa* (in combination with gentamicin, tobramycin, and amikacin; also work well with anti-Pseudomonas penicillin drug) | Intravenous, inhaled |
| Macrolides | | |
| Erythromycin, clarithromycin and azithromycin | Staph and may help reduce inflammation from *P. aeruginosa* | Oral, intravenous |

TABLE 2-continued

An exemplary list of antibiotics

| Type and kinds | Bacteria Treated | How Taken |
|---|---|---|
| Tetracyclines | | |
| Tetracycline, doxycycline, minocycline, and tigecycline | Formerly *P. aeruginosa*, some Burkholderia cepacian and Staph | Oral, intravenous, intramuscular |
| Quinolones | | |
| Ciprofloxacin, levofloxacin | Pseudomonas | Oral, intravenous |
| Vancomycin | | |
| Vancomycin | Staph and methicillin-resistant *Staphylococcus aureus* (MRSA) | intravenous |
| Linezolid | | |
| Linezolid | MRSA and some mycobacteria | Oral, intravenous |
| Imipenem & Meripenem | | |
| Imipenem & Meripenem | *P. aeruginosa*, Staph | intravenous |
| Aztreonam (Cayston ®) | | |
| Aztreonam (Cayston ®) | *P. aeruginosa* | Intravenous, inhaled |

As a person skilled in the art would appreciate, pyocyanin-like phenazine as a natural pigment can change its color from blue to yellow upon reduction, thus can be used as bacterial pigments for applications in food, pharmaceutical, cosmetics, paint, and textile industries. Thus, in some embodiments, the phenazine degrading agents herein described can be administered to a medium comprising pyocyanin-like phenazine pigments in absence of bacteria as a color-control agent to control the color of the medium.

In some embodiments, a composition can comprise one or more phenazine degrading agents herein described with one or more medium components.

In some embodiments, the composition can comprise medium components such as sodium thioglycolate (HS—$CH_2CO_2Na$), sodium dithionite, Organic; simple sugars e.g. glucose, acetate or pyruvate; extracts such as peptone, tryptone, yeast extract etc., hydrogen carbonate salts ($HCO_3^-$), amino acids, $NH_4Cl$, $(NH_4)_2SO_4$, $KNO_3$, $KCl$, $K_2HPO_4$, $MgCl_2$, $MgSO_4$, $CaCl_2$, $Ca(HCO_3)_2$, $FeCl_3$, $Fe(NH_4)(SO_4)_2$, Fe-chelates, $CoCl_2$, $ZnCl_2$, $Na_2MoO_4$, $CuCl_2$, $MnSO_4$, $NiCl_2$, $Na_2SeO_4$, $Na_2WO_4$, $Na_2VO_4$, Vitamins, amino acids, purines, pyrimidines.

In some embodiments, the composition can comprise a basic binder, and an isocyanate compound and in particular an isocyanate pre-polymer. In some embodiments, the composition can comprise an aqueous dispersion of an acryl-modified polyester resin, a blocked polyisocyanate compound having a nonionic hydrophilic group; and an aqueous dispersion of acrylic-based polymer fine particles.

In several embodiments, the composition comprising one or more phenazine degrading agent and one or more medium component can act as a barrier against environmental conditions. Such chemical composition can contain one or more pigments to impact color and opacity, binder polymer forming a matrix to hold the one or more pigments in place, extender to improve adhesion, solvent such as organic solvent or water to reduce the viscosity of the paint, additives to modify the properties of the paint and other ingredients identifiable to a person skilled in the paint industry.

As described herein, the phenazine degrading agents, bacteria, antimicrobial agents or compositions herein described can be provided as a part of systems to perform any methods, including any of the assays described herein.

In some embodiments, a system can comprise one or more phenazine degrading agents alone or in combination with pyocyanin-like phenazine in a certain proportion to produce a desired color.

In embodiments of systems where detection can be performed, the systems can be provided in the form of arrays or kits of parts. An array, sometimes referred to as a "microarray", can include any one, two or three dimensional arrangement of addressable regions bearing a particular molecule associated to that region. Usually, the characteristic feature size is micrometers.

In a kit of parts, the phenazine degrading agents, antimicrobial agent, candidate phenazine degrading agents, bacteria and compositions and other reagents to perform the method can be comprised in the kit independently. In particular, the phenaxine degrading agents, antimicrobial agent, candidate phenazine degrading agents, bacteria can be included in one or more compositions, and each phenazine degrading agent can be in a composition together with a suitable vehicle. In some embodiments, a kit can comprise a phenazine degrading agent with medium components within a composition herein described.

Additional components can include labeled molecules and in particular, labeled polynucleotides, labeled antibodies, labels, microfluidic chip, reference standards, and additional components identifiable by a skilled person upon reading of the present disclosure. The terms "label" and "labeled molecule" as used herein as a component of a complex or molecule referring to a molecule capable of detection, including but not limited to radioactive isotopes, fluorophores, chemiluminescent dyes, chromophores, enzymes, enzyme substrates, enzyme cofactors, enzyme inhibitors, dyes, metal ions, nanoparticles, metal sols, ligands (such as biotin, avidin, streptavidin or haptens) and the like. The term "fluorophore" refers to a substance or a portion thereof which is capable of exhibiting fluorescence in a detectable image. As a consequence, the wording "labeling signal" as used herein indicates the signal emitted from the label that allows detection of the label, including but not limited to radioactivity, fluorescence, chemiluminescence, production of a compound in outcome of an enzymatic reaction and the like.

In some embodiments, detection of a viable bacteria can be carried either via fluorescent based readouts, in which the labeled antibody is labeled with fluorophore, which includes, but not exhaustively, small molecular dyes, protein chromophores, quantum dots, and gold nanoparticles. Additional techniques are identifiable by a skilled person upon reading of the present disclosure and will not be further discussed in detail.

In particular, the components of the kit can be provided, with suitable instructions and other necessary reagents, in order to perform the methods here described. The kit will normally contain the compositions in separate containers. Instructions, for example written or audio instructions, on paper or electronic support such as tapes or CD-ROMs, for carrying out the assay, will usually be included in the kit. The kit can also contain, depending on the particular method used, other packaged reagents and materials (i.e. wash buffers and the like).

The methods, herein described, can be performed in vivo and/or in vitro as will be understood by a skilled person.

EXAMPLES

The related compositions, methods and systems herein disclosed are further illustrated in the following examples, which are provided by way of illustration and are not intended to be limiting. In particular, the following examples illustrate exemplary phenazine degrading agents, methods and protocols for degrading phenazine. A person skilled in the art will appreciate the applicability and the necessary modifications to adapt the features described in detail in the present section, to additional phenazine degrading agents and related compositions, methods and systems according to embodiments of the present disclosure. The following materials and methods were used.

Strains, medium and growth conditions. Primers, strains and plasmids are listed in Table 3 (31-33). All expression constructs were derivatives of the IPTG inducible plasmid pET-20b(+) (Novagen). The gene for MFORT_14352 lacking the N-terminal 29 amino acids (podA$_{30-162}$) was PCR amplified from *Mycobacterium fortuitum* ATCC 6841 using primers listed in Table 3 and first placed into the NdeI and PstI sites of plasmid pSD5 (34) to verify expression of a His tag construct in a vector used previously for podA expression in *Rhodococcus* sp. JVH1 (9). Primers encoded both a TEV protease cleavage site and a 6×-His tag on the C-terminus. Activity was observed in the *Escherichia coli* cloning strain, so the podA$_{30-162}$ construct was transferred to an *E. coli* expression vector for further analysis. PCR product was digested with NdeI and NotI and ligated into digested pET-20b(+) before transfer into *E. coli* BL21(DE3) cells by electroporation (33). Mutant proteins were generated by PCR amplifying pET-20b(+) containing podA$_{30-162}$ with primers encoding the relevant mutation (Table 3).

TABLE 3

Strains, primers and plasmids used in this study.

| Strain | Reference |
| --- | --- |
| *Pseudomonas aeruginosa* PA14 | (32) |
| *P. aeruginosa* Δphz | (31) |

TABLE 3-continued

Strains, primers and plasmids used in this study.

| | |
| --- | --- |
| *Escherichia coli* BL21(DE3) | (33) |

| Plasmid | Description |
| --- | --- |
| pET20b(+)-podA$_{30-162}$ | podA$_{30-162}$ expressed from the IPTG inducible promoter of pET-20b(+) |
| pET20b(+)-podA$_{30-162, D68A}$ | D68A mutant podA$_{30-162}$ expressed from the IPTG inducible promoter of pET-20b(+) |
| pET20b(+)-podA$_{30-162, D72N}$ | D72N mutant podA$_{30-162}$ expressed from the IPTG inducible promoter of pET-20b(+) |
| pET20b(+)-podA$_{30-162, C88A, C102A}$ | C88A, C102A double mutant podA$_{30-162}$ expressed from the IPTG inducible promoter of pET-20b(+) |
| pET20b(+)-podA$_{30-162, C88S, C102S}$ | C88S, C102S double mutant podA$_{30-162}$ expressed from the IPTG inducible promoter of pET-20b(+) |
| pET20b(+)-podA$_{30-162, H121A}$ | H121A mutant podA$_{30-162}$ expressed from the IPTG inducible promoter of pET-20b(+) |
| pET20b(+)-podA$_{30-162, E154A}$ | E154A mutant podA$_{30-162}$ expressed from the IPTG inducible promoter of pET-20b(+) |
| pET20b(+)-podA$_{30-162, Y156F}$ | Y156F mutant podA$_{30-162}$ expressed from the IPTG inducible promoter of pET-20b(+) |

| Primer | Sequence |
| --- | --- |
| podA30-162-NdeI-F | AAAACATATGGACGGTCGCGGCGGCCGGAGTA (SEQ ID NO: 3) |
| podA30-162-TEV-Pst-R | AAAACTGCAGTCAATGGTGATGGTGATGGTGGCTCTGGAAGTACAGGTTTTCGGCTTTCGTCAGTTTCAATTCGTACTTCTCA (SEQ ID NO: 4) |
| podA30-162-pET20b-F-NdeI | AAAACATATGGACGGTCGCGGCGGCCGGAGTACA (SEQ ID NO: 5) |
| podA30-162-pET20b-R-NotI | TTTTGCGGCCGCTCAATGGTGATGGTGATGGTGGCT (SEQ ID NO: 6) |
| CtoS-F | GATAATCCAATGACCTATTCCGAACTGACCATTCACCTCGATGCAGGTGA (SEQ ID NO: 7) |
| CtoS-R | CGGCGTCACATTGGTGAAAAAGGACGCGCCGCCGTCATATCCGACCTGCTTACCGT (SEQ ID NO: 8) |
| CtoA-F | GGATAATCCAATGACCTATGCCGAACTGACCATTCA |

TABLE 3-continued

Strains, primers and plasmids used in this study.

| | |
|---|---|
| | CCTCGATGCAGGTGA (SEQ ID NO: 9) |
| CtoA-R | GGCGTCACATTGGTGAAA AAGGCCGCGCCGCCGTCA TATCCGACCTGCTTACCG TCT (SEQ ID NO: 10) |
| D68A-F | GCCATCTTCTCCGACATC CTCTCGGTAGA (SEQ ID NO: 11) |
| D68A-R | CATGTCTCCGACATCCAT ACCCGGT (SEQ ID NO: 12) |
| H121A-F | GCCACACTCGCACCTTTC ACCATGGCCA (SEQ ID NO: 13) |
| H121A-R | CGGGGTGAGGCTACGGGC AAAGATCTCA (SEQ ID NO: 14) |
| E154A-F | GCGAAGTACGAATTGAAA CTGACGAAAGC (SEQ ID NO: 15) |
| E154A-R | ATCGGGAGTCGCAACACC GGATACGGT (SEQ ID NO: 16) |

Product was cut with DpnI to remove WT vector, phosphorylated with T4 polynucleotide kinase, and ligated to generate a circular mutant protein expression construct. For D72N and Y156F mutants, DNA fragments encoding the mutation were synthesized (Integrated DNA Technologies) and cloned into pET-20b(+) as for the wild type sequence. Enzymes for cloning were purchased from New England Biolabs. Constructs were transferred to *E. coli* BL21(DE3) for expression. All mutations were confirmed by Sanger sequencing (Laragen and Retrogen). When necessary, 100 µg mL$^{-1}$ carbenicillin was included in all growth media to maintain selection for the plasmid. To measure the effect of PodA$_{30-162}$ on phenazine production in planktonically grown *P. aeruginosa*, cultures were grown overnight in 5 mL volumes of tryptic soy broth (TSB) or succinate minimal medium (arginine medium recipe from Glasser et al., 2014 with 40 mM sodium succinate in place of arginine) (3) in the presence 1 µg mL$^{-1}$ PodA$_{30-162}$. Cells were removed by centrifugation and supernatants were analyzed by HPLC as previously described (9). See below for a description of biofilm growth of *P. aeruginosa* PA14. To induce protein expression, an overnight culture was inoculated 1/1000 in Terrific Broth (BD Difco). Cultures were grown in baffled Erlenmeyer flasks (1 L culture per 3 L flask) at 37° C. with 150 rpm agitation in a shaking incubator (Innova 44 shaking incubator, New Brunswick). After 3-4 hours, the temperature was changed to 16° C. and cultures were induced with 50 µM (final concentration) IPTG and left to incubate overnight. Cells were then pelleted by centrifugation, flash frozen in liquid N$_2$, and stored at −80° C. for up to 1 month before protein purification.

Generation and analysis of phenazines. Pyocyanin (PYO) was purified directly from cultures of *P. aeruginosa* PA14 grown on succinate minimal medium using a previously established protocol (31). Briefly, culture supernatants were first extracted with 0.4 volume dichloromethane (DCM). DCM extracts were treated 1:1 with 0.01 M HCl to acidify PYO and extract it back into the aqueous phase. Finally, 1 M NaOH was added to pH7, and PYO was extracted back into DCM and dried in vacuo. This crude preparation was used for routine analysis of FPLC fractions for activity. To further purify PYO, extracts were dried and purified by reverse phase HPLC as described (26, 31). 1-hydroxyphenazine (1-OH-PHZ) was manufactured by TCI America. Phenazine-1-carboxylic acid (PCA) and phenazine-1-carboxamide (PCN) standards were purchased from Princeton Biomolecular Research, Inc. Phenazines from culture supernatants were analyzed and measured by HPLC as described previously (6, 9).

Protein extraction and purification. Frozen cell pellets were thawed at room temperature and suspended in 25 mL wash buffer (200 mM KCl, 20 mM imidazole, Tris, pH 7.6). Cell suspensions were homogenized in an Emulsiflex device (Avestin). Cell debris was removed by centrifugation (Avanti J-25 centrifuge, J-series JA-25.50 rotor, Beckman-Coulter) at 50,000×g and supernatant was applied to a nickel GE Healthcare HisTrap HP 5 mL nickel column on a GE Healthcare ÄKTAxpress FPLC. All protein purification steps were carried out at room temperature. The column with bound protein was washed with wash buffer until the UV (280 nm) trace stabilized below 20 mAU. Proteins were eluted across a gradient of 20-500 mM imidazole applied over 10 column volumes. PYO demethylase activity generally eluted around 300 mM imidazole. Eluted protein was concentrated to ~3 mL (Amicon Ultra-15 centrifugal filters, Ultracel 3K MWCO) and treated overnight with 1% wt/wt TEV protease (35) while dialyzing (Spectra/Por Biotech Dialysis membrane, MWCO: 3.5-5 kD) into buffer containing 200 mM KCl and 20 mM Tris, pH7.6 at 4 C. Samples were run back through the nickel column and PYO demethylase activity was collected in the flow through. Protein was concentrated to 250-500 µL (Amicon Ultra—0.5 mL centrifugal filters, Ultracel—3K MWCO) and loaded on a GE Healthcare HiLoad 16/60 Superdex 200 prep grade gel filtration column and run at 1 mL min$^{-1}$ with gel filtration buffer (100 mM CaCl$_2$, 20 mM Tris, pH 7.6). CaCl$_2$ in the buffer was necessary for maximal PodA$_{30-162}$ activity. Activity eluted after ~83 mL. For applications requiring highly purified PodA$_{30-162}$ (e.g., crystallography), an acid precipitation step (400 mM phosphate/citrate, pH 4.2) was added either before or after gel filtration chromatography to precipitate trace contaminants that were not apparent by SDS-PAGE. PYO demethylase activity remained in the supernatant. For acid precipitation, sample was dialyzed into 20 mM Tris, pH 7.6 between steps to avoid mixing CaCl$_2$ and phosphate buffers. Purified PodA$_{30-162}$ was dialyzed into 20 mM Tris, pH7.6 and stored at 4° C.; protein remained stable with no apparent loss of activity for as long as tested (up to 4 months). To determine the approximate molecular weight of purified proteins, the elution peak was compared to Bio-Rad gel filtration standards run across the same column with gel filtration buffer. Mutant proteins were purified on the same day as wild type and fractions where activity was seen in wild type were also collected for mutant preparations. Protein quantification was carried out by Bradford assay (36) (Quick Start 1× Bradford Dye Reagent, Bio-Rad) using pre-diluted Bovine Serum Albumin standards (Thermo Scientific) to establish a standard curve. A purification from 6 liters of culture typically yielded 1-2 mg protein. Purified proteins were routinely subject to SDS-PAGE using 4-20% Mini-PROTEAN TGX precast protein gels (Bio-Rad) and stained with Coomassie Blue. All protein preparations were colorless indicating that flavins were not present in the purified protein.

Enzyme activity and analysis. PYO demethylation by PodA$_{30-162}$ was first determined by HPLC analysis as described previously (6, 9). To detect formaldehyde evolution, 150 nM protein was mixed with 50 µM PYO in 1 mL of 20 mM Tris pH 7.6 amended with 200 µL Nash reagent (2 M ammonium acetate, 50 mM acetic acid, 20 mM acetylacetone) and incubated at 55° C. until the reaction proceeded to completion (37, 38). The products were determined by HPLC using the same method as used for phenazine quantification. To monitor the formation of reduced phenazine, protein and 50 µM PYO were placed into an anaerobic chamber (Coy Laboratory Products) under an atmosphere of $H_2/N_2$ (5:95) and left overnight before allowing the reaction to proceed. To generate reduced PYO and 1-OH-PHZ, 50 µM were mixed with 1 mM sodium dithionite. The formation of reduced phenazine products was assayed visually under UV illumination (39). A BioTek Synergy 4 microplate reader (BioTek) plate reader in the anaerobic chamber was used to measure the emission spectrum of products with excitation at 250 nm. To determine the activity of PodA$_{30-162}$ in the presence of glycerol, salts, or varying pH, 30 nM protein was suspended in 500 µL buffer, 40 µM PYO was mixed with 2× solution containing the buffer of interest (500 µL), and solutions were preheated to 30 C. For pH range measurements, the following buffers were used (40 mM, adjusted with KOH): acetic acid, pH 4.9; MES, pH 5.4 and 5.7; HEPES, pH 6.1; Tris, pH 6.9 and 7.5; Bicine, pH 7.8, 8.3 and 8.7; CHES, pH 9.4. To measure reaction rates, cuvettes containing the 2×PYO solution were placed in a Evolution 260Bio UV-Vis spectrophotometer (Thermo Scientific) and 500 µL of 30 nM protein was added at time 0 (15 nM protein and 20 µM PYO, final concentration). Reaction progress was monitored by measuring absorbance at 313 nm (40) every 0.5 seconds for 5 minutes. To measure kinetic parameters ($k_{cat}$, $K_m$) 15 nM protein was used in a reaction buffer of Bicine, pH 7.8; reactions were monitored as before with measurements every 0.2 seconds. The rate from the first 10 seconds of the reaction was used for the determination of kinetic parameters. Kinetic parameters were calculated in Microsoft Excel using the Solver plug-in and fitting data to ideal Michaelis-Menton plots with non-linear regression of experimental data (41). For measurements of the rate of methoxy-PMS demethylation, 300 nM protein was used and methoxy-PMS loss from the reaction mixture was monitored at 500 nm wavelength. Methoxy-PMS was purchased from TCI America. For assays with mutant proteins, 60 nM protein was used. The stimulatory effects of flavin or 2-oxoglutarate addition was determined by adding 25 µM flavin or 2-oxoglutarate to 20 µM PYO and 15 nM PodA$_{30-162}$ and monitoring the reaction. Experiments testing alternative substrates were carried out using 1 mL reaction volumes containing 20 mM Tris (pH 7.6) and 50 µg mL$^{-1}$ PodA$_{30-162}$. Alternative substrates tested were 10-methylphenothiazine (AlfaAesar), phenazine methosulfate (AlfaAesar), methoxyphenazine methosulfate (TCI America), and 4-keto-N-ethylphenazine. 4-keto-N-ethylphenazine was synthesized from phenazine ethosulfate (Sigma-Aldrich) by incubating under fluorescent light overnight followed by purification by HPLC as described (6, 42). As phenazine methosulfate is light sensitive and spontaneously converts to PYO in the presence of light, all reactions were carried out in the dark, and activity was assessed by end point analysis by HPLC after 4 hours (9).

Protein crystallography, X-ray diffraction and analysis. Crystallization screens were performed with the JCSG+ screen (Molecular Dimensions) using vapor diffusion in sitting drop format with assistance from the California Institute of Technology Molecular Observatory. A Crystal Gryphon liquid-handling robot (Art Robins) was used to mix 0.2 µL of screen solution with 0.2 µL of protein solution (5 mg mL$^{-1}$ in 20 mM Tris, pH 7.6 amended with 200 µM 1-OH-PHZ in DMSO (1% final concentration)). Crystals formed in JCSG+ conditions C1, C6, and D12 after 3 days at 20° C. Varying the salt and polymer concentrations in a 24-well plate showed that JSCG+ condition C1 gave robust crystal growth in vapor diffusion sitting drop format using 2 drops in Micro-Bridges (Hampton Research). Protein (5 mg mL$^{-1}$) was mixed with mother liquor (1 µL:1 µL) composed of 20% w/v PEG 8000, 200 mM NaCl, 200 µM 1-OH-PHZ, 1% DMSO, and 100 mM sodium phosphate dibasic/citric acid, pH 4.2. Crystals generally formed within 3 days at 20° C. and were rod shaped with typical dimensions of 50×50× 100 Crystals were equilibrated into a cryoprotectant solution (12% w/v PEG 8000, 20% w/v PEG 300, 100 mM NaCl, 100 µM 1-OH-PHZ, 0.5% DMSO, and 50 mM sodium phosphate dibasic/citric acid, pH 4.2) by gradually replacing the sitting drop solution with cryoprotectant solution over the span of 10-15 minutes. Crystals were then mounted in a nylon loop and flash frozen in liquid nitrogen. Data collection was performed at 100 K at the Stanford Synchrotron Radiation Lightsource (SSRL) beamline 12-2 equipped with a PILATUS 6M Pixel Array Detector. X-ray diffraction data were collected at 12,000 eV with a beamstop distance of 32.7 mm and a detector distance of 280 nm. Images were collected every 0.15° for a full 360° of rotation around a single axis (generating a total of 2400 images). For well-diffracting crystals, an additional dataset was collected at 7,000 eV to capture the anomalous signal from sulfur and calcium. Diffraction images were integrated and scaled using the XDS package (43). To ensure maximum data completion, the two highest quality datasets were combined using XSCALE and further processed using POINTLESS, AIMLESS and CTRUNCATE in the CCP4 software suite (44-48). The structure was solved by molecular replacement in PHASER (49) using a search model derived from a structural prediction by Robetta (14-16) with disordered loops trimmed in Coot (50). A preliminary model was constructed using phenix.AutoBuild (51) and refined using phenix.refine (52, 53) and model building in Coot to yield a model with $R_{free}$=0.22. LigandFit (54, 55) analysis in PHENIX (56) was used to model 1-OH-PHZ into the active site of PodA$_{30-162}$ with refinement restraints generated using elBOW (simple optimization method) (57). The model was modified in Coot to trim side chains with poor electron density coverage. A highly coordinated water molecule was identified by phenix.refine as a potential calcium atom, presumably originating from the inclusion of 100 mM CaCl$_2$ during the final protein purification step. Analysis of the anomalous difference map from a low-energy dataset supported this identification (FIGS. 8A-C) and so the corresponding water molecules were replaced with calcium atoms and metal-coordination restraints were generated with phenix.metal_coordination via ReadySet!. The final rounds of refinement were performed using TLS groups (58) generated by phenix.refine and hydrogen atoms set in their riding positions to yield a final model of $R_{free}$=0.195. Figures were rendered with PYMOL version 1.7.2.1, Schrödinger, LLC.

Biofilm experiments. For all experiments involving inactivated PodA, either the E154A mutant or PodA$_{30-162}$ that was subjected to a 1 hour treatment at 98° C. was used. To test the ability of PodA$_{30-162}$ to degrade PYO in the presence of DNA, genomic DNA (gDNA) from *P. aeruginosa* PA14 was used in modified versions of previously described assays (59). For experiments using DNA pellets, 0.5 mg of gDNA was pelleted in the presence of 300 mM sodium acetate, pH 5.2 and 70% ethanol. Pellets were washed with 70% ethanol and dried. 200 µL of 800 µM PYO was added to the gDNA pellet without mixing and left to sit at room temperature for 6 hours to allow for diffusion of PYO into the gDNA pellet. The pellet was washed once with 70% EtOH, and submerged in a solution containing 10 mM Tris, pH 7.0 and 40% isopropanol. The pellet remained blue, consistent with an association of PYO with DNA. PodA$_{30-162}$ was added to the isopropanol solution to a final concentration of 2 µg mL$^{-1}$ and left to sit for 3 hours to allow for the reaction to proceed. Tubes were imaged before and after PodA$_{30-162}$ treatment. For experiments using solubilized gDNA, a 400 µg mL$^{-1}$ solution of gDNA was mixed with PYO and allowed to equilibrate for 6 hours. The PYO gDNA mixture was amended with 1 µg mL$^{-1}$ PodA$_{30-162}$ and loss of PYO was monitored on a BioTek Synergy 4 microplate reader (BioTek) plate reader at 690 nm. Standards were included to quantify PYO loss over time. To assess biofilm formation in the presence of PodA$_{30-162}$, biofilms were grown in Nunc Lab-Tek chambered coverglass slides (8-well, 0.8 cm$^2$ area, supplier #155411) using a modified protocol (22). PA14 was inoculated into succinate minimal medium and grown overnight to stationary phase. Cells were resuspended in fresh medium and diluted to a starting OD$_{500}$ of 0.5 in succinate minimal medium. PodA$_{30-162}$ (2 µg mL$^{-1}$, final concentration) or DNase (20 µg mL$^{-1}$) (22) was added and 250 µL was added to each well of the 8-well chambered coverglass. Cultures were grown for 5 hours at 37° C. and 100 rpm (Innova 44 shaking incubator, New Brunswick) in a humidified chamber. After incubation, liquid was removed from each well by drawing with a pipet tip placed in the corner of each well and chambers were washed twice with 400 µL of biofilm wash (Tris buffer, pH 7.6 and 100 mM NaCl) to remove planktonic and loosely bound cells. Attached biomass was stained by adding 450 µL biofilm wash containing 10 µg mL$^{-1}$ DAPI (4',6-diamidino-2-phenylindole) (Santa Cruz Biotechnology). Surface associated biomass was imaged on a Leica TCS SPE confocal microscope with a ACS APO 40x/1.15 oil immersion objective. A 405 nm solid-state laser was used for excitation, and data was collected from 420-500 nm. Images were collected from the same relative position in each well along the mid-point of the outer edge on the opposite edge from where the washing pipet was placed. Images were collected as 10 µm Z-stacks (10 slices) to image the biofilm in its entirety over a surface area of 40,000 µm$^2$. All Z-stacks were collected in 8-bit mode with 1024×1024 scan format and a line averaging of 2. A sum intensity projection was produced from each Z-stack using ImageJ software (60). Images were then thresholded to include pixels with a maximum intensity value >0.15× the maximum possible intensity, and thresholded images were used to determine surface coverage of each biofilm. Data were collected from 12 biological replicates.

Biofilm aggregate experiments. To test the effect of oxygen limitation in the presence of PodA$_{30-162}$, biofilm aggregates were grown embedded in 0.5% noble agar blocks containing succinate minimal medium. Cultures were grown overnight to stationary phase in LB, washed once with succinate minimal medium, and resuspended to OD$_{600}$ 1.0. Samples were diluted 1:100 in agar at 44° C. and 175 µL was transferred to Nunc Lab-Tek chambered coverglass slides (8-well, 0.7 cm$^2$ area, supplier #155409). After the agar solidified, aggregates were grown for 22 hours in a humidified chamber at 37° C. before PodA$_{30-162}$ (2 µg mL$^{-1}$, final concentration) was added to the top of the agar for an additional 5 hours at 37° C. After treatment, 1 µL of stain from ThermoFisher LIVE/DEAD BacLight Bacterial Viability Kit in 50 µL ddH$_2$O was added to the top of the agar for 12 minutes before microscopic analysis. SYTO-9 from the LIVE/DEAD stain kit was used in place of DAPI to minimize background fluorescence. Biomass was imaged with a Leica TCS SPE confocal microscope with a ACS APO 10x/0.30 objective. A 488 nm solid-state laser was used for excitation, and data was collected from 510-550 nm. Images were collected across a 500 µm Z-stack with a 10 µm step size. All Z-stacks were collected in 8-bit mode with 512×512 scan format and a line averaging of 2. Biomass was quantified in ImageJ software (60) by identifying the Z-slice with the highest average fluorescent intensity (generally ~200 below the agar surface), and setting the pixel threshold using the default ImageJ thresholding parameters at the Z-slice equivalent to the 100 µm depth. The number of particles in each slice of the Z-stack was determined using this threshold value and counting particles >10 µm$^2$ in area. To compare biofilm aggregate biomass from different experiments, all Z-stacks were normalized by depth so that the Z-slice with the highest average staining intensity was considered the mid-point of the 3D reconstruction. This processing allowed for comparison of datasets collected on different days with slightly different staining intensities and different Z-plane starting coordinates. Particle numbers for each slice were averaged between independent experiments and plotted against depth to quantify biofilm aggregates. Only experiments with between 400 and 600 aggregates at the plane of peak stain intensity were used for averaging and statistical analysis; this ensured equivalent biomass was present in each experiment.

Oxygen diffusion modeling. To model oxygen diffusion into agar blocks embedded with *P. aeruginosa* aggregates, the oxygen diffusion model from (29) was utilized. Cell numbers were estimated by determining the average number of aggregates present and calculating the average volume of a given particle with the ImageJ 3D-object counter plug-in (61). Given these values, average cell number per mL was estimated by dividing the volume of total detected biofilm aggregates by the average volume of a *P. aeruginosa* cell (62) yielding a cell density estimate of 5×10$^8$. This cell density value is consistent with the overnight growth of *P. aeruginosa* in succinate minimal medium. Oxygen diffusion was modeled using this value and 2-fold higher and lower densities to encompass a plausible range.

Example 1: Identification of a Hypothetical Protein Necessary for PYO Degradation Bacteria from phylogenetically diverse taxa secrete colorful redox-active metabolites, such as the well-studied phenazines produced by multiple species, including *Pseudomonas aeruginosa* (1, 2) (FIGS. 2A-B). Phenazines can be toxic to other cells but also benefit their producers by facilitating extracellular electron transfer and survival in anoxic environments (3-6). These latter functions support the growth of antibiotic-resistant biofilms, and *P. aeruginosa* mutants that cannot make phenazines are defective in biofilm development (5). Accordingly, it was reasoned that selectively manipulating phenazines might present a means to control biofilms. One way to influence extracellular metabolites is through active modification or degradation by other organisms (7-9).

In this example, a group of mycobacteria that enzymatically degrade phenazines were described and genes that catalyze distinct steps in degradation was identified (9). Deletion of candidate dioxygenase homologs from *M. fortuitum* ATCC 6841 abolished the ability to grow with the phenazine PCA as the sole carbon source (9). Each gene was replaced with a gentamicin resistance cassette. Gentamicin-resistant colonies with disruptions in each gene were streaked onto agar medium with 2.5 mM PCA as the sole carbon source. None of the mutants grew under these conditions, indicating that the mutated genes are essential for growth with PCA as a carbon source (FIG. 23A).

Figure 22:
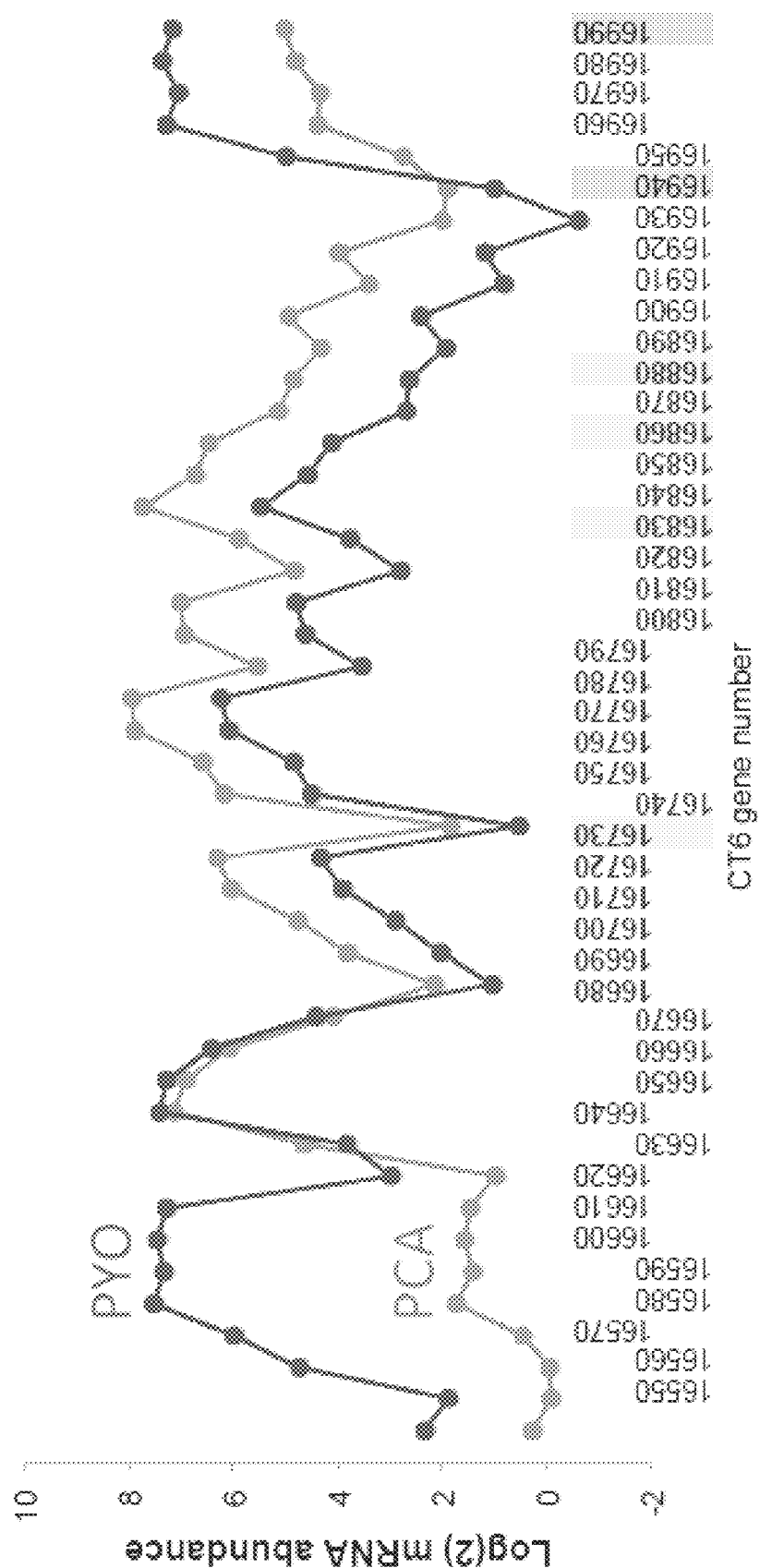
FIG. 22 shows graphed results of an exemplary mRNA abundance of *M. fortuitum* strain CT6 genes after 20-min exposure to PCA or PYO. Values are given as log 2 fold change versus a mock treatment. An ~40-kb region of the genome shows a large change in gene expression in response to phenazines. Strain CT6 gene numbers are listed on the x axis, with genes on the plus strand listed on the top row and genes on the minus strand listed on the bottom row. Gene numbers from 16650 to 16890 are present in the genome of *Rhodococcus* strain JVH1. Black points represent relative mRNA abundance after PYO exposure, and gray points correspond to PCA exposure. This Figure is from reference (9).

Transcriptome sequencing (RNA-Seq) approach was used to identify candidate genes important to PYO degradation in *P. aeruginosa*-like strain CT6. The genes important for PCA-dependent growth showed increased mRNA abundance after a 20-min exposure to either PCA or PYO (FIG. 22). In fact, the entire region of the CT6 genome that shares homology with *Rhodococcus* sp. strain JVH1 (an organism that can degrade only PCA) was highly expressed in the presence of either PCA or PYO. Additionally, genes flanking this region had increased mRNA abundance and were induced to a greater extent by PYO.

Figure 23B:
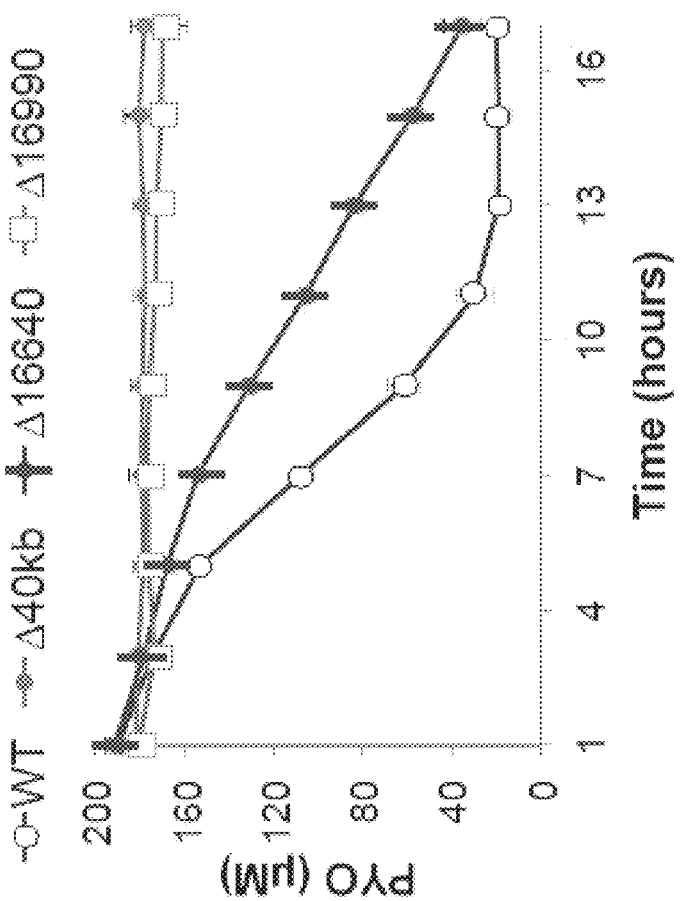
FIG. 23B shows exemplary graphed results of PYO degradation characteristics of M. fortuitum mutants grown in 10% LB-Tw medium supplemented with 200 uM PYO. All mutants could grow with 10% LB as the carbon source, but only a subset displayed a defect in PYO degradation. Data are averages and SD for three cultures.
Figure 23A:
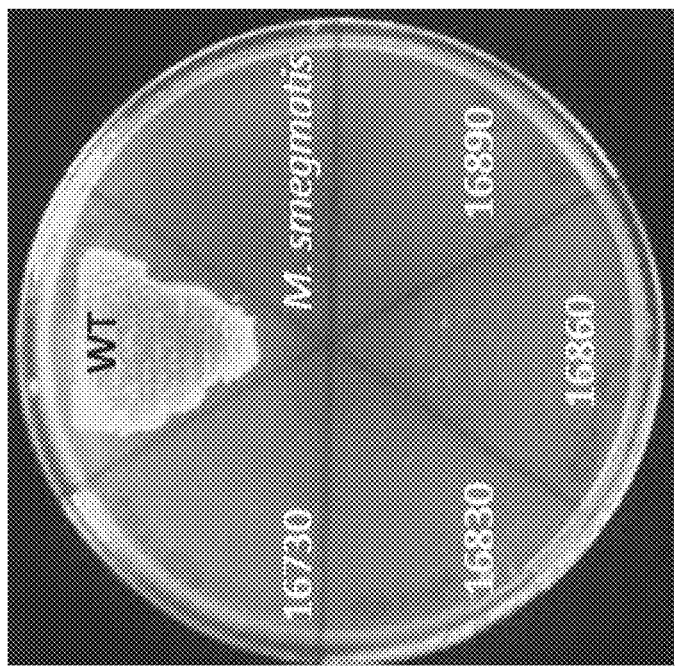
FIG. 23A shows a chart and an image illustrating an exemplary growth of *M. fortuitum* individual gene mutants with PCA as a sole carbon source. Mutations in the four putative dioxygenase genes (MFORT_16269, MFORT_16319, MFORT_16334, and MFORT_16349), and each gene was replaced with a gentamicin resistance cassette. Gentamicin-resistant colonies with disruptions in each gene were streaked onto agar medium with 2.5 mM PCA as the sole carbon source. None of the mutants grew under these conditions, indicating that the mutated genes are essential for growth with PCA as a carbon source.
Figure 26:
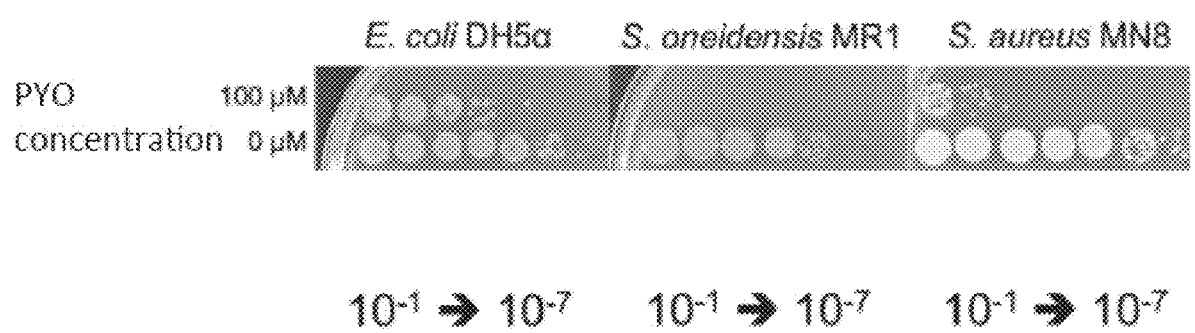
FIG. 26 shows images of exemplary E. coli, S. oneidensis, and S. aureus colonies that were plated in presence of 0 uM or 100 uM PYO. The results show that phenazine degradation is protective to sensitive organisms.

Next, a mutant lacking the entire ~40-kb region (Δ40 kb::Gm$^r$) of the genome induced by phenazines was constructed in *M. fortuitum* and found to completely lack the ability to degrade phenazines, including PYO (FIG. 23B). This locus contains genes for an additional predicted dioxygenase (MFORT_16204 [XA26_16600]) and a monooxygenase (MFORT_16224 [XA26_16640]) in one of the flanking regions; however, mutants with mutations in both genes were still capable of PYO degradation (9). It is noted that Δ16224::Gm$^r$ degrades PYO more slowly than the wild type (WT), suggesting a possible role in a downstream reaction in the PYO degradation pathway. A mutant missing a three-gene operon in the other flanking region (MFORT_14352 to MFORT_30529 [XA26_16990 to XA26_16960]) lacked the ability to degrade PYO. A single gene mutant lacking MFORT_14352, annotated as a hypothetical protein, was deficient in PYO degradation; additionally, expression of this gene in *Rhodococcus* sp. strain JVH1 allowed PYO degradation by this strain (9). Therefore, MFORT_14352 is necessary for the first step of PYO degradation and may be sufficient for the removal of this phenazine from the medium (9). It was also shown that PYO degradation protects sensitive organisms (9). In particular, *E. coli* DH5α, *S. oneidensis* MR1, and *S. aureus* MN8 grown in presence of 100 μM PYO showed decreased colony growth compared to those grown in absence of PYO (FIG. 26). Further, in all three cases, coculture with WT *M. fortuitum* rescued growth of these organisms, though not always to the same extent as growth in monoculture in the absence of PYO. A *M. fortuitum* PYO degradation mutant provided no protection (9).

Example 2: Biochemical Analysis of the PodA Reaction

In this example, structure and function analysis of the previously uncharacterized protein from *Mycobacterium fortuitum* encoded by MFORT_14352 (NCBI Accession number: EJZ13467) that catalyzes pyocyanin (PYO) degradation (9) were further carried out.

Figure 2G:
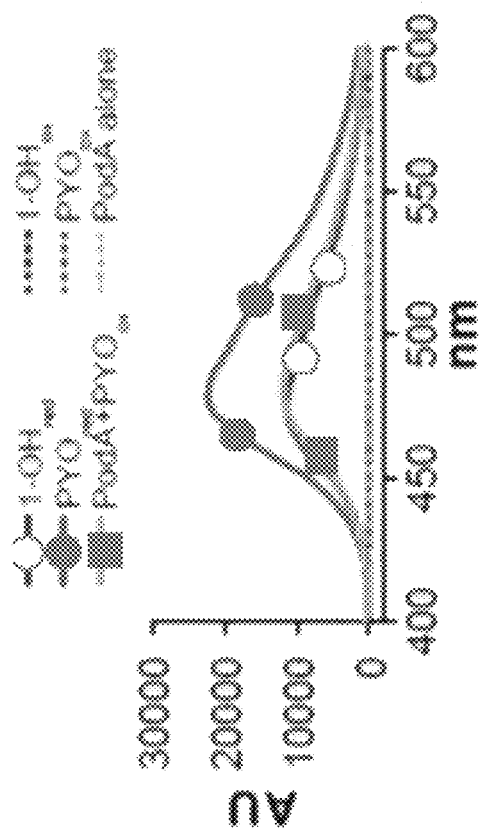
Figure 2C:
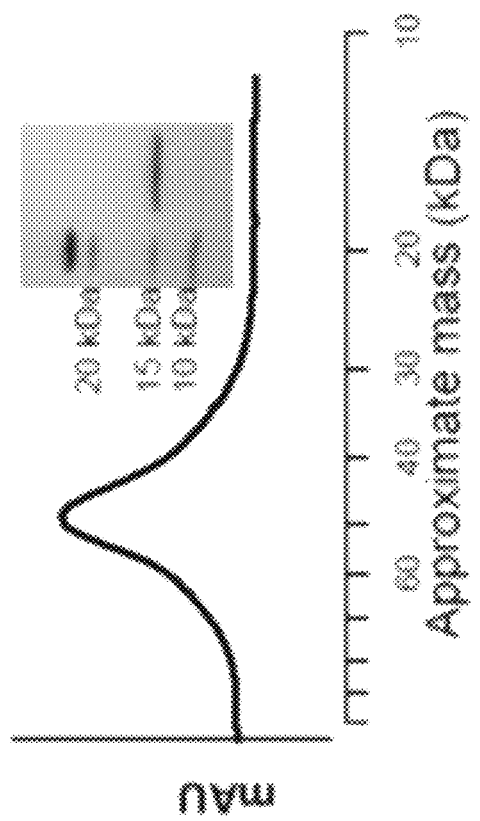
Figure 3:
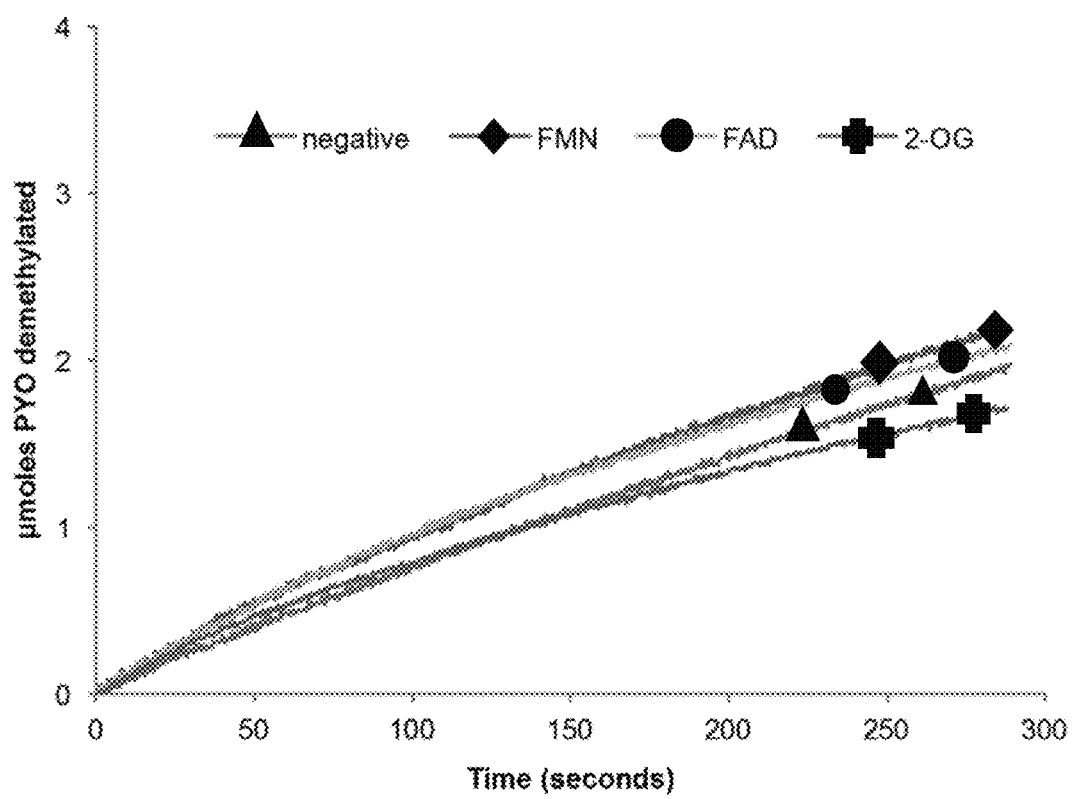
FIG. 3 shows a graph illustrating the results of an exemplary PYO demethylation measured over the time period indicated in the graph, in presence of flavins (flavin mononucleotide, FMN or flavin adenine dinucleotide, FAD) or 2-oxoglutarate (2-OG), showing that $PodA_{30-162}$ activity is not stimulated by the presence of flavins or 2-oxoglutarate (25 µM) in a reaction containing 15 nM $PodA_{30-162}$. Flavins are known cofactors for many demethylases; whereas, several others can utilize 2-oxoglutarate as an electron acceptor.
Figure 4A:
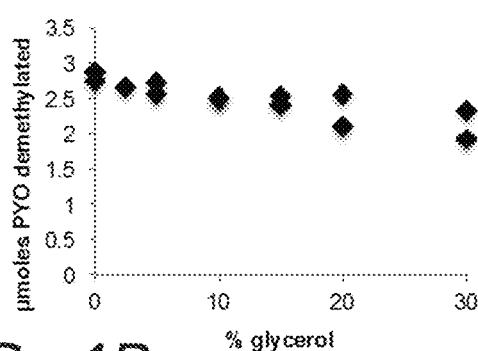
FIGS. 4A-E show charts illustrating the results of exemplary $PodA_{30-162}$-mediated PYO demethylation under the conditions indicated in each chart.
Figure 4B:
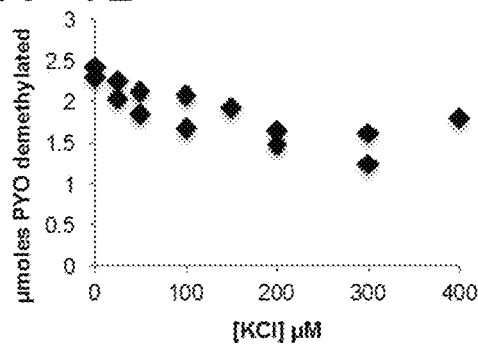
Figure 4C:
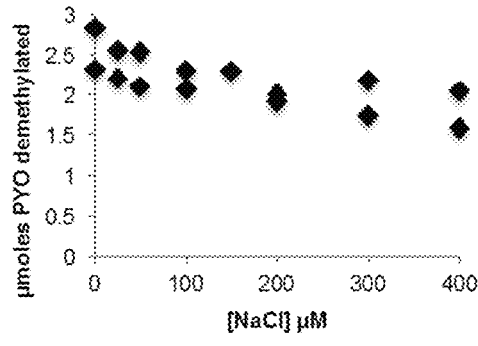
Figure 4D:
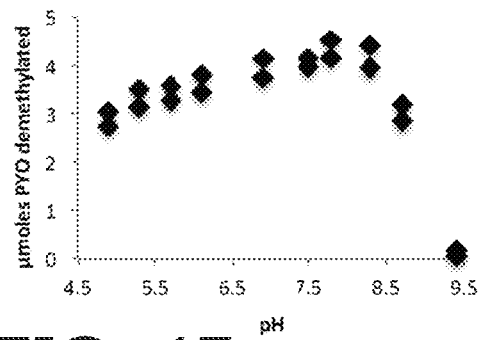
Figure 4E:
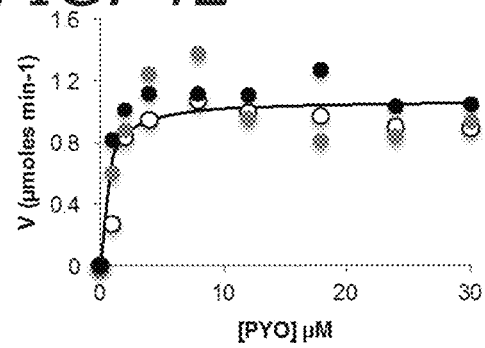
Figure 5:
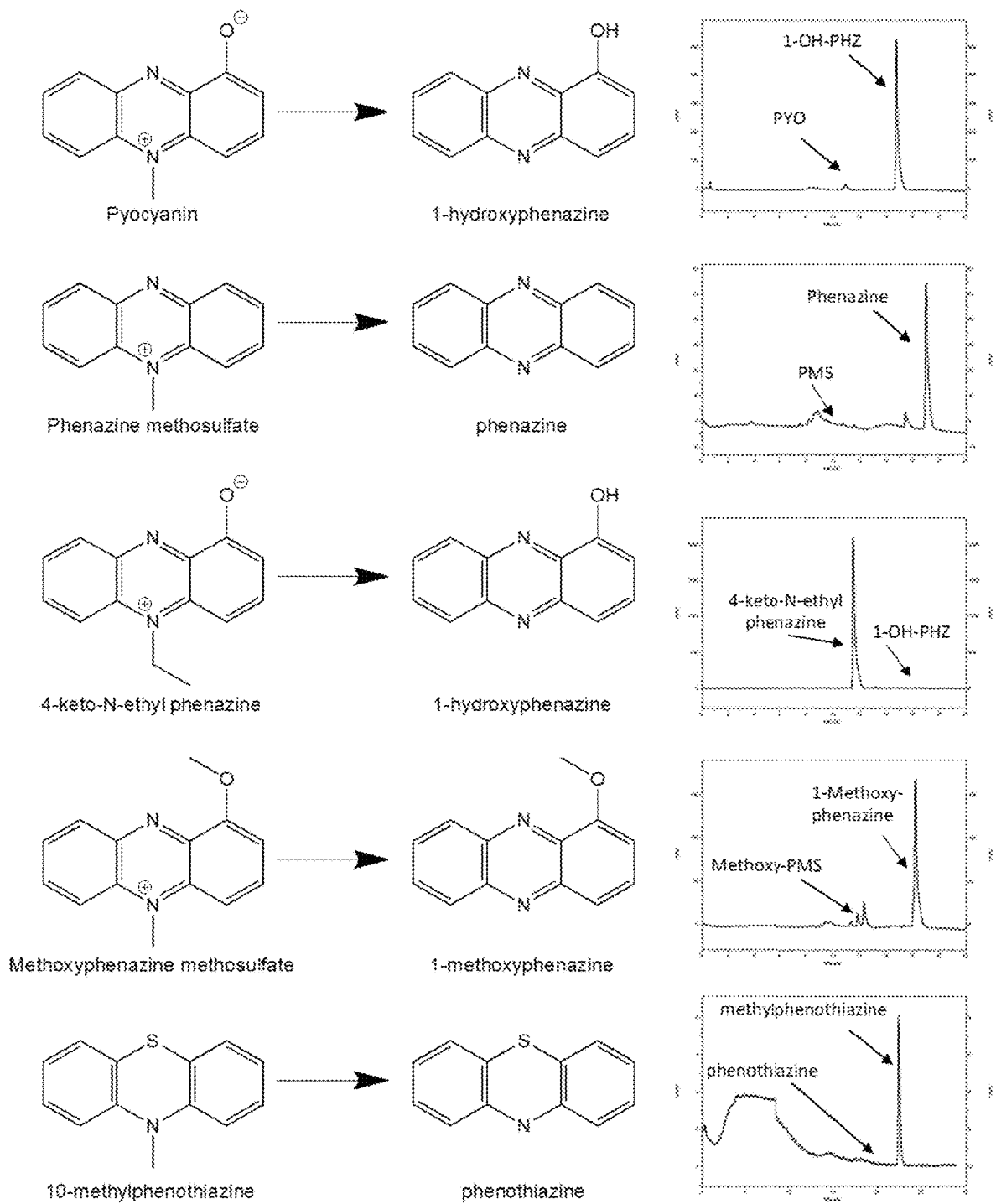
FIG. 5 shows exemplary schematics of alternative substrate utilization by PodA. Chemical formula diagrams of methylated substrates and their expected demethylated products, based on the prediction model, are shown, wherein arrows indicate demethylation catalyzed by PodA. Mixtures were analyzed by HPLC (right graphs) after 4 hours to determine the resulting products of each reaction. Standards for each product were run to determine retention times (indicated for each molecule with arrows). Only N-methylated phenazines were altered by incubation with $PodA_{30-162}$. 4-keto-N-ethylphenazine and 10-methylphenothiazine were not demethylated or de-ethylated. PMS, phenazine methosulfate.
Figure 17:
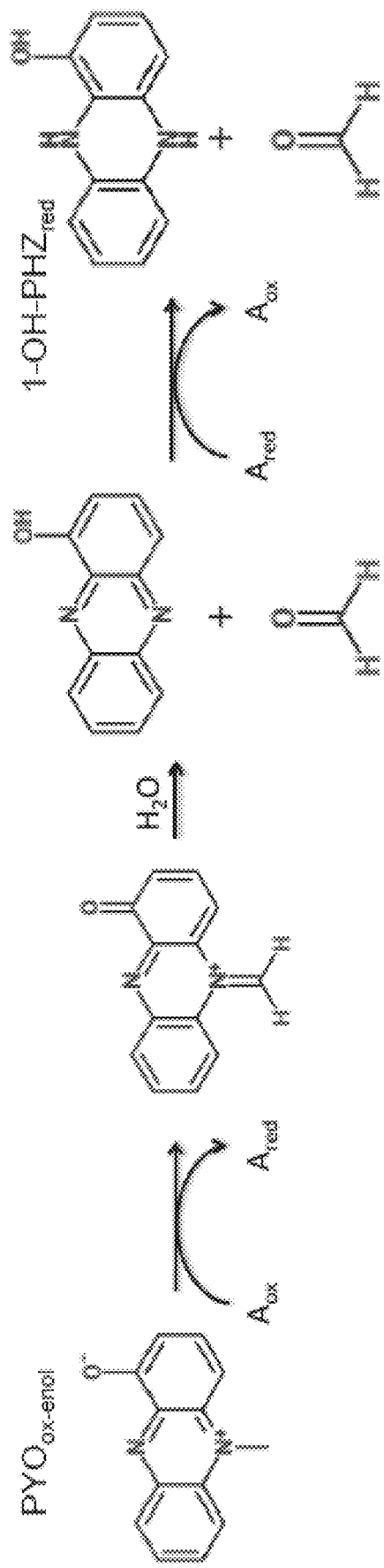
FIG. 17 illustrates a proposed reaction scheme for PYO demethylation by PodA. This scheme is based on the observations of demethylation, formaldehyde formation, and phenazine reduction. "A" indicates an unknown intermediate electron acceptor.
Figure 18A:
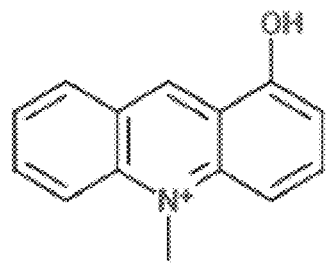
FIGS. 18A-D show chemical structures of exemplary chemical inhibitors for PodA.
Figure 18B:
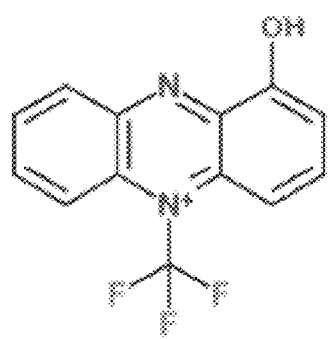
Figure 18C:
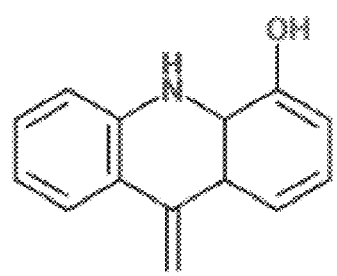
Figure 18D:
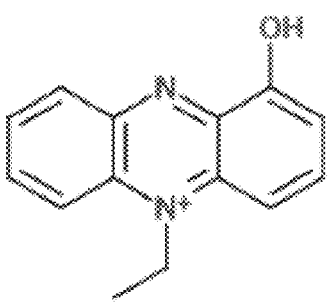
Figure 19:
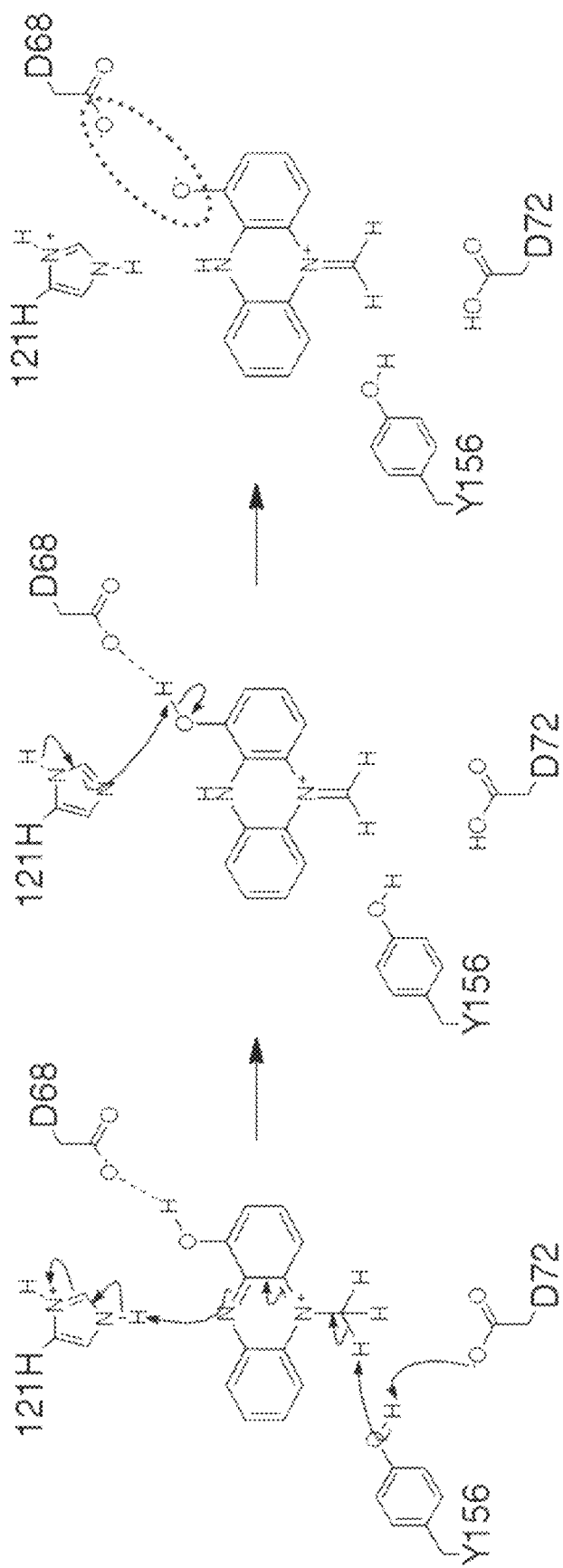
FIG. 19 shows an exemplary model of the PodA mechanism of PYO demethylation. The model predicts that D72 (or E154) and Y156 are necessary for methyl deprotonation. H121 protonates the N that is distal to the methyl group and D68 facilitates the release of the iminium ion via an unfavorable electrostatic interaction (red circle). Hydrolysis of the iminium ion is spontaneous and occurs after release. D72 (or E154) remains protonated, acidifying the active site to protonate PYO in the next catalytic cycle.

To characterize its activity, a heterologously expressed, truncated version of this protein was purified (lacking a predicted N-terminal, membrane-spanning helix (10)), hereafter referred to as PodA$_{30-162}$ (PYO demethylase), from *Escherichia coli* (FIG. 2C). PodA$_{30-162}$ converts PYO to 1-hydroxyphenazine (1-OH-PHZ) and formaldehyde (FIGS. 2D-E), indicating that it functions as a demethylase. Generally, enzyme-catalyzed N-demethylations proceed by oxidation of the methyl group to formaldehyde with electron transfer to a bound cofactor or iron-sulfur cluster (11, 12). Surprisingly, it was found that PodA$_{30-162}$ generates 1-OH-PHZ in the absence of either flavin or 2-oxoglutarate, which are required for most known N-demethylases (FIG. 3). Additionally, PodA$_{30-162}$ functions under anoxic conditions suggesting a mechanism distinct from the oxygen-dependent Rieske-iron type demethylases (13). Kinetic analysis suggests that PodA is a high affinity PYO demethylase (K$_m$<1 μM and k$_{cat}$=1.20±0.07 s$^{-1}$) that operates over a wide regime of pH (<4.9-8.7) and salt concentrations (0-400 mM) (FIG. 4) with specificity for N-methylated phenazines (FIG. 5). Under anoxic conditions, PodA$_{30-162}$ catalyzes the formation of a reduced phenazine, suggesting that its substrate serves as the electron acceptor (FIGS. 2F-G). This mechanism has not previously been observed for demethylases (11, 12). The following reaction for PodA is proposed, wherein oxidized PYO (PYO$_{ox}$) is converted to reduced 1-OH-PHZ (1-OH-PHZ$_{red}$) (FIGS. 2A-B; FIG. 17):

$$C_{13}H_{10}N_2O(PYO_{ox}) + H_2O \rightarrow C_{12}H_{10}N_2O(1\text{-OH-}PHZ_{red}) + CH_2O$$

Example 3: Crystal Structures of PodA$_{30-162}$

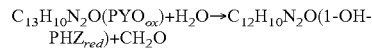

To test the above catalytic model and better understand how PodA$_{30-162}$ reduces its substrate, the X-ray crystal structures of PodA were solved.

Figures 16A, 16B:
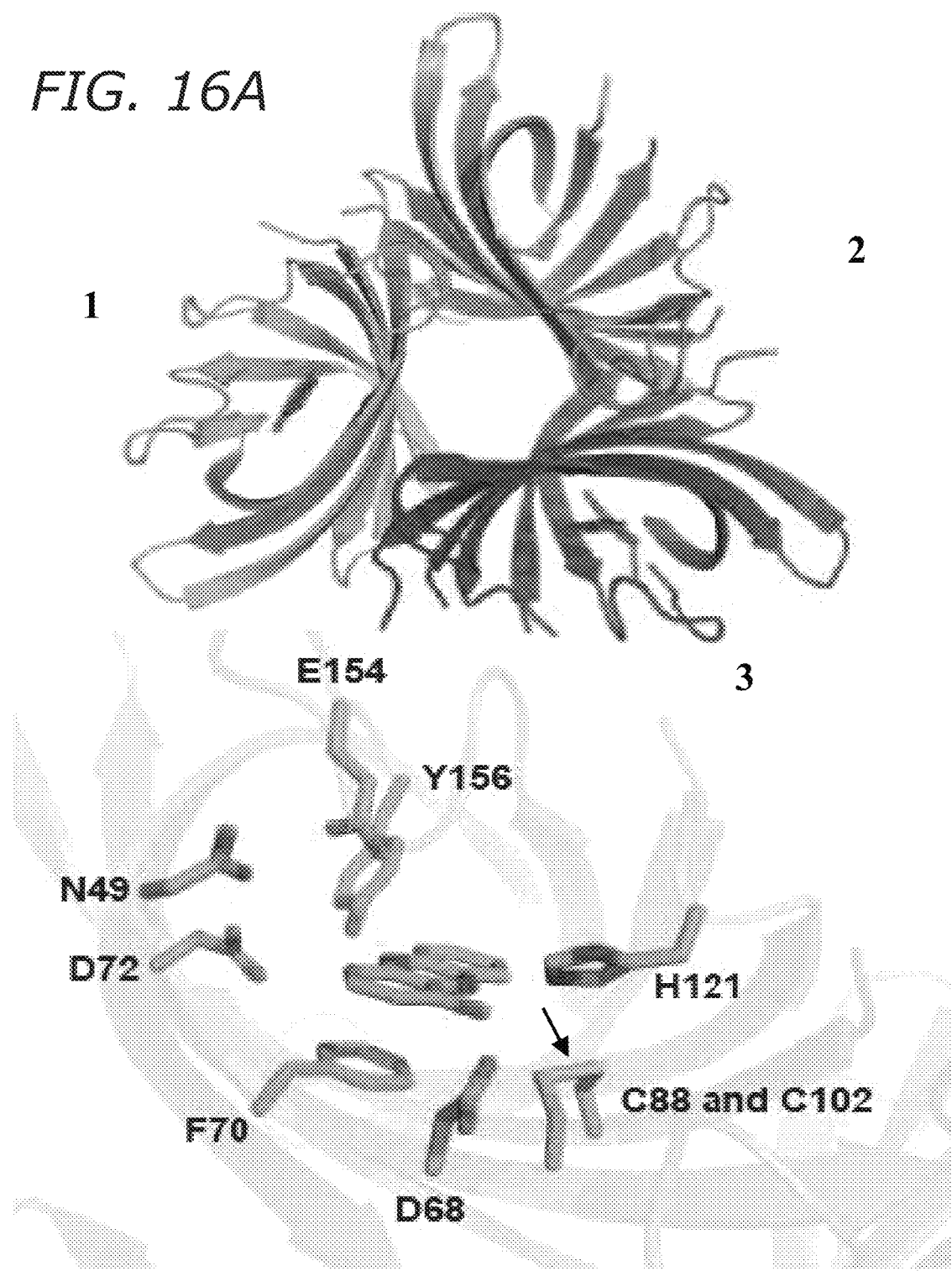
FIGS. 16A-B show a 2.5 Å crystal structure of PodA.

A first crystal structure of PodA was solved using resources provided by the Molecular Observatory at Caltech, headed by Prof. Doug Rees. Crystallization screens (Wizard 1 and 2, Rigaku Reagents and JCSG+, Molecular Dimensions) were performed with 5 mg ml-1 PodA$_{30-162}$ in the presence or absence of 1-OH-PHZox. Crystallization was successful in the presence of 1-OH-PHZox, but not in the presence of PYOox. For wells where crystallization occurred, crystals formed within 3 days. Optimal crystallization conditions matched JCSG+ condition C1 (20% PEG 8000, 100 mM phosphate/citrate pH 4.2, 200 mM NaCl) amended with 200 μM 1-OH-PHZ mixed 1:1 with protein in sitting drop format. X-ray diffraction using the in-house X-ray beam (http://molobs.caltech.edu/) resulted in diffraction to 2.5 Å; crystals belonged to space group p212121. X-ray diffraction data were processed in XDS, run through POINTLESS, AIMLESS, and TRUNATE (Winn M D, et al. (2011) Acta Crystallographica Section D Biological Crystallography 67:235-42; Evans et al. (2011) Acta Crystallographica Section D-Biological Crystallography 67:282-92; Kabsch W. (2010) Acta Crystallographica Section D-Biological Crystallography 66:133-44; Kabsch W. Xds. (2010) Acta Crystallographica Section D-Biological Crystallography 66:125-32; Timms-Wilson et al. (2000) Molecular Plant-Microbe Interactions 13(12):1293-300), and imported to the PHENIX software suite for structure determination (Adams et al. (2010) Acta Crystallographica Section D-Biological Crystallography 66:213-21). The structure was solved using molecular replacement in PHASER-MR (McCoy et al. (2007) 40:658-74) with a structure prediction model from Robetta (Kim et al. (2004) Nucleic Acids Research 32:W526-W31.) and was further refined with phenix.refine to generate a preliminary structure of PodA30-162 (2.5 Å, R-work/R-free: 0.213/0.265). A LigandFit analysis in PHENIX revealed the presence of 1-OH-PHZ in the putative active sites of two of three subunits of the PodA30-162 trimer (correlation coefficients: 0.86 and 0.83, 15/15 atoms placed) (FIGS. 16A-B).

Figure 6:
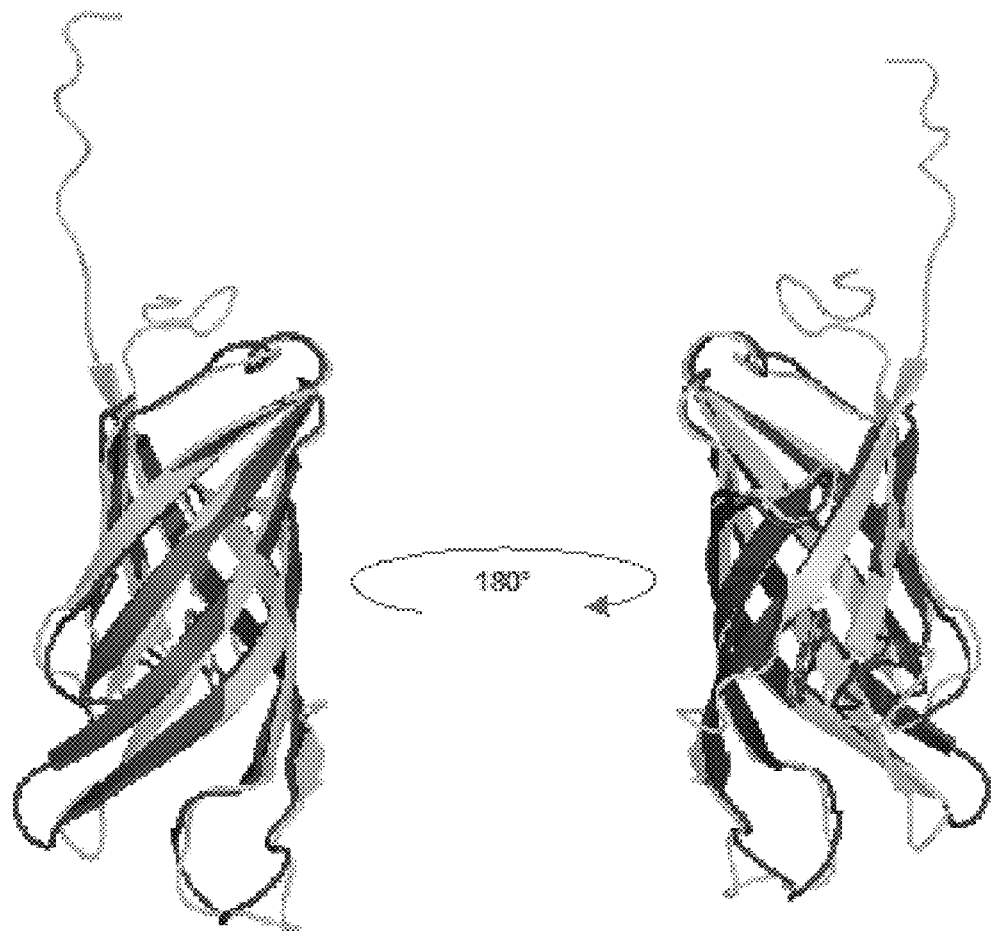
FIG. 6 shows images of an overlay of the Robetta structure prediction model (light gray) with the initial, solved structure of $PodA_{30-162}$ ($R_{free}$=0.22 structure described in the methods) (dark gray). While $PodA_{30-162}$ crystallized as a trimer in the asymmetric unit, only the A chain monomer is shown here. RMSD of the C-alpha backbone: 2.23 Å vs. Robetta prediction. A version of the Robetta prediction model with trimmed loops was used as the search model for molecular replacement (RMSD: 2.11). The N and C terminal extensions on the Robetta prediction were not resolved in the electron density of the solved structure.

A second crystal structure at an increased resolution (1.8 Å) (Table 4) was also solved by molecular replacement using a search model generated by Robetta (14-16) (FIG. 6). In Table 4, two crystals were used for data collection. Values in parentheses are for highest-resolution shell.

TABLE 4

Data collection and refinement statistics for $PodA_{30-162}$

| | |
|---|---|
| Space group | P21 21 21 |
| Cell dimensions | |
| a, b, c (Å) | 65.33, 72.98, 79.7 |
| α, β, γ (°) | 90, 90, 90 |
| Resolution (Å) | 34.98 - 1.8 (1.864 - 1.8) |
| $R_{merge}$ | 0.177 (1.98) |
| $R_{meas}$ | 0.180 (2.01) |
| $R_{pim}$ | 0.036 (0.391) |
| CC1/2 | 0.999 (0.827) |
| I/s(I) | 13.3 (2.3) |
| Wilson B-factor | 24.8 |
| Completeness | 1.00 (1.00) |
| Multiplicity | 25.9 (26.1) |
| No. reflections used in refinement | 35987 (3544) |
| $R_{work}$ / $R_{free}$ | 0.168(0.271) / 0.195(0.283) |
| No. non-hydrogen atoms | 2905 |
| Macromolecules | 2644 |
| Ligands | 48 |
| Average B factor | 36.5 |
| Macromolecules | 36.1 |
| Ligands | 36.4 |
| Solvent | 42.0 |
| R.m.s. deviations | |
| Bond lengths (Å) | 0.007 |
| Bond angles (°) | 0.94 |
| Ramachandran plot statistics (%) | |
| Favored | 98 |
| Allowed | 2.5 |
| Outliers | 0 |

$PodA_{30-162}$ crystalized as a trimer in the asymmetric unit (FIG. 7A). Crystal formation occurred only in the presence of 1-OH-PHZ, which was visible in a putative solvent-exposed active site (FIGS. 7B-C). No evidence was found of a bound cofactor or metals in the electron density of the active site (FIG. 8), further supporting the hypothesis that PodA catalyzes a novel demethylation reaction. Within the active site, there are several charged and polar residues (D68, D72, H121, E154, and Y156) and a nearby disulfide that are candidate catalytic residues (17); additionally, 1-OH-PHZ appears to bind via a π-π stacking interaction with F70 (FIG. 7B).

Figure 7D:
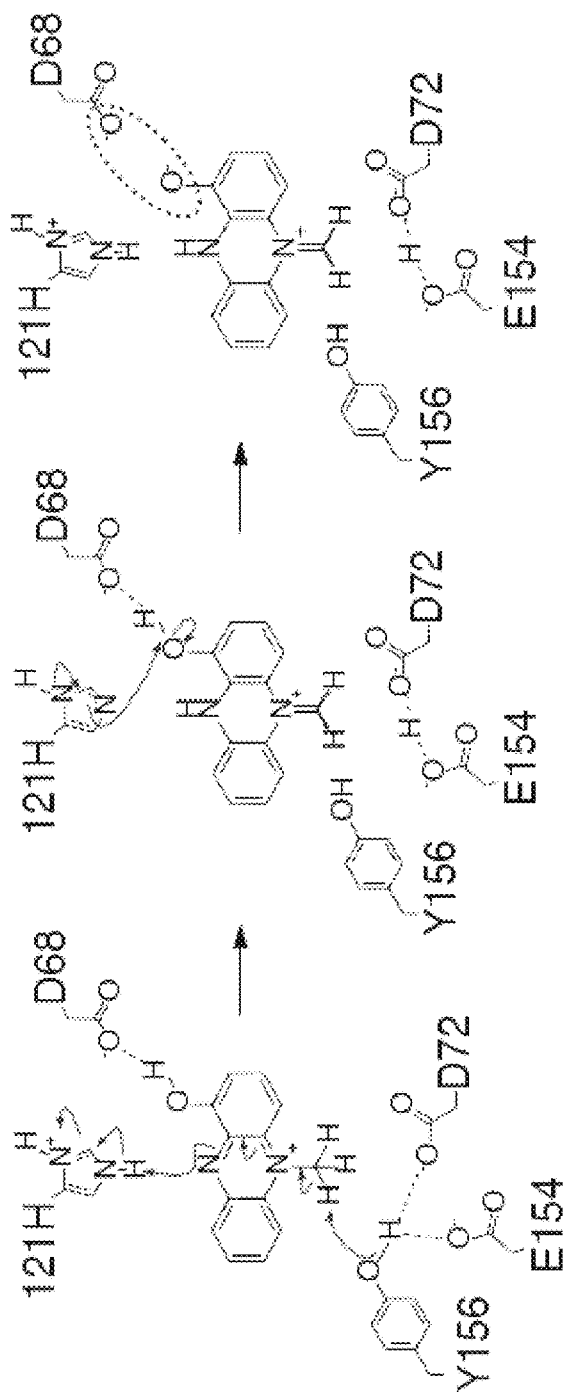
FIGS. 7D-E shows a proposed reaction mechanism based on the residues present in the active site. The model predicts that D72, E154 and Y156 are necessary for methyl deprotonation. H121 protonates the unmethylated N atom of the pyrazine ring, and D68 reprotonates H121. Formation of the negatively charged phenolate ion promotes product release due to an unfavorable electrostatic interaction (dashed circle). D72 and E154 remain protonated, acidifying the active site to assist in formation of hydroxylated PYO (FIG. 7D) in the next catalytic cycle.
Figure 7E:
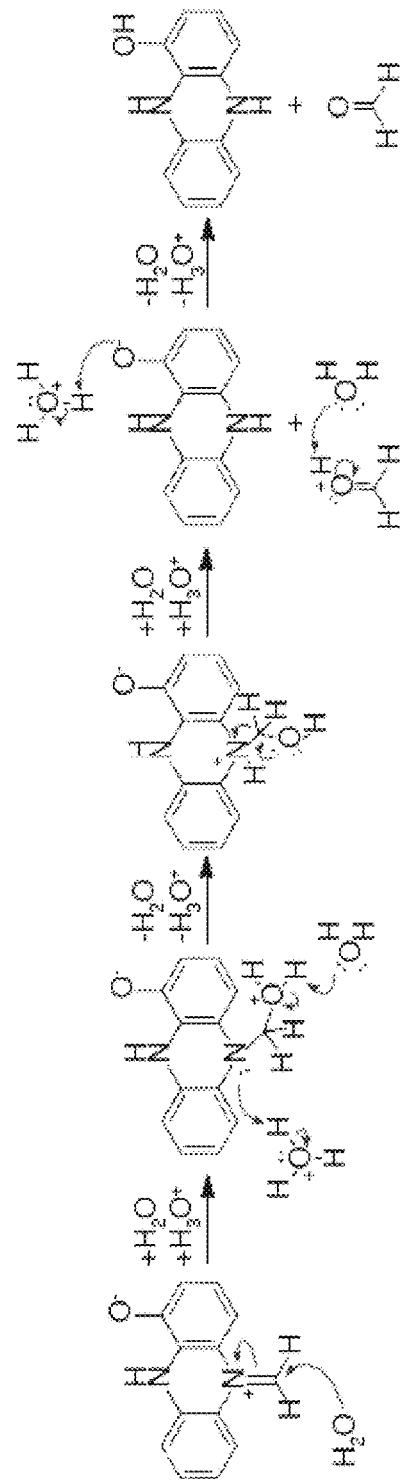

Based on the active site structure, a mechanism is proposed relying on the presence of H121 functioning as an acid and D72, E154 and Y156 collectively functioning as a base (FIG. 7D). PYO binds in the phenol tautomeric form (FIG. 2A). Deprotonation of the methyl group results in iminium ion formation and concomitant reduction of the pyrazine ring, with the second nitrogen atom protonated by H121. H121 is then reprotonated by PYO's hydroxyl group ($pK_a$ of His ~6 versus PYO ~5). The unfavorable interaction between the negatively charged phenolate ion and D68 drives product release. It is hypothesized that PodA catalyzes the tautomerization of PYO to an iminium ion that is susceptible to hydrolysis outside of the enzyme: the structure indicates that the active site cannot accommodate both the substrate and a water molecule (FIGS. 7B-E) (11). D72 and E154 remain protonated in this scenario, acidifying the active site, perhaps to ensure that PYO is in the hydroxylated form in subsequent reaction cycles (FIG. 2A). This scheme highlights the significance of the hydroxyl group of PYO to recharge PodA for subsequent reaction cycles and to drive product release. An alternative substrate, methoxyphenazine methosulfate (methoxy-PMS), which lacks the hydroxyl group, displays an initial burst of activity followed by a slower steady state (FIG. 9A), which is consistent with the proposed model.

Example 4: Mutagenesis of the Putative Catalytic Residues in PodA

To probe the proposed mechanism, mutagenesis for each of the catalytic residues were performed. Table 5 lists residues in the active site of particular interest (FIG. 16B; FIG. 7B), along with hypotheses regarding their possible role in PYO demethylation.

TABLE 5

Hypothesized roles of residues in the PodA active site.

| Residue | Charge | Role | Description |
|---|---|---|---|
| D68 | negative | catalysis | Hydrogen bond the hydroxyl group of PYO |
| F70 | — | binding | pi-pi stacking with PYO or 1-OH-PHZ |
| D72 | negative | catalysis | Possibly extracts a proton from PYO's methyl |
| C88 | polar | redox | Forms disulfide with C102 |
| C102 | polar | redox | Forms disulfide with C88 |
| H121 | polar | catalysis | Stabilize a redox intermediate |
| E154 | negative | catalysis | Possibly extracts a proton from PYO's methyl |
| Y156 | polar | catalysis | Possibly extracts a proton from PYO's methyl |

For example, aromatic molecules often possess non-covalent, attractive interactions via π-π stacking mediated by electrons in the π-orbitals of the rings. Therefore, residue F70 (only ~4 Å from the central aromatic ring of 1-OH-PHZox) may facilitate a binding interaction with PYOox and 1-OH-PHZox, releasing 1-OH-PHZred when the central ring is no longer aromatic.

Figures 9C, 9D:
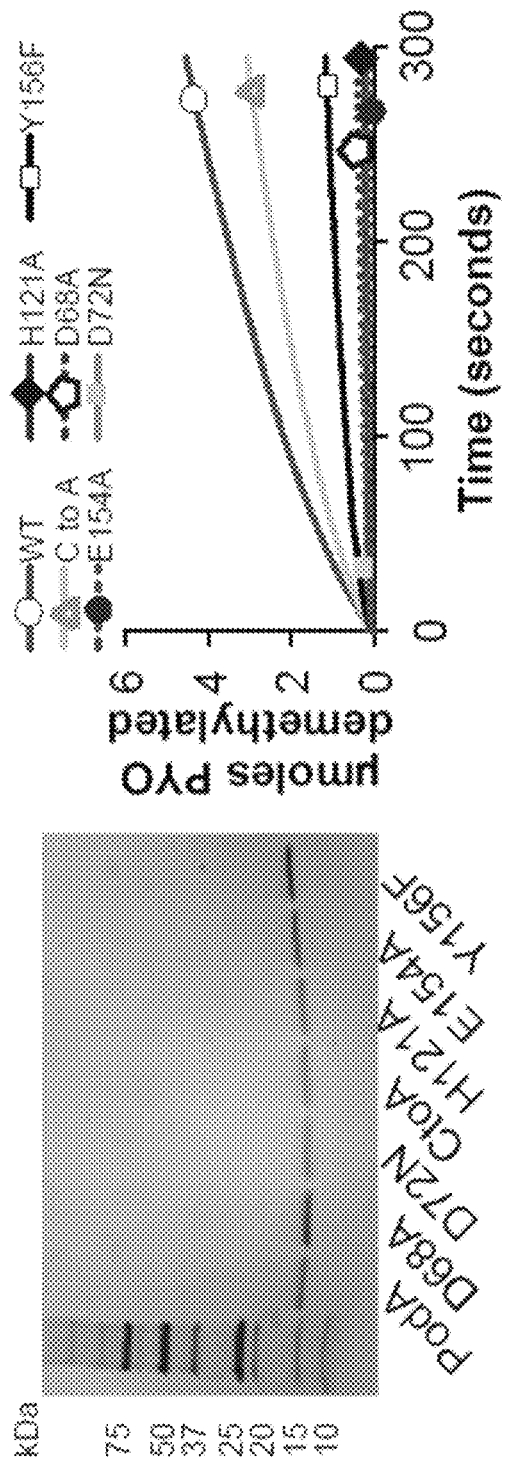
Figure 10A:
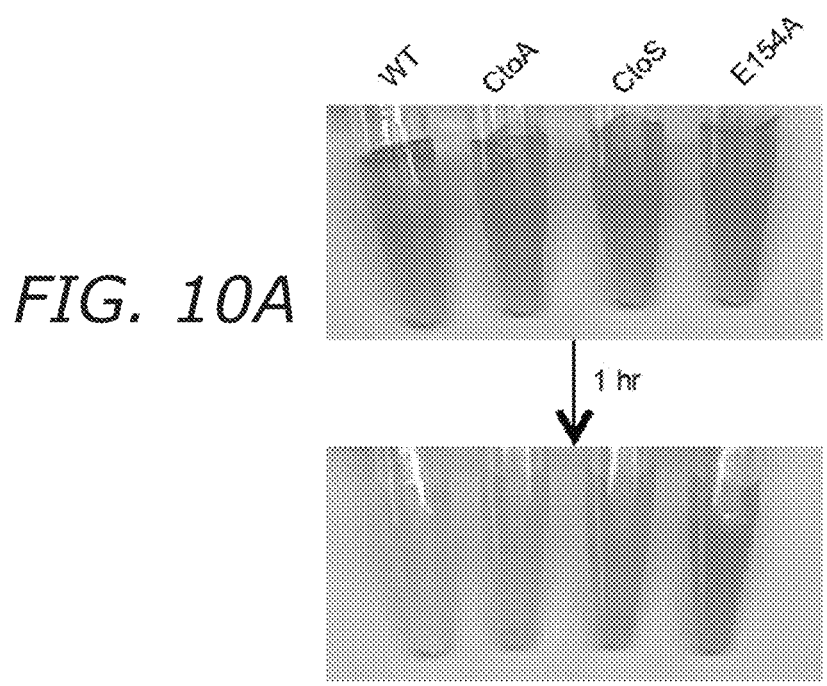
FIG. 10A shows photographs of exemplary microcentrifuge tubes containing cell-free *E. coli* lysates containing PYO substrate and the indicated PodA WT and mutants, before and after 1 hour incubation time (arrow). Greater demethylase activity of PodA is shown for the lighter grey shaded reaction mixtures in tubes in the lower panel after 1 hour incubation. Both the C to A (C88A, C102A) and a C to S (C88S, C102S) double mutants show activity in cell-free lysates of *E. coli* BL21(DE3) expressing the protein of interest. While activity was always apparent in cell-free lysates, it was unstable and often lost upon further purification. (Note: the data for the C to A mutation in FIGS. 9A-D are from a rare preparation where protein remained active throughout purification.) C to S has less apparent activity than C to A, but serves as an independent confirmation of the phenotype. Cell lysates of the E154A mutant show that the loss of PYO is not due to an activity inherent to *E. coli*; furthermore, the accumulation of 1-OH-PHZ by both C to A and C to S lysates was confirmed by HPLC.
Figure 10B:
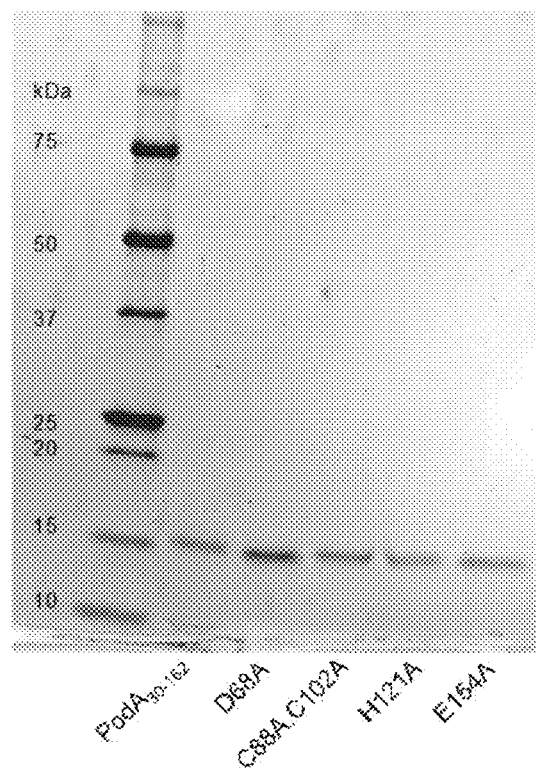
FIG. 10B shows an exemplary reducing SDS-PAGE of mutant PodA$_{30-162}$ proteins indicated and FIG. 10C shows an exemplary non-reducing SDS-PAGE of mutant PodA$_{30-162}$ proteins indicated. Under reducing conditions, PodA$_{30-162}$ and mutant proteins all have similar migration through SDS-PAGE. Under non-reducing conditions, the presence of a disulfide bond leads to slightly faster migration through SDS-PAGE for all proteins except the C to A double mutant.
Figure 10C:
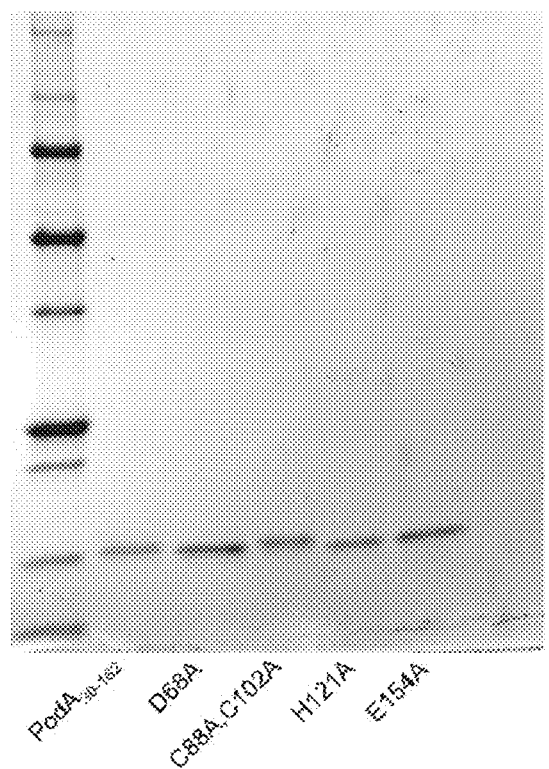

H121A, E154A, D68A, and D72N mutants all formed a trimer (FIGS. 9B-C) but had <10% wild type activity, consistent with the postulated catalytic mechanism (FIG. 9D). Y156F formed a trimer but retained ~25% wild type activity, consistent with this residue facilitating proton transfer to D72 and E154 but not being essential. A possible alternative mechanism could utilize the disulfide in the active site forming a covalent adduct with the phenazine, in analogy to some flavoproteins (18). However, the mutagenesis results indicate that the disulfide bond near the active site is not essential for catalytic activity although it may be important for structural stability (FIGS. 9B-D and FIG. 10).

Example 5: $PodA_{30-162}$ Inhibits Biofilm Formation and Anoxic Fitness of P. Aeruginosa In this example, the impact of PodA on biofilm formation and anoxic fitness of P. aeruginosa was assessed.

Figure 11A:
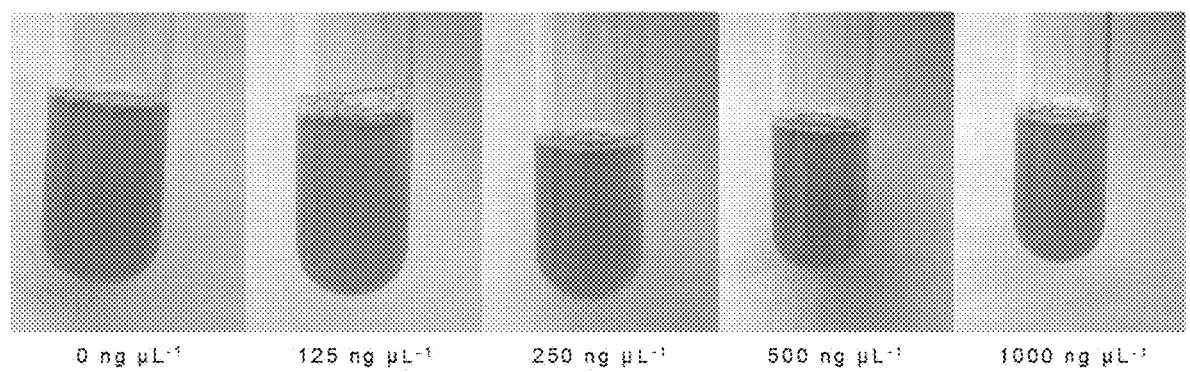
FIG. 11A shows photographs of exemplary *P. aeruginosa* culture tubes showing the dose dependence of PodA$_{30-162}$ activity of PYO demethylation in overnight cultures grown in TSB in the presence of the indicated amount of enzyme. PodA$_{30-162}$ enzyme was added at the start of the culture and remained stable throughout the incubation period. The tubes with PodA$_{30-162}$ enzyme turned into yellow compared with the tube with no PodA$_{30-162}$ enzyme in blue.
Figure 11B:
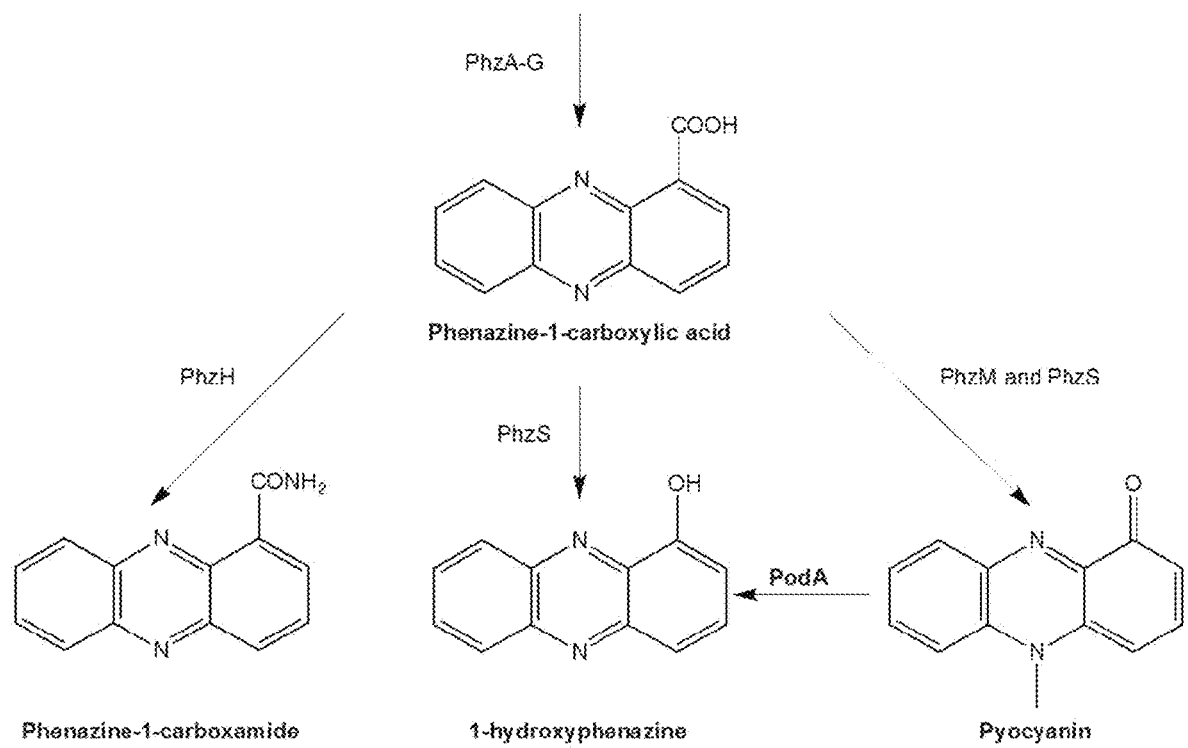
FIG. 11B shows the phenazine biosynthetic pathways of *P. aeruginosa* (40), showing the chemical formulas of the indicated substrates and the indicated enzymes that catalyze reactions (arrows).
Figure 12F:
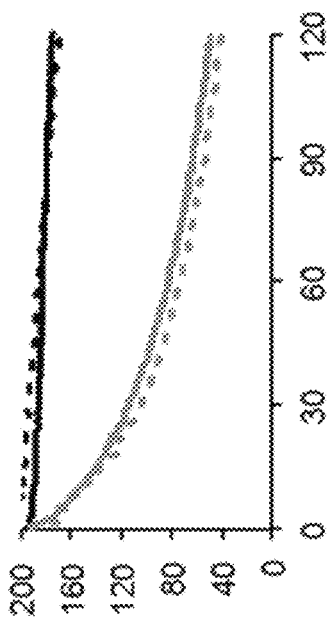
Figures 12D, 12E:
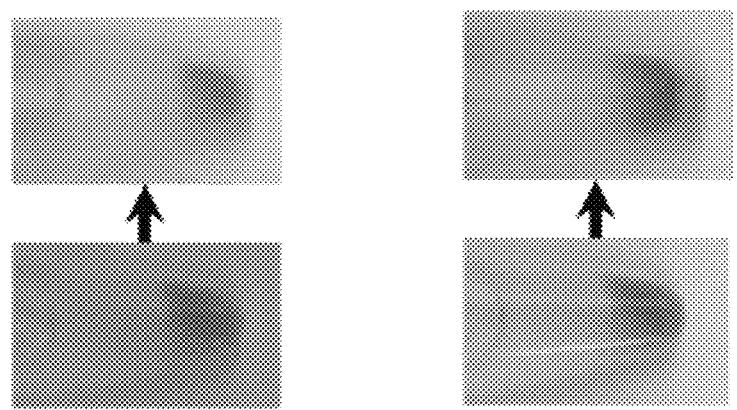
Figure 12C:
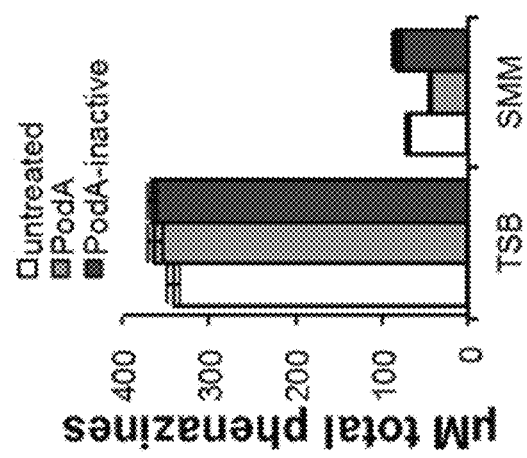
Figure 29A:
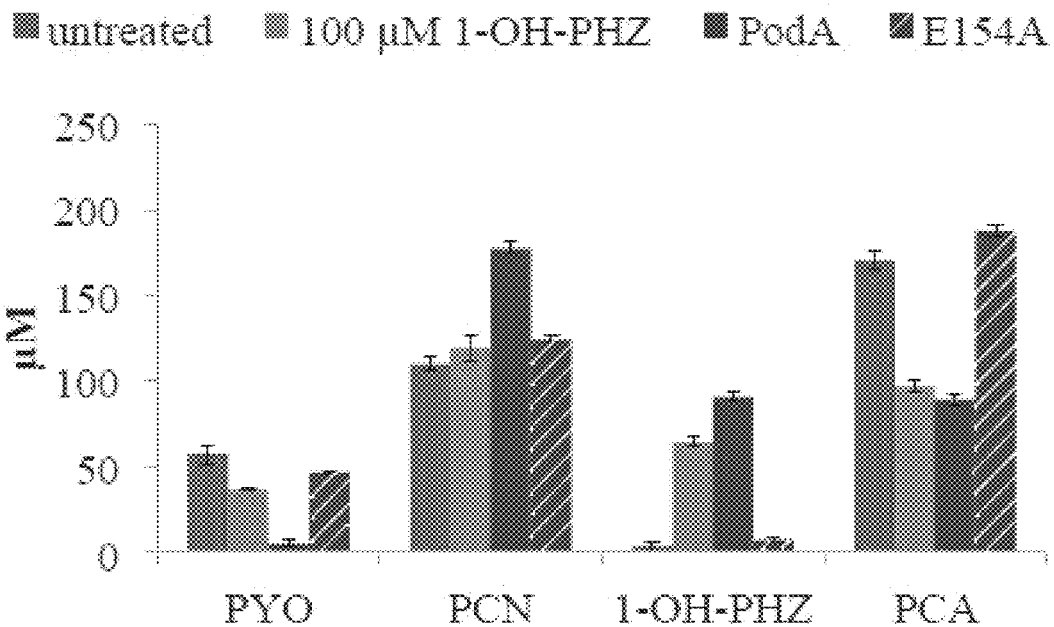
FIG. 29A shows exemplary graphed results of phenazine production by P. aeruginosa grown on tryptic soy broth for 24 hours under the indicated conditions. PodA or 1-OH-PHZ addition results in changes to the concentrations of all four phenazines.
Figure 29B:
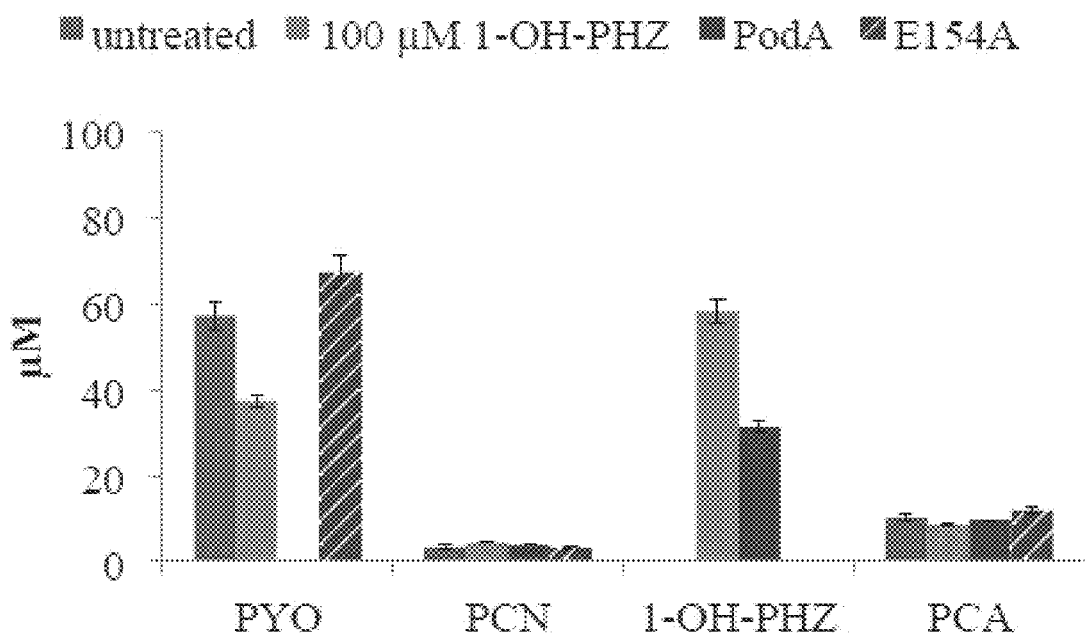
FIG. 29B shows exemplary graphed results of phenazine production by P. aeruginosa grown on minimal medium with succinate as the sole carbon source for 24 hours under the indicated conditions. 1-OH-PHZ has a negative impact on the production of PYO.

PodA requires only water and substrate for activity (FIGS. 7D-E, and FIG. 3, and FIGS. 4A-E), therefore it was hypothesized that it could degrade PYO during active production by P. aeruginosa (FIGS. 11A-B). $PodA_{30-162}$ addition to P. aeruginosa planktonic culture also results in the conversion of PYO to 1-OH-PHZ in both rich and minimal medium (FIGS. 12A-F; FIGS. 29A-B).

Extracellular DNA (eDNA) comprises >50% of the P. aeruginosa biofilm matrix (19), and recently PYO was shown to drive eDNA release (20, 21) which is important early in biofilm development (19). It was hypothesized that $PodA_{30-162}$ might inhibit P. aeruginosa biofilms in part by attenuating DNA release, thereby removing an important matrix component and changing biofilm architecture. Because PYO does not completely block DNA release (20, 21), it is also possible that downstream PYO-DNA interactions may be important. Experiments were performed to check whether PodA$_{30-162}$ could access PYO in the presence of DNA, as PYO is a known DNA intercalator (22); PodA$_{30-162}$ catalyzed PYO demethylation in this context (FIGS. 12A-F). *P. aeruginosa* biofilms were grown for 5 hours, staining them with DAPI to image biofilm structure. HPLC analysis of supernatants confirmed the conversion of PYO to 1-OH-PHZ by PodA$_{30-162}$ in these cultures (FIGS. 13A-H). Overall biofilm formation, as assayed by surface coverage (22), was reduced by PodA$_{30-162}$ but not by the inactive PodA control (FIGS. 13B-D), consistent with a role for PYO in early biofilm development. As previously shown, treatment with DNase independently inhibited biofilms (22). Interestingly, DNase or PodA$_{30-162}$ treatment inhibited biofilms to the same extent, and dual treatment did not have an additive effect (FIG. 13D).

In addition to impacting early stages in biofilm development, phenazines can expand the habitable zone within established biofilms (5, 23). As *P. aeruginosa* biofilms mature, cells in deeper layers of the biofilm begin to experience oxygen limitation and redox stress (4, 23); these cells are believed to be slow growing and are highly resistant to antibiotics (24). Phenazines facilitate anoxic survival and alleviate redox stress (3, 25). Because PYO reacts with oxygen more efficiently than 1-OH-PHZ (26), it was hypothesized that PodA activity might decrease anoxic fitness by disrupting PYO dependent electron shuttling to oxygen.

Figure 13F:
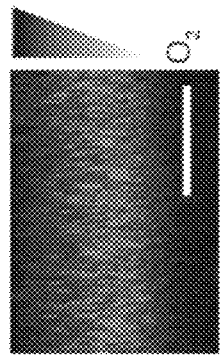
Figure 13G:
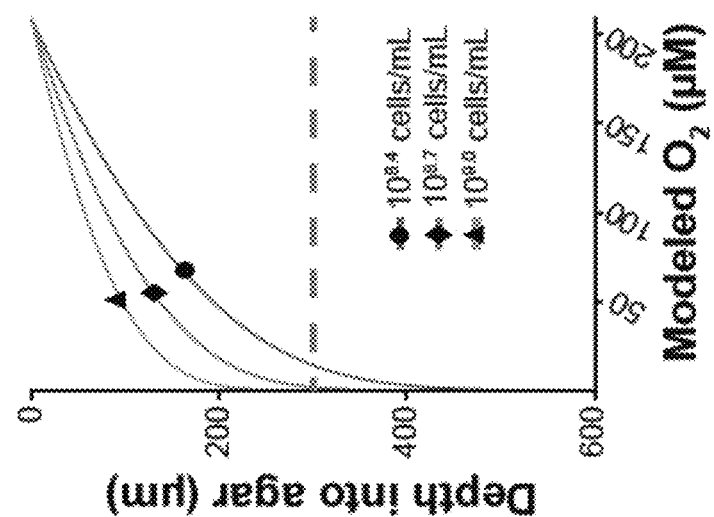
Figure 13H:
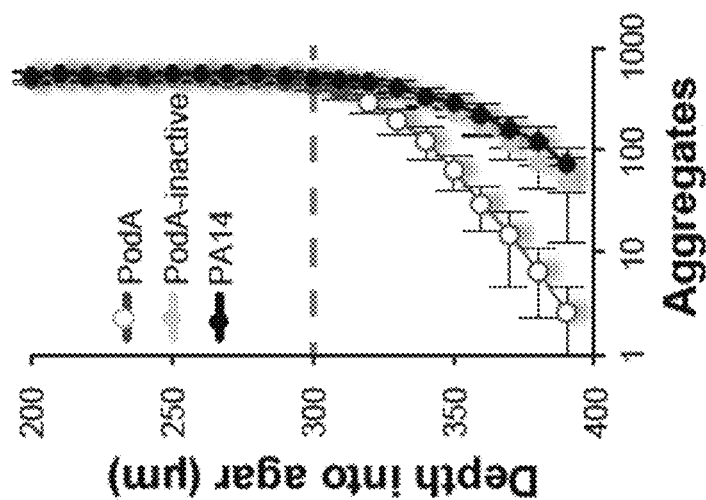
Figure 14A:
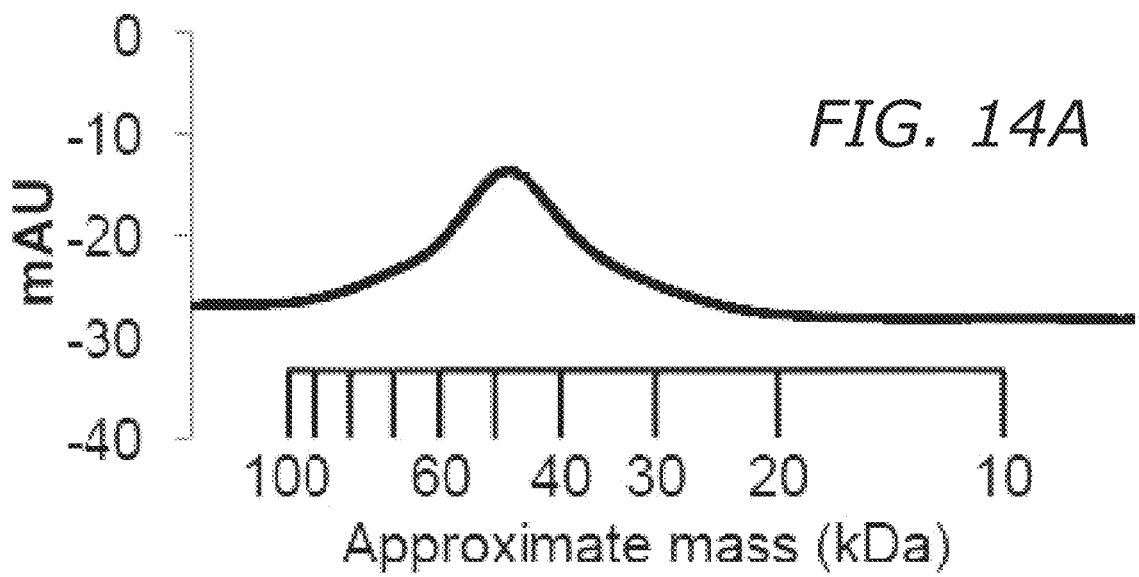
FIGS. 14A-C show charts and images illustrating exemplary experiments showing purification and activity of PodA.
Figure 14C:
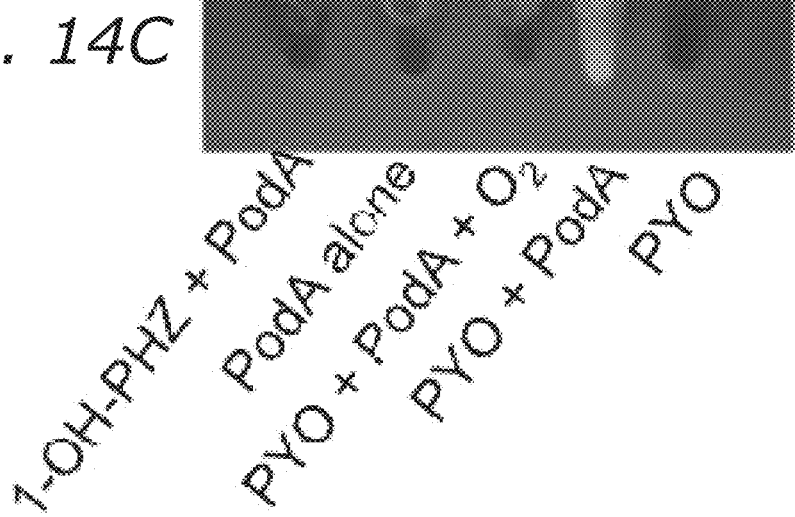
Figure 14B:
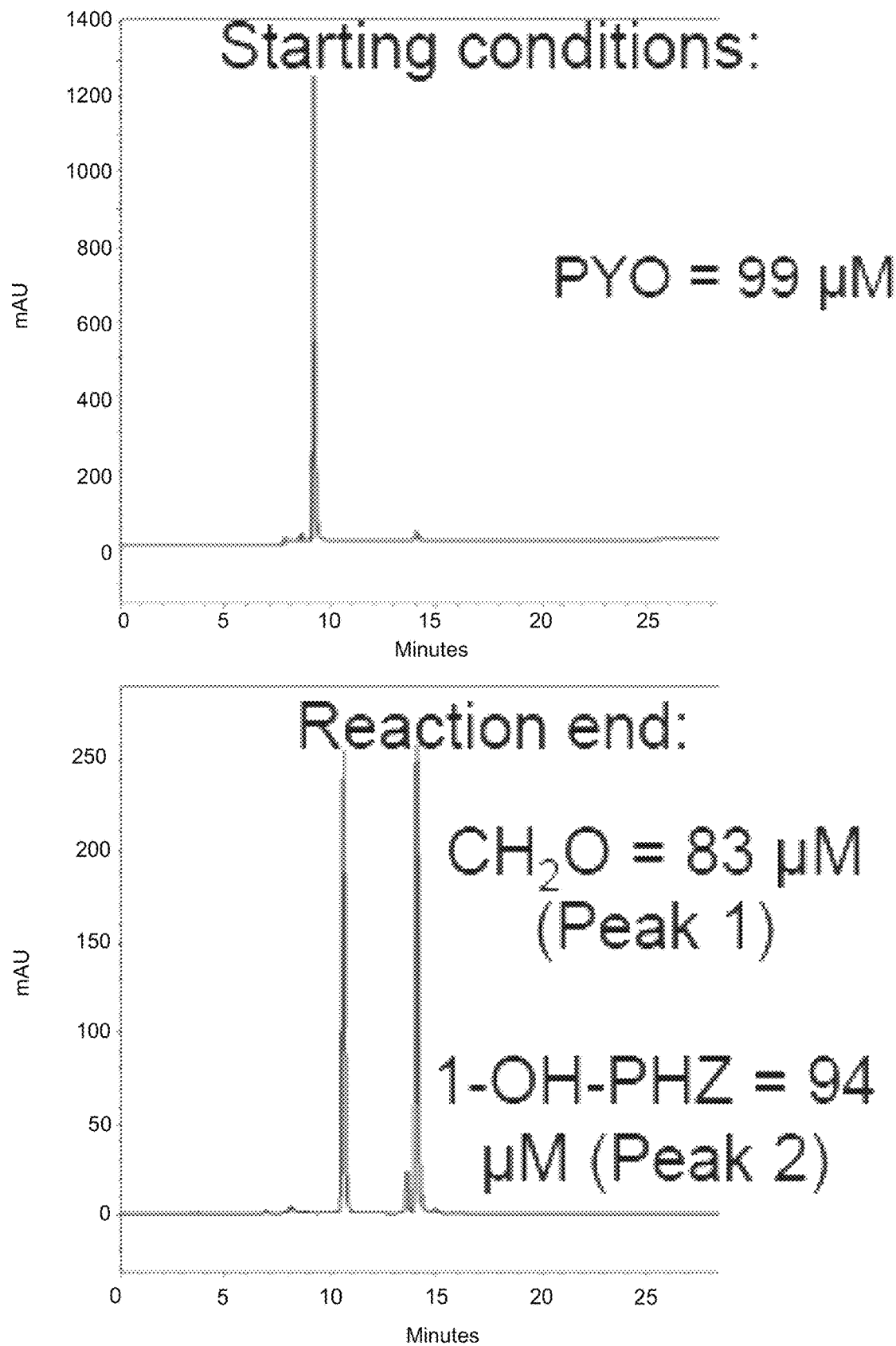

To capture key features of in vivo biofilm aggregates (27, 28), cells were grown suspended in agar blocks at 37° C. for 22 hours to establish an oxygen gradient before a 5 hour treatment with PodA$_{30-162}$ (FIGS. 13E-F). Owing to constraints imposed by the incubator, oxygen gradients cannot be measured directly, so a previously validated model to estimate the oxic-anoxic transition zone was used (29). Modeling the aggregate population indicated that anoxia occurs ~300 µm below the surface as a result of microbial consumption (FIG. 13G), consistent with what is known about oxygen diffusion into in vivo biofilms (29). A decrease in detectable aggregates at depths 300-400 µm below the agar surface were observed; additionally, cultures treated with PodA$_{30-162}$ had a sharper decline in detectable aggregates below this depth (FIG. 13H). There was no significant difference in aggregate numbers above the predicted oxic-anoxic transition zone. How PYO demethylation restricts the aggregate population is unknown.

Figure 27B:
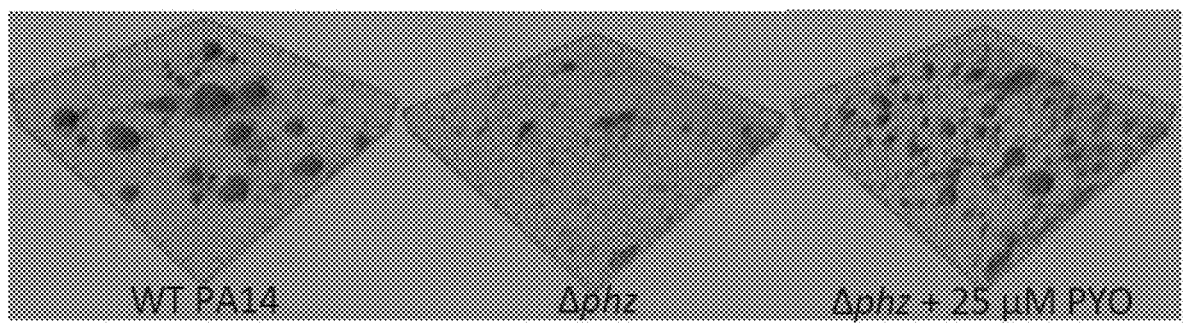
FIG. 27B shows biofilm formation by WT P. aeruginosa (WT PA14), a phenazine deficient strain (Δphz), and by Δphz supplemented with 25 μM PYO (Δphz+ 25 μM PYO). (Images from reference Ramos et al., 2010. Res. Microbiol. 161: 187-91.) The results suggest that biofilm maturation is dependent on PYO.

The following Figures show additional examples of the action of PodA in inhibiting biofilm formation: FIG. 27B shows that biofilm maturation is dependent on PYO, as decrease in biofilm production in a phenazine-deficient strain of *P. aeruginosa* Δphz is restored by supplementation with 25 µM PYO.

FIGS. 28A-B show that optical density of *P. aeruginosa* biofilm is significantly decreased in presence of active PodA compared to inactive E154A mutant PodA, whereas the optical density of *P. aeruginosa* biofilms grown in presence of 1-OH-PHZ were not significantly different to biofilms grown in presence of control treatment 1% DMSO.

Figure 25:
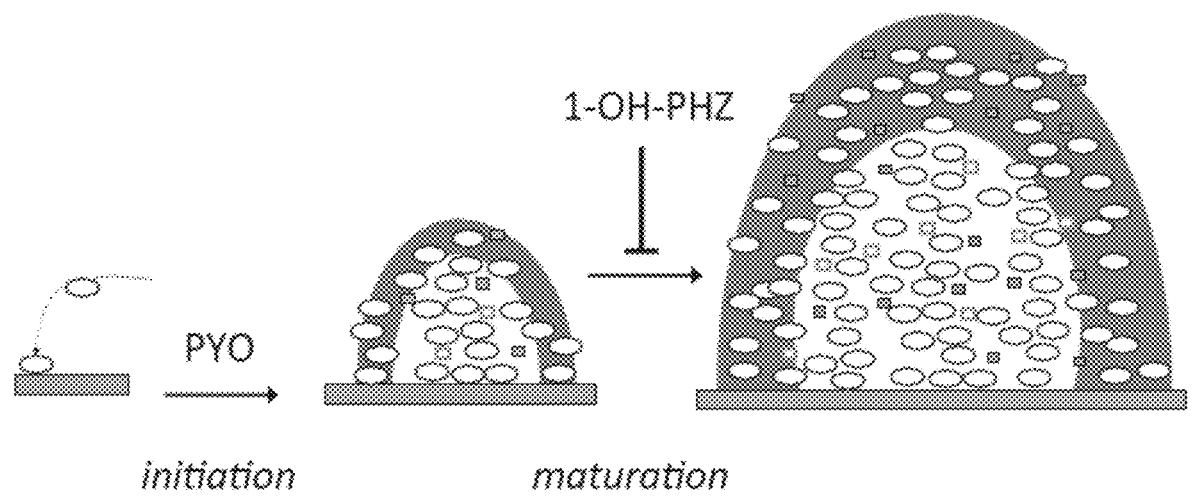
FIG. 25 shows a diagram of illustrating possible different ways in which PYO loss and 1-OH-PHZ accumulation inhibit biofilms.

FIGS. 24A-C show PodA and 1-OH-PHZ inhibit the early stages of *P. aeruginosa* biofilm formation on succinate minimal medium. In particular, compared to treatment with inactive mutant PodA E154A, treatment with active PodA decreases both the number of microcolonies formed (FIG. 26B) and also the microcolony diameter (FIG. 26C). In contrast, 1-OH-PHZ treatment does not significantly affect the number of microcolonies formed (FIG. 26B), but does decrease the microcolony diameter FIG. 26C). Thus, it is suggested that PYO loss and 1-OH-PHZ accumulation inhibits biofilms in different ways, as illustrated in FIG. 25, where 1-OH-PHZ inhibits biofilm maturation, whereas PYO loss also inhibits biofilm initiation.

The discovery of a PYO demethylase that simultaneously catalyzes substrate reduction shows that redox-active pigments can participate in their own enzyme-catalyzed modification. Though PodA is the first member of a new class of tautomerizing demethylases that utilizes an oxidized substrate as the electron acceptor, this reaction is reminiscent of reduced flavin acting as the electron donor in its own destruction in vitamin B$_{12}$ biosynthesis (30). It seems likely that the processing of other redox-active pigments and cofactors may operate by a similar mechanism where the redox activity of the substrate enables catalysis. That PodA can inhibit *P. aeruginosa* at different stages of biofilm development raises the possibility that selective degradation of extracellular electron shuttles may facilitate treatment of intractable infections.

Example 6: Homology Analysis of PodA to Known Demethylases

Figure 15B:
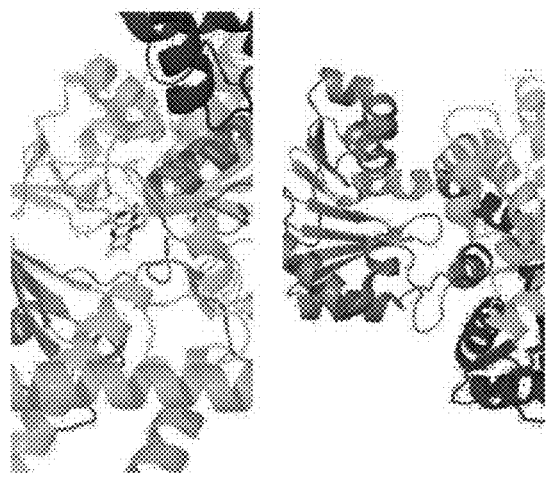
FIGS. 15A-B show schematics illustrating phylogenetic distribution and analysis of PodA homologs.

One of the best-studied types of demethylases are histone demethylases from eukaryotes whose post-translational modifications affect key DNA regulatory processes (Cloos et al. (2008) Genes Dev. 22(9):1115-40). Of these, the lysine-specific demethylases are an important class, with LSD1 being a conserved archetype present in organisms ranging from yeast to human (Anand et al. (2007) J Biol Chem 282(49):35425-9). Its C-terminal AOL (amine oxidase-like) domain catalyzes lysine demethylation and is homologous to polyamine oxidases that belong to the FAD-dependent enzyme family (Anand et al. (2007) J Biol Chem 282(49): 35425-9). The AOL domain contains two subdomains, a FAD-binding subdomain and a substrate-binding subdomain (Anand et al. (2007) J Biol Chem 282(49):35425-9). Though phenazines are structurally similar to flavins, the AOL catalytic domain is quite distinct from that of PodA (FIG. 15B and FIG. 7B), as is the bacterial PhzM protein, which adds a methyl group to phenazine-1-carboxylic acid in PYO biosynthesis (Parsons et al. (2007) Biochemistry 46(7): 1821-8).

Figure 15A:
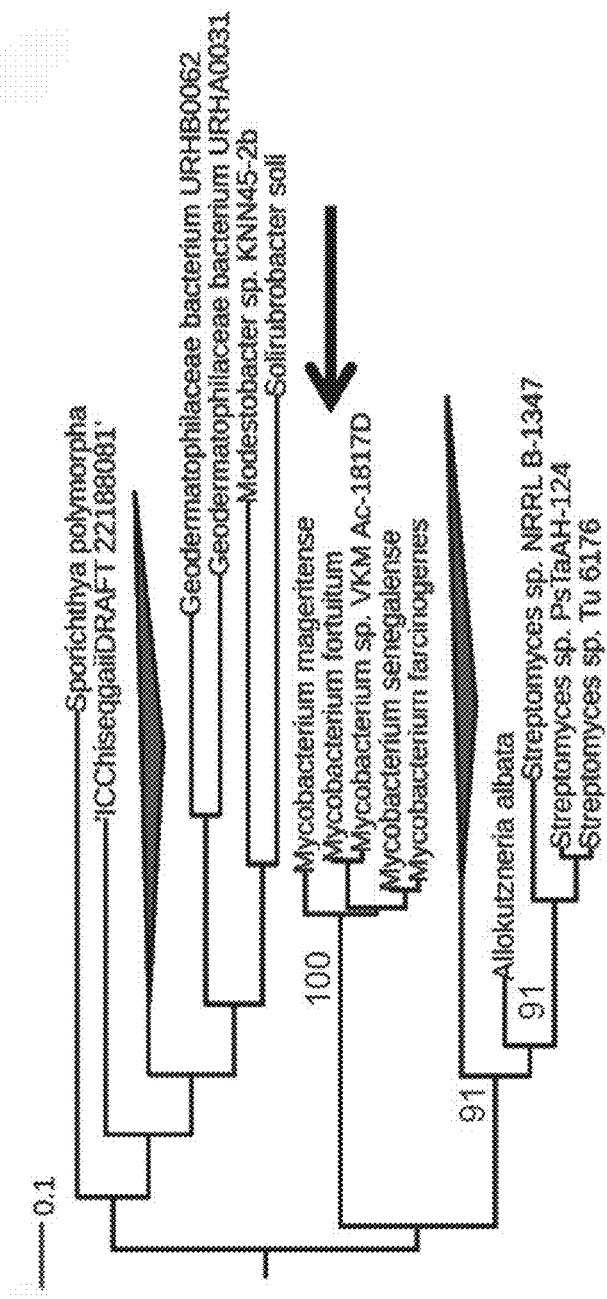

In this example, the evolutionary context of PodA was assessed by constructing an unrooted phylogenetic tree using the maximum likelihood algorithm with MEGA software (Tamura et al. (2013) Mol Biol Evol 30(12):2725-9), FIG. 15A. All available sequences found in a July 2015 NCBI BLAST search were used in this analysis. The resulting tree indicates that all related proteins are hypothetical, with the closest homologs being from other members of the *M. fortitum* complex, an emerging group of mycobacterial pathogens (Wallace et al. (1983) Reviews of Infectious Diseases 5(4):657-79). The homology analysis suggests that PodA defines a novel family of demethylases.

Example 7: Impact of 1-OH-PHZ on Biofilm Formation

It has been shown that PYO stimulates biofilm development in an Fe-independent fashion (Wang et al. (2011) J Bacteriol 193(14):3606-17). PodA converts PYO to 1-OH-PHZ, which can chelate Fe (Briard et al. (2015) Scientific Reports. 2015; 5). Previously, 1-OH-PHZ had not been considered in studies of phenazines and biofilm development (Dietrich et al. (2013) Journal of Bacteriology 195(7): 1371-80; Ramos et al. (2010) Res Microbiol. 161(3):187-91; Wang et al. (2011) J Bacteriol. 193(14):3606-17) because it is produced in very low abundance under standard culturing conditions (Price-Whelan et al. (2007). J Bacteriol. 189(17): 6372-81) and it had not been detected in CF sputum (Hunter et al. (2012) Am J Respir Cell Mol Biol. 47(6):738-45). Yet because interference with Fe(III) acquisition can block Pa PA14 biofilm development in vitro (Hunter et al. (2013). M Bio. 4(4). Epub 2013/08/22; O'May et al. (2009). J Med Microbiol. 58(Pt 6):765-73; Singh et al. (2002) Nature. 417(6888):552-5; Banin et al. (2006) Appl Environ Microbiol. 72(3):2064-9), in tissue culture (Moreau-Marquis et al. (2009) Am J Respir Cell Mol Biol. 41(3):305-13; Moreau-Marquis et al. (2008) Am J Physiol Lung Cell Mol Physiol. 295(1):L25-37), and in rabbit eye infections (Banin et al. (2008) P Natl Acad Sci USA. 105(43):16761-6), it was hypothesized that PodA or 1-OH-PHZox addition to cultures of Pa PA14 may abrogate biofilm development. Though previous studies revealed 1-OH-PHZred and PCAred to be strong Fe(III) reductants in vitro (Wang et al. (2008) Environ Sci Technol. 42(7):2380-6), and PCA to stimulate biofilm formation by making Fe(II) bioavailable (Wang et al. (2011) J Bacteriol. 193(14):3606-17), it was predicted that 1-OH-PHZred generation by PodA would, in the net, iron-limit P. aeruginosa cultures because its chelation ability (which other phenazines lack) would trump its ability to reduce Fe(III) to Fe(II), and in so doing, interfere with biofilm formation.

In this example, to check for an effect of PodA or 1-OH-PHZ on biofilm development, Pa PA14 was grown in 8-well chambered microscope slides designed for biofilm imaging, as previously reported (Das et al. (2015) Sci Rep. 5:8398). Overnight cultures of Pa PA14 were diluted to a starting optical density of 0.25 and grown directly on the slides (volume of 250 µl per chamber). After 5 h incubation at 37° C., planktonic cells were rinsed from the slide and remaining cells were stained with DAPI. Biofilm biomass was quantified by DAPI intensity on a Leica confocal microscope, with LAS X software. Pa PA14 incubated in the presence of 1 µM PodA or 100 µM 1-OHPHZox had ~50% the biofilm biomass of Pa PA14 alone (FIG. 20A).

In varying the amount of added 1-OH-PHZox, it was observed a dose-dependent response: the greater the [1-OHPHZox], the greater the biofilm inhibition, yet, under these conditions, saturating at 200 µM (FIG. 20B). To set the stage for flow-cell experiments to explore PodA and 1-OH-PHZ effects on biofilm inhibition and biofilm dissolution, the time course for biofilm development was mapped for Pa PA14 constitutively expressing YFP under constant flow in a minimal medium (FIG. 20C) as previously described (Wang et al. (2011) J Bacteriol. 193(14):3606-17). In addition, an appropriate initial tobramycin concentration to use in Pa PA14 biofilm experiments was also identified to test the hypothesis that PodA or 1-OH-PHZ can sensitize biofilms to antibiotics: Pa PA14 biofilms tolerate 20 µg/ml, 10× the MIC for tobramycin for planktonic cultures, similar to what has been reported for biofilms of Pa PAO1 (Bjarnsholt et al. (2005) Microbiol-Sgm. 2005; 151:373-83).

Example 8: PodA and 1-OH-PHZox Induce an Overlapping Transcriptomic Response as Measured by RNASeq Because 1-OH-PHZ induces iron starvation in *A. fumigatus* (Briard et al. (2015) Scientific Reports. 2015; 5), it was speculated that the abrogation of biofilm development in *P. aeruginosa* grown in the presence of either PodA or 1-OH-PHZox may be mediated by a response to Fe-limitation. To test this idea, changes to the transcriptome of Pa PA14 by RNASeq were assessed. After 5 h of incubation in the presence of PodA (1 µM), 1-OH-PHZ (200 µM) or PYO (200 µM), RNA was prepared from 1 ml of biofilm cultures (250 µl pooled from 4 static biofilm chambers) for analysis on an Illumina HiSeq 2500 sequencer at the Millard and Muriel Jacobs Genetics and Genomics Laboratory, as previously described (Babin et al. (2016) Proc Natl Acad Sci USA. 113(5):E597-E605; Kreamer et al. (2015) M Bio. 2015; 6(2):e02549. Epub 2015/02/26). This experiment was designed to identify genes that were likely to be specifically affected by PodA's transformation of PYO to 1-OH-PHZ under a condition that inhibited biofilm formation (FIG. 20A). As a reference for genes responsive to iron availability, these transcriptomes were compared to those previously found to respond to Fe(II) shock (Kreamer et al. (2015) M Bio. 2015; 6(2):e02549. Epub 2015/02/26).

As expected, strong (2-10-fold) upregulation of genes in several classic iron responsive pathways was observed when cells were treated with high concentrations of 1-OH-PHZox (FIG. 21A); these genes were downregulated in response to Fe(II) shock. Interestingly, the iron starvation signature did not dominate the transcription profile for cells treated with PodA. This may be because the total phenazine concentration was low at the timepoint used in the experiment, relative to the amount of Fe in the medium. Instead, a small cluster of genes were upregulated modestly in both the 1-OH-PHZox and the PodA treatments but not in the PYO treatment, raising the possibility that PodA-mediated conversion of even a small amount of PYO to 1-OH-PHZ can signal a response that inhibits biofilm development (FIG. 21B). These genes included the QapR regulon, upregulation of which causes decreased levels of the Pseudomonas quinolone signal PQS (Tipton et al. (2013) J Bacteriol. 195 (15):3433-41). This finding is intriguing because PQS appears to be important especially in early stages of biofilm formation and contributes to the regulation of PYO production (Diggle et al. (2003) Molecular Microbiology 50(1): 29-43). Other upregulated genes include a putative efflux pump-encoding operon. These preliminary results suggest that PodA-generated 1-OH-PHZ may impact biofilm development in two complementary ways: by sequestering iron when present at high concentrations and by interfering with key signaling pathways at lower concentrations.

The examples set forth above are provided to give those of ordinary skill in the art a complete disclosure and description of how to make and use the embodiments of the compounds, compositions, systems and methods of the disclosure, and are not intended to limit the scope of what the inventors regard as their disclosure. All patents and publications mentioned in the specification are indicative of the levels of skill of those skilled in the art to which the disclosure pertains.

The entire disclosure of each document cited (including patents, patent applications, journal articles, abstracts, laboratory manuals, books, or other disclosures) in the Background, Summary, Detailed Description, and Examples is hereby incorporated herein by reference. All references cited in this disclosure are incorporated by reference to the same extent as if each reference had been incorporated by reference in its entirety individually. However, if any inconsistency arises between a cited reference and the present disclosure, the present disclosure takes precedence.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the disclosure has been specifically disclosed by preferred embodiments, exemplary embodiments and optional features, modification and variation of the concepts herein disclosed can be resorted to by those skilled in the art upon the reading of the present disclosure, and that such modifications and variations are considered to be within the scope of this disclosure as defined by the appended claims.

It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

When a Markush group or other grouping is used herein, all individual members of the group and all combinations and possible subcombinations of the group are intended to be individually included in the disclosure. Every combination of components or materials described or exemplified herein can be used to practice the disclosure, unless otherwise stated. One of ordinary skill in the art will appreciate that methods, device elements, and materials other than those specifically exemplified can be employed in the practice of the disclosure without resort to undue experimentation. All art-known functional equivalents, of any such methods, device elements, and materials are intended to be included in this disclosure. Whenever a range is given in the specification, for example, a temperature range, a frequency range, a time range, or a composition range, all intermediate ranges and all sub-ranges, as well as, all individual values included in the ranges given are intended to be included in the disclosure. Any one or more individual members of a range or group disclosed herein can be excluded from a claim of this disclosure. The disclosure illustratively described herein suitably can be practiced in the absence of any element or elements, limitation or limitations which are not specifically disclosed herein.

A number of embodiments of the disclosure have been described. The specific embodiments provided herein are examples of useful embodiments of the disclosure and it will be apparent to one skilled in the art that the disclosure can be carried out using a large number of variations of the devices, device components, methods steps set forth in the present description. As will be obvious to one of skill in the art, methods and devices useful for the present methods can include a large number of optional composition and processing elements and steps.

In particular, it will be understood that various modifications may be made without departing from the spirit and scope of the present disclosure. Accordingly, other embodiments are within the scope of the following claims.

REFERENCES

1. J. M. Turner, A. J. Messenger, Occurrence, biochemistry and physiology of phenazine pigment production. *Adv Microb Physiol* 27, 211-275 (1986).
2. L. E. Dietrich, T. K. Teal, A. Price-Whelan, D. K. Newman, Redox-active antibiotics control gene expression and community behavior in divergent bacteria. *Science* 321, 1203-1206 (2008).
3. N. R. Glasser, S. E. Kern, D. K. Newman, Phenazine redox cycling enhances anaerobic survival in *Pseudomonas aeruginosa* by facilitating generation of ATP and a proton-motive force. *Mol Microbiol* 92, 399-412 (2014).
4. A. Price-Whelan, L. E. Dietrich, D. K. Newman, Pyocyanin alters redox homeostasis and carbon flux through central metabolic pathways in *Pseudomonas aeruginosa* PA14. *J Bacteriol* 189, 6372-6381 (2007).
5. I. Ramos, L. E. Dietrich, A. Price-Whelan, D. K. Newman, Phenazines affect biofilm formation by *Pseudomonas aeruginosa* in similar ways at various scales. *Res Microbiol* 161, 187-191 (2010).
6. Y. Wang et al., Phenazine-1-carboxylic acid promotes bacterial biofilm development via ferrous iron acquisition. *J Bacteriol* 193, 3606-3617 (2011).
7. W. J. Moree et al., Interkingdom metabolic transformations captured by microbial imaging mass spectrometry. *Proc Natl Acad Sci USA* 109, 13811-13816 (2012).
8. Z. J. Yang et al., Isolation, identification, and degradation characteristics of phenazine-1-carboxylic acid-degrading strain *Sphingomonas* sp. DP58. *Curr Microbiol* 55, 284-287 (2007).
9. K. C. Costa, M. Bergkessel, S. Saunders, J. Korlach, D. K. Newman, Enzymatic degradation of phenazines can generate energy and protect sensitive organisms from toxicity. *M Bio* 6, e01520-01515 (2015).
10. A. Krogh, B. Larsson, G. von Heijne, E. L. Sonnhammer, Predicting transmembrane protein topology with a hidden Markov model: application to complete genomes. *J Mol Biol* 305, 567-580 (2001).
11. R. Anand, R. Marmorstein, Structure and mechanism of lysine-specific demethylase enzymes. *J Biol Chem* 282, 35425-35429 (2007).
12. J. M. Hagel, P. J. Facchini, Biochemistry and occurrence of 0-demethylation in plant metabolism. *Front Physiol* 1, 14 (2010).
13. R. M. Summers et al., Novel, highly specific N-demethylases enable bacteria to live on caffeine and related purine alkaloids. *J Bacteriol* 194, 2041-2049 (2012).
14. Y. Song et al., High-resolution comparative modeling with Rosetta CM. *Structure* 21, 1735-1742 (2013).
15. S. Raman et al., Structure prediction for CASP8 with all-atom refinement using Rosetta. *Proteins* 77 Suppl 9, 89-99 (2009).
16. D. E. Kim, D. Chivian, D. Baker, Protein structure prediction and analysis using the Robetta server. *Nucleic Acids Res* 32, W526-531 (2004).
17. A. Gutteridge, J. M. Thornton, Understanding nature's catalytic toolkit. *Trends Biochem Sci* 30, 622-629 (2005).
18. C. T. Walsh, T. A. Wencewicz, Flavoenzymes: versatile catalysts in biosynthetic pathways. *Nat Prod Rep* 30, 175-200 (2013).
19. C. B. Whitchurch, T. Tolker-Nielsen, P. C. Ragas, J. S. Mattick, Extracellular DNA required for bacterial biofilm formation. *Science* 295, 1487 (2002).
20. T. Das, M. Manefield, Pyocyanin promotes extracellular DNA release in *Pseudomonas aeruginosa*. *PLoS One* 7, e46718 (2012).
21. T. Das, M. Manefield, Phenazine production enhances extracellular DNA release via hydrogen peroxide generation in *Pseudomonas aeruginosa*. *Commun Integr Biol* 6, e23570 (2013).

22. T. Das et al., Phenazine virulence factor binding to extracellular DNA is important for *Pseudomonas aeruginosa* biofilm formation. *Sci Rep* 5, 8398 (2015).
23. L. E. Dietrich et al., Bacterial community morphogenesis is intimately linked to the intracellular redox state. *J Bacteriol* 195, 1371-1380 (2013).
24. G. Borriello et al., Oxygen limitation contributes to antibiotic tolerance of *Pseudomonas aeruginosa* in biofilms. *Antimicrob Agents Chemother* 48, 2659-2664 (2004).
25. Y. Wang, S. E. Kern, D. K. Newman, Endogenous phenazine antibiotics promote anaerobic survival of *Pseudomonas aeruginosa* via extracellular electron transfer. *J Bacteriol* 192, 365-369 (2010).
26. Y. Wang, D. K. Newman, Redox reactions of phenazine antibiotics with ferric (hydr)oxides and molecular oxygen. *Environ Sci Technol* 42, 2380-2386 (2008).
27. T. Bjarnsholt et al., The in vivo biofilm. *Trends Microbiol* 21, 466-474 (2013).
28. K. N. Kragh et al., Role of Multicellular Aggregates in Biofilm Formation. *M Bio* 7, e00237 (2016).
29. E. S. Cowley, S. H. Kopf, A. LaRiviere, W. Ziebis, D. K. Newman, Pediatric cystic fibrosis sputum can be chemically dynamic, anoxic, and extremely reduced due to hydrogen sulfide formation. *M Bio* 6, e00767 (2015).
30. M. E. Taga, N. A. Larsen, A. R. Howard-Jones, C. T. Walsh, G. C. Walker, BluB cannibalizes flavin to form the lower ligand of vitamin B12. *Nature* 446, 449-453 (2007).
31. L. E. Dietrich, A. Price-Whelan, A. Petersen, M. Whiteley, D. K. Newman, The phenazine pyocyanin is a terminal signalling factor in the quorum sensing network of *Pseudomonas aeruginosa*. *Mol Microbiol* 61, 1308-1321 (2006).
32. L. G. Rahme et al., Common virulence factors for bacterial pathogenicity in plants and animals. *Science* 268, 1899-1902 (1995).
33. F. W. Studier, B. A. Moffatt, Use of bacteriophage T7 RNA polymerase to direct selective high-level expression of cloned genes. *J Mol Biol* 189, 113-130 (1986).
34. S. K. DasGupta, S. Jain, D. Kaushal, A. K. Tyagi, Expression systems for study of mycobacterial gene regulation and development of recombinant BCG vaccines. *Biochem Biophys Res Commun* 246, 797-804 (1998).
35. Y. P. Shih, H. C. Wu, S. M. Hu, T. F. Wang, A. H. Wang, Self-cleavage of fusion protein in vivo using TEV protease to yield native protein. *Protein Sci* 14, 936-941 (2005).
36. M. M. Bradford, A rapid and sensitive method for the quantitation of microgram quantities of protein utilizing the principle of protein-dye binding. *Anal Biochem* 72, 248-254 (1976).
37. T. Nash, The colorimetric estimation of formaldehyde by means of the Hantzsch reaction. *Biochem J* 55, 416-421 (1953).
38. S. B. Jones, C. M. Terry, T. E. Lister, D. C. Johnson, Determination of submicromolar concentrations of formaldehyde by liquid chromatography. *Anal. Chem.* 71, 4030-4033 (1999).
39. N. L. Sullivan, D. S. Tzeranis, Y. Wang, P. T. So, D. Newman, Quantifying the dynamics of bacterial secondary metabolites by spectral multiphoton microscopy. *ACS Chem Biol* 6, 893-899 (2011).
40. D. V. Mavrodi et al., Functional analysis of genes for biosynthesis of pyocyanin and phenazine-1-carboxamide from *Pseudomonas aeruginosa* PAO1. *J Bacteriol* 183, 6454-6465 (2001).
41. G. Kemmer, S. Keller, Nonlinear least-squares data fitting in Excel spreadsheets. *Nat Protoc* 5, 267-281 (2010).
42. H. McIlwain, The phenazine series. Part IV. Reactions of alkyl phenazonium salts; the phenazyls. *J Chem Soc*, 1704-1711 (1937).
43. W. Kabsch, Xds. *Acta Crystallogr D Biol Crystallogr* 66, 125-132 (2010).
44. W. Kabsch, Integration, scaling, space-group assignment and post-refinement. *Acta Crystallogr D Biol Crystallogr* 66, 133-144 (2010).
45. P. Evans, Scaling and assessment of data quality. *Acta Crystallogr D Biol Crystallogr* 62, 72-82 (2006).
46. P. R. Evans, G. N. Murshudov, How good are my data and what is the resolution? *Acta Crystallogr D Biol Crystallogr* 69, 1204-1214 (2013).
47. J. E. Padilla, T. O. Yeates, A statistic for local intensity differences: robustness to anisotropy and pseudo-centering and utility for detecting twinning. *Acta Crystallogr D Biol Crystallogr* 59, 1124-1130 (2003).
48. M. D. Winn et al., Overview of the CCP4 suite and current developments. *Acta Crystallogr D Biol Crystallogr* 67, 235-242 (2011).
49. A. J. McCoy et al., Phaser crystallographic software. *J Appl Crystallogr* 40, 658-674 (2007).
50. P. Emsley, B. Lohkamp, W. G. Scott, K. Cowtan, Features and development of Coot. *Acta Crystallogr D Biol Crystallogr* 66, 486-501 (2010).
51. T. C. Terwilliger et al., Iterative model building, structure refinement and density modification with the PHENIX AutoBuild wizard. *Acta Crystallogr D Biol Crystallogr* 64, 61-69 (2008).
52. J. J. Headd et al., Use of knowledge-based restraints in phenix.refine to improve macromolecular refinement at low resolution. *Acta Crystallogr D Biol Crystallogr* 68, 381-390 (2012).
53. P. V. Afonine et al., Towards automated crystallographic structure refinement with phenix.refine. *Acta Crystallogr D Biol Crystallogr* 68, 352-367 (2012).
54. T. C. Terwilliger, P. D. Adams, N. W. Moriarty, J. D. Cohn, Ligand identification using electron-density map correlations. *Acta Crystallogr D Biol Crystallogr* 63, 101-107 (2007).
55. T. C. Terwilliger, H. Klei, P. D. Adams, N. W. Moriarty, J. D. Cohn, Automated ligand fitting by core-fragment fitting and extension into density. *Acta Crystallogr D Biol Crystallogr* 62, 915-922 (2006).
56. P. D. Adams et al., PHENIX: a comprehensive Python-based system for macromolecular structure solution. *Acta Crystallogr D Biol Crystallogr* 66, 213-221 (2010).
57. N. W. Moriarty, R. W. Grosse-Kunstleve, P. D. Adams, electronic Ligand Builder and Optimization Workbench (eLBOW): a tool for ligand coordinate and restraint generation. *Acta Crystallogr D Biol Crystallogr* 65, 1074-1080 (2009).
58. M. D. Winn, M. N. Isupov, G. N. Murshudov, Use of TLS parameters to model anisotropic displacements in macromolecular refinement. *Acta Crystallogr D Biol Crystallogr* 57, 122-133 (2001).
59. T. Das, S. K. Kutty, N. Kumar, M. Manefield, Pyocyanin facilitates extracellular DNA binding to *Pseudomonas aeruginosa* influencing cell surface properties and aggregation. *PLoS One* 8, e58299 (2013).
60. C. A. Schneider, W. S. Rasband, K. W. Eliceiri, NIH Image to ImageJ: 25 years of image analysis. *Nat Methods* 9, 671-675 (2012).

61. S. Bolte, F. P. Cordelieres, A guided tour into subcellular colocalization analysis in light microscopy. *J Microsc* 224, 213-232 (2006).

62. D. Cohen et al., Oligoribonuclease is a central feature of cyclic diguanylate signaling in *Pseudomonas aeruginosa. Proc Natl Acad Sci USA* 112, 11359-11364 (2015).

The invention claimed is:

1. A method for treating and/or preventing a bacterial infection by bacteria producing pyocyanin-like phenazines of formula (III) in an individual, the method comprising
administering to the individual an effective amount of one or more phenazine degrading agents comprising a pyocyanin demethylase and/or a derivative thereof, alone or in combination with an antibiotic and/or other antimicrobial,
wherein formula (III) is

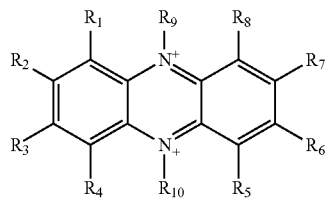

(III)

where $R_1$-$R_7$ are independently selected from hydrogen, hydroxy, alkoxy, alkyl, alkenyl, alkynyl, aryl, heteroaryl, acyl, $R_{10}$ is a methyl group, $R_9$ is hydrogen and $R_8$ is a negatively charged substituent,
wherein the pyocyanin demethylase comprises the amino acid sequence of SEQ ID NO: 1 having demethylating residues D68, D72, H121, E154, and Y156;
wherein the derivative has at least 30% sequence identity with SEQ ID NO:1, and comprises the demethylating residues of SEQ ID NO: 1 and/or a functional equivalent residue of the demethylating residues; and
wherein the derivative has the ability to demethylate the pyocyanin-like phenazines of formula (III).

2. The method of claim 1, wherein the derivative of the pyocyanin demethylase is a protein having sequence comprising SEQ ID NO:2.

3. The method of claim 1, wherein the derivative of the pyocyanin demethylase has at least 40% sequence identity with SEQ ID NO:1.

4. The method of claim 1, wherein the antibiotic is selected from the group consisting of Amoxicillin and clavulanic acid, Methicillin, oxacillin, nafcillin, cloxacillin, dicloxacillin, carbenicillin, ticarcillin, piperacillin, mezlocillin, azlocillin, ticarcillin and clavulanic acid, piperacillin and tazobactam, cephalexin, cefdinir, cefprozil, cefaclor, cefuroxime, sulfisoxazole, erythromycin/sulfisoxazole, tobramycin, amikacin, gentamicin, erythromycin, clarithromycin, azithromycin, tetracycline, doxycycline, minocycline, tigecycline, ciprofloxacin, levofloxacin, vancomycin, linezolid, imipenem, meripenem, and aztreonam.

5. The method of claim 1, wherein the bacteria producing pyocyanin-like phenazines of formula (III) is selected from the group consisting of *Staphylococcus aureus, Pseudomonas, Burkholderia cepacian*, and mycobacteria.

6. The method of claim 1, wherein the bacteria producing pyocyanin-like phenazines of formula (III) is comprised in a biofilm.

7. The method of claim 1, wherein in formula III at least one of R1-R7 is a hydroxy group or a methoxy group.

8. The method of claim 1, wherein the one or more phenazine degrading agents alone or in combination with an antibiotic and/or other antimicrobial are in a form of an aqueous solution, cream, solid powder, tablets, or aerosols.

9. The method of claim 1, wherein the derivative of the pyocyanin demethylase has at least 50% sequence identity with SEQ ID NO:1.

10. The method of claim 1, wherein the derivative of the pyocyanin demethylase has least 60% sequence identity with SEQ ID NO:1.

11. The method of claim 1, wherein the derivative of the pyocyanin demethylase has at least 70% sequence identity with SEQ ID NO:1.

12. The method of claim 1, wherein one or more of the demethylating residues of the derivative are residues functionally equivalent of demethylating residues D68, D72, H121, E154, and Y156 of SEQ ID NO: 1.

13. The method of claim 1, wherein the derivative of the pyocyanin demethylase has at least 30% identity, with SEQ ID NO: 2.

14. The method of claim 1, wherein the derivative of the pyocyanin demethylase has at least 50% identity, with SEQ ID NO: 2.

15. The method of claim 1, wherein the derivative of the pyocyanin demethylase has at least 70% identity, with SEQ ID NO: 2.

16. The method of claim 11, wherein one or more of the demethylating residues of the derivative are residues functionally equivalent to corresponding one or more demethylating residues of SEQ ID NO: 2.

* * * * *

SEQUENCE LISTING

```
<160> NUMBER OF SEQ ID NOS: 16

<210> SEQ ID NO 1
<211> LENGTH: 162
<212> TYPE: PRT
<213> ORGANISM: Mycobacterium fortuitum

<400> SEQUENCE: 1

Met Thr Gly Lys Thr Lys Pro Ala Ile Ile Gly Gly Val Ala Ile Thr
1               5                   10                  15

Ala Leu Ala Ala Ala Gly Leu Gly Val Trp Leu Phe Thr Asp Gly Arg
            20                  25                  30

Gly Gly Arg Ser Thr Thr Glu Pro Val Thr Met Thr Leu Asp Val Lys
        35                  40                  45

Asn Asp Gln Val Ala Lys His Asp Phe Gly Lys Pro Gly Met Asp Val
    50                  55                  60

Gly Asp Met Asp Ile Phe Ser Asp Ile Leu Ser Val Asp Gly Lys Gln
65                  70                  75                  80

Val Gly Tyr Asp Gly Gly Ala Cys Phe Phe Thr Asn Val Thr Pro Asp
                85                  90                  95

Asn Pro Met Thr Tyr Cys Glu Leu Thr Ile His Leu Asp Ala Gly Glu
            100                 105                 110

Ile Phe Ala Arg Ser Leu Thr Pro His Thr Leu Ala Pro Phe Thr Met
        115                 120                 125

Ala Ile Thr Gly Gly Thr Gly Glu Tyr Ala Asn Ser Lys Gly Glu Leu
    130                 135                 140

Thr Val Ser Gly Val Ala Thr Pro Asp Glu Lys Tyr Glu Leu Lys Leu
145                 150                 155                 160

Thr Lys

<210> SEQ ID NO 2
<211> LENGTH: 141
<212> TYPE: PRT
<213> ORGANISM: Mycobacterium fortuitum

<400> SEQUENCE: 2

Met Asp Gly Arg Gly Gly Arg Ser Thr Thr Glu Pro Val Thr Met Thr
1               5                   10                  15

Leu Asp Val Lys Asn Asp Gln Val Ala Lys His Asp Phe Gly Lys Pro
            20                  25                  30

Gly Met Asp Val Gly Asp Met Asp Ile Phe Ser Asp Ile Leu Ser Val
        35                  40                  45

Asp Gly Lys Gln Val Gly Tyr Asp Gly Gly Ala Cys Phe Phe Thr Asn
    50                  55                  60

Val Thr Pro Asp Asn Pro Met Thr Tyr Cys Glu Leu Thr Ile His Leu
65                  70                  75                  80

Asp Ala Gly Glu Ile Phe Ala Arg Ser Leu Thr Pro His Thr Leu Ala
                85                  90                  95

Pro Phe Thr Met Ala Ile Thr Gly Gly Thr Gly Glu Tyr Ala Asn Ser
            100                 105                 110

Lys Gly Glu Leu Thr Val Ser Gly Val Ala Thr Pro Asp Glu Lys Tyr
        115                 120                 125
```

Glu Leu Lys Leu Thr Lys Ala Glu Asn Leu Tyr Phe Gln
    130                 135                 140

<210> SEQ ID NO 3
<211> LENGTH: 32
<212> TYPE: DNA
<213> ORGANISM: Artificial Sequence
<220> FEATURE:
<223> OTHER INFORMATION: Synthetic polynucleotide

<400> SEQUENCE: 3
aaaacatatg gacggtcgcg gcggccggag ta                           32

<210> SEQ ID NO 4
<211> LENGTH: 83
<212> TYPE: DNA
<213> ORGANISM: Artificial Sequence
<220> FEATURE:
<223> OTHER INFORMATION: Synthetic polynucleotide

<400> SEQUENCE: 4
aaaactgcag tcaatggtga tggtgatggt ggctctggaa gtacaggttt tcggctttcg   60
tcagtttcaa ttcgtacttc tca                                          83

<210> SEQ ID NO 5
<211> LENGTH: 34
<212> TYPE: DNA
<213> ORGANISM: Artificial Sequence
<220> FEATURE:
<223> OTHER INFORMATION: Synthetic polynucleotide

<400> SEQUENCE: 5
aaaacatatg gacggtcgcg gcggccggag taca                         34

<210> SEQ ID NO 6
<211> LENGTH: 36
<212> TYPE: DNA
<213> ORGANISM: Artificial Sequence
<220> FEATURE:
<223> OTHER INFORMATION: Synthetic polynucleotide

<400> SEQUENCE: 6
ttttgcggcc gctcaatggt gatggtgatg gtggct                       36

<210> SEQ ID NO 7
<211> LENGTH: 50
<212> TYPE: DNA
<213> ORGANISM: Artificial Sequence
<220> FEATURE:
<223> OTHER INFORMATION: Synthetic polynucleotide

<400> SEQUENCE: 7
gataatccaa tgacctattc cgaactgacc attcacctcg atgcaggtga        50

<210> SEQ ID NO 8
<211> LENGTH: 56
<212> TYPE: DNA
<213> ORGANISM: Artificial Sequence
<220> FEATURE:
<223> OTHER INFORMATION: Synthetic polynucleotide

<400> SEQUENCE: 8
cggcgtcaca ttggtgaaaa aggacgcgcc gccgtcatat ccgacctgct taccgt   56

<210> SEQ ID NO 9

```
<211> LENGTH: 51
<212> TYPE: DNA
<213> ORGANISM: Artificial Sequence
<220> FEATURE:
<223> OTHER INFORMATION: Synthetic polynucleotide

<400> SEQUENCE: 9
ggataatcca atgacctatg ccgaactgac cattcacctc gatgcaggtg a            51

<210> SEQ ID NO 10
<211> LENGTH: 57
<212> TYPE: DNA
<213> ORGANISM: Artificial Sequence
<220> FEATURE:
<223> OTHER INFORMATION: Synthetic polynucleotide

<400> SEQUENCE: 10
ggcgtcacat tggtgaaaaa ggccgcgccg ccgtcatatc cgacctgctt accgtct      57

<210> SEQ ID NO 11
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 11
gccatcttct ccgacatcct ctcggtaga                                     29

<210> SEQ ID NO 12
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 12
catgtctccg acatccatac ccggt                                         25

<210> SEQ ID NO 13
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 13
gccacactcg cacctttcac catggcca                                      28

<210> SEQ ID NO 14
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 14
cggggtgagg ctacgggcaa agatctca                                      28

<210> SEQ ID NO 15
<211> LENGTH: 29
<212> TYPE: DNA
<213> ORGANISM: Artificial Sequence
<220> FEATURE:
<223> OTHER INFORMATION: Synthetic polynucleotide
```

```
<400> SEQUENCE: 15
gcgaagtacg aattgaaact gacgaaagc                                      29

<210> SEQ ID NO 16
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 16
atcgggagtc gcaacaccgg atacggt                                        27
```